US007163685B2

(12) United States Patent
Diamond et al.

(10) Patent No.: US 7,163,685 B2
(45) Date of Patent: Jan. 16, 2007

(54) HUMAN CYTOMEGALOVIRUS ANTIGENS EXPRESSED IN MVA AND METHODS OF USE

(75) Inventors: Don Jeffrey Diamond, Glendora, CA (US); Zhongde Wang, Arcadia, CA (US)

(73) Assignee: City of Hope, Duarte, CA (US)

( * ) Notice: Subject to any disclaimer, the term of this patent is extended or adjusted under 35 U.S.C. 154(b) by 121 days.

(21) Appl. No.: 10/825,629

(22) Filed: Apr. 16, 2004

(65) Prior Publication Data

US 2004/0265325 A1 Dec. 30, 2004

Related U.S. Application Data

(60) Provisional application No. 60/463,026, filed on Apr. 16, 2003.

(51) Int. Cl.
*A61K 39/12* (2006.01)
(52) U.S. Cl. .............................. 424/199.1; 424/229.1; 424/204.1; 435/6
(58) Field of Classification Search ............. 424/144.1, 424/229.1, 204.1; 435/6, 320.1, 69.1
See application file for complete search history.

(56) References Cited

U.S. PATENT DOCUMENTS

| | | | |
|---|---|---|---|
| 5,591,439 | A | 1/1997 | Plotkin et al. |
| 6,074,645 | A | 6/2000 | Diamond et al. |
| 6,133,433 | A | 10/2000 | Pande et al. |
| 6,156,317 | A | 12/2000 | Diamond et al. |
| 6,242,567 | B1 | 6/2001 | Pande et al. |
| 6,251,399 | B1 | 6/2001 | Diamond et al. |
| 6,440,422 | B1 * | 8/2002 | Sutter et al. ............. 424/199.1 |
| 6,544,521 | B1 | 4/2003 | Diamond |
| 6,562,345 | B1 | 5/2003 | Diamond et al. |
| 6,632,435 | B1 | 10/2003 | Diamond |
| 6,632,438 | B1 * | 10/2003 | Paoletti et al. ........... 424/199.1 |
| 6,726,910 | B1 | 4/2004 | Diamond |
| 6,727,093 | B1 | 4/2004 | Diamond |
| 6,733,973 | B1 | 5/2004 | Diamond |
| 6,843,992 | B1 | 1/2005 | Diamond |

FOREIGN PATENT DOCUMENTS

WO    WO 02/34769 A2    5/2002

OTHER PUBLICATIONS

Adler et al., "A Canarypox Vector Expressing Cytomegalovirus (CMV) Glycoprotein B Primes for Antibody Responses to a Live Attenuated CMV Vaccine (Towne)," J. of Infect. Dis. 180:843-846, 1999.
Aguado et al., "Prospective randomized trial of efficacy of ganciclovir versus that of anti-cytomegalovirus (CMV) immunoglobulin to prevent CMV disease in CMV-seropositive heart transplant recipients treated with OKT3." Antimicrob. Agents Chemother. 39:1643-1645, 1995.
Allen et al., "Induction of AIDS Virus-Specific CTL Activity in Fresh, Unstimulated Peripheral Blood Lymphocytes From Rhesus Macaques Vaccinated With a DNA Prime/Modified Vaccinia Virus Ankara Boost Regimen," J. Immunol. 164:4968-4978, 2000.
Alp et al., "Fine specificity of cellular immune responses in humans to human cytomegalovirus immediate-early 1 protein." J. Virol. 65:4812-4820, 1991.
Amara et al., "Different Patterns of Immune Responses but Similar Control of a Simian- Human Immunodeficiency Virus 89.6P Mucosal Challenge by Modified Vaccinia Virus Ankara (MVA) and DNA/MVA Vaccines." J. Virol. 76:7625-7631, 2002.
Amara et al., "Control of a Mucosal Challenge and Prevention of AIDS by a Multiprotein DNA/MVA Vaccine." Science 292:69-74, 2001.
Banks et al., "A Major Neutralizing Domain Maps Within the Carboxyl-Terminal Half of the Cleaved Cytomegalovirus B Glycoprotein." J. Gen. Virol. 70:979-985, 1989.
Basgoz et al., "The Amino Terminus of Human Cytomegalovirus Glycoprotein B Contains Epitopes That Vary Among Strains." J. of Gen. Virol. 73:983-988, 1992.
Bender et al., "Oral immunization with a replication-deficient recombinant vaccinia virus protects mice against influenza." J. Virol. 70:6418-6424, 1996.
Berencsi et al., "A Canarypox Vector-Expressing Cytomegalovirus (CMV) Phosphoprotein 65 Induces Long-lasting Cytotoxic T Cell Responses in Human CMV-Seronegative Subjects." J. Infect. Dis. 183:1171-1179, 2001.
Berencsi et al., "Murine Cytotoxic T Cell Response Specific for Human Cytomegalovirus Glycoprotein B (gB) Induced by Adenovirus and Vaccinia Virus Recombinants Expressing gB." J. Gen. Virol. 74(pt 11):2507-2512, 1993.
Bernstein et al., "Effect of Previous or Simultaneous Immunization With Canarypox Expressing Cytomegalovirus (CMV) Glycoprotein B (gB) on Response Subunit gB Vaccine Plus MF59 in Healthy CMV-Seronegative Adults." J. Infect. Dis. 185:686-690, 2002.
Benmohamed et al., "Intranasal Administration of a Synthetic Lipopeptide Without Adjuvant Induces Systemic Immune Responses." Immunology 106:113-121, 2002.

(Continued)

*Primary Examiner*—Ali R. Salimi
(74) *Attorney, Agent, or Firm*—Rothwell, Figg, Ernst & Manbeck pc

(57) ABSTRACT

DNA and protein constructs useful in producing vaccines against human cytomegalovirus contain optionally N-end modified and N-terminal ubiquitinated human cytomegalovirus antigenic proteins, including pp65, pp150, IE1, gB and antigenic fragments thereof. Vaccine viruses, in particular poxviruses such as vaccinia and Modified Vaccinia Ankara, that express the constructs may be used as vaccines to augment the immune response to human cytomegalovirus, both prophylatically and in patients already carrying human cytomegalovirus, as well as to create and expand cytomegalovirus-reactive T cells for transfer of adoptive immunity.

7 Claims, 32 Drawing Sheets

OTHER PUBLICATIONS

Blanchard et al., "Modified Vaccinia Virus Ankara Undergoes Limited Replication in Human Cells and Lacks Several Immunomodulatory Proteins: implications for use as a human vaccine." J. Gen. Virol. 79(Pt 5):1159-1167, 1998.

Boppana et al., "Recognition of Human Cytomegalovirus Gene Products by HCMV-Specific Cytotoxic T Cells." Virology, 222:293-296, 1996.

Borysiewicz et al., "Human Cytomegalovirus-Specific Cytotoxic T Cells." J. Exp. Med. 168:919-931, 1988.

Britt et al., "Formulation of an Immunogenic Human Cytomegalovirus Vaccine: Responses in Mice." J. Infect Dis. 171:18-25, 1995.

Britt et al., "Cell Surface Expression of Human Cytomegalovirus (HCMV) gp55-116 (gB): Use of HCMV-Recombinant Vaccinia Virus-Infected Cells in Analysis of the Human Neutralizing Antibody Response." J. Virol. 64:1079-1085, 1990.

Carroll et al., "Host Range and Cytopathogenicity of the Highly Attenuated MVA Strain of Vaccinia Virus: Propagation and Generation of Recombinant Viruses in a Nonhuman Mammalian Cell Line." Virology 238:198-211, 1997.

Carroll et al., "Highly Attenuated Modified Vaccinia Virus Ankara (MVA) As An Effective Recombinant Vector: A Murine Tumor Model." Vaccine 15 (4):387-394, 1997.

Chee et al., "Analysis of the Protein-Coding Content of the Sequence of Human Cytomegalovirus Strain AD169." Current Topics in Microbiol. Immunol. 154:126-169, 1990.

Cranage et al., "Identification of the Human Cytomegalovirus Glycoprotein B Gene and Induction of Neutralizing Antibodies Via Its Expression in Recombinant Vaccinia Virus." EMBO J. 5(11):3057-3063, 1986.

D'Amaro et al., "A Computer Program for Predicting Possible Cytotoxic T Lymphocyte Epitopes Based on HLA Class I Peptide-Binding Motifs." Human Immunol. 43:13-18, 1995.

Degano et al., "Gene Gun Intradermal DNA Immunization Followed By Boosting With Modified Vaccinia Virus Ankara: Enhanced CD8* T Cell Immunogenicity and Protective Efficacy in the Influenza and Malaria Models." Vaccine 18:623-632, 2000.

Delogu et al., "DNA Vaccine Combinations Expressing Either Tissue Plasminogen Activator Signal Sequence Fusion Proteins or Ubiquitin-Conjugated antigens Induce Sustained Protective Immunity in a Mouse Model of pulmonary Tuberculosis." Infect. and Immunity 70:292-302, 2002.

Delogu et al., "DNA Vaccination against Tuberculosis: expression of a ubiquitin- conjugated tuberculosis protein enhances antimycobacterial immunity." Infect. Immunity 68.6:3097-3102, 2000.

Diamond et al., "Development of a Candidate HLA A*0201 Restricted Peptide-Based Vaccine Against Human Cytomegalovirus Infection." Blood 90(5):1751-1767, 1997.

Einsele et al., "Induction of CMV-specific T-cell lines using Ag-presenting cells pulsed with CMV protein or peptide." Cytotherapy 4:49-54, 2002.

Elkington et al., "Ex Vivo Profiling of CD8*-T-Cell Responses to Human Cytomegalovirus Reveals Broad and Multispecific Reactivities in Healthy Virus Carriers." J. Virol. 77(9):5226-5240, 2003.

Endresz et al., "Induction of Human Cytomegalovirus (HCMV)-Glycoprotein B (gB)-Specific Neutralizing Antibody and Phosphoprotein 65 (pp65)-Specific Cytotoxic T Lymphocyte Responses By Naked DNA Immunization." Vaccine 17:50-58, 1999.

Endresz et al., "Optimization of DNA Immunization Against Human Cytomegalovirus." Vaccine 19:3972-3980, 2001.

Firat et al., "Comparative analysis of the CD8(+) T cell repertoires of H-2 class I wild-type/ HLA-A2.1 and H-2 class I knockout/HLA-A2.1 transgenic mice." Int. Immunol. 14:925-934, 2002.

Fu et al., "Induction of MHC Class I-Restricted CTL Responses by DNA Immunization with Ubiquitin-Influenza Virus Nucleoprotein Fusion Antigens." Vaccine 16(18):1711-1717, 1998.

Gallez-Hawkins et al., "Kinase-Deficient CMVpp65 Triggers a CMVpp65 Specific T-Cell Immune Response in HLA-A*0201.Kb Transgenic Mice after DNA Immunization." Scand. J. Immunol. 55:592-598, 2002.

Gallez-Hawkins et al., "Use of Transgenic HLA A*0201/Kb and HHD II Mice to Evaluate Frequency of Cytomegalovirus IE1-Derived Ppeptide Usage in Eliciting Human CD8 Cytokine Response." J. Virol. 77:4457-4462, 2003.

Gilbert et al., "Selective Interference with Class I Major Histocompatibilty Complex Presentation of the Major Immediate-Early Protein Following Infection with Human Cytomegalovirus." J. Virol. 67:3461-3469, 1993.

Gillespie et al., "Functional heterogeneity and High Frequencies of Cytomegalovirus-Specific CD8(+) T Lymphocytes in Healthy Seropositive Donors." J. Virol. 74:8140-8150, 2000.

Gonczol et al., "Progress in Vaccine Development for Prevention of Human Cytomegalovirus Infection." Curr. Top. Microbiol. Immunol. 154:255-274, 1990.

Gonczol et al., High Expression of Human Cytomegalovirus (HCMV)-gB Protein in Cells Infected With a Vaccinia-gB Recombinant: The Importance of the gB Protein in HCMV Immunity. Vaccine 9:631-637, 1991.

Gonczol et al., Preclinical Evaluation of an ALVAC (Canarypox)-Human Cytomegalovirus Glycoprotein B Vaccine Candidate. Vaccine 13(12):1080-1085,1995.

Gonczol et al., "Isolated gA/gB Glycoprotein Complex of Human Cytomegalovirus Envelope Induces Humoral and Cellular Immume Responses in Human Volunteers." Vaccine 8:130-136, 1990.

Gonczol et al., "Development of a Cytomegalovirus Vaccine: Lessons From Recent Clinical Trials." Exp. Opin. Biol. Ther. 1(3):401-412, 2001.

Grant et al., "Rate of Antigen Degradation by the Ubiquitin-Proteasome Pathway Influences MHC Class I Presentation." J. Immunol. 155:3750-3758, 1995.

Griffiths, "Cytomegalovirus Therapy: Current Constraints and Future Opportunities", Curr. Opin. Infect. Dis. 14:765-768, 2001.

Griffiths, "The Treatment of Cytomegalovirus Infection." J. of Antimicrobial Chem. 49:243-253, 2002.

Gyulai et al., "Cytotoxic T Lymphocyte (CTL) Responses to Human Cytomegalovirus pp65, IE1-Exon4, gB, pp150, and pp28 in Healthy Individuals: Reevaluation of Prevalence of IE1-Specific CTLs." J. Infect. Dis. 181:1537-1546, 2000.

Hamel et al., "Characterization of Antigen-Specific Repertoire Diversity Following in Vitro Restimulation by a Recombinant Adenovirus Expressing Human Cytomegalovirus pp65." Eur. J. Immunol. 33:760-768, 2003.

Hanke et al., "Effective Induction of HIV-Specific CTL by Multi-epitope Using Gene Gun in a Combined Vaccination Regime." Vaccine 17:589-596, 1999.

Hanke et al., "Effective Induction of Simian Immunodeficiency Virus-Specific Cytotoxic T Lymphocytes in Macaques by Using a Multiepitope Gene and DNA Prime-Modified Vaccinia Virus Ankara Boost Vaccination Regimen." J. Virol. 73(9):7524-7532, 1999.

Hanke et al., "Pre-clinical Development of a Multi-CTL Epitope-based DNA Prime MVA Boost Vaccine for AIDS." Immunol. Lett. 66:177-181, 1999.

Hanke et al., "Immunogenicities of Intravenous and Intramuscular Administrations of Modified Vaccinia Virus ankara-Based Multi-CTL Eptiope Vaccine for Human Immunodeficiency Virus Type 1 in Mice." J. Gen. Virol. 79:83-90, 1998.

Hanke et al., "Design and Construction of an experimental HIV-1 vaccine for a year-2000 clinical trial in Kenya." Nat. Med. 6(9):951-955, 2000.

Hirsch et al., "Patterns of viral replication correlate with outcome in simian immunodeficiency virus (SIV)-infected macaques: effect of prior immunization with a trivalent SIV vaccine in modified vaccinia virus Ankara." J. Virol. 70(6):3741-3752, 1996.

Ishioka et al., "Utilization of MHC Class I Transgenic Mice for Development of Minigene DNA Vaccines Encoding Multiple HLA-Restricted CTL Epitopes." J. Immunol. 162:3915-3925, 1999.

Keever-Taylor et al., "Cytomegalovirus-Specific Cytolytic T-Cell Lines and Clones Generated Against Adenovirus-pp65-Infected Dendritic Cells." Biol. Blood Marrow Transportation 7:247-256, 2001.

Kern et al., "Target Structures of the CD8* T Cell Response to Human Cytomegalvirus: the 72-Kilodalton Major Intermediate-Early Protein Revisited." J. Virol. 73(10):8179-8184, 1999.

Khan et al., "Comparative Analysis of CD8* T Cell Responses Against Human Cytomegalovirus Proteins pp65 and Immediate Early 1 Shows Similarities in Precursor Frequency, Oligoclonality, and Phenotype." J. Infect. Dis. 185:1025-1034, 2002.

Kleihauer et al., "Ex vivo generation of human cytomegalovirus-specific cytotoxic T cells by peptide-pulsed dendritic cells." Brit. J. Haematol. 113:231-239, 2001.

Klein et al., "Strain-Specific Neutralization of Human Cytomegalovirus Isolates by Human Sera." J Virol. 73:878-886, 1999.

Lacey et al., "Relative Dominance of HLA-B*07 Restricted CD8*T-Lymphocyte Immune Responses to Human Cytomegalovirus pp65 in Persons Sharing HLA-A*02 and HLA-B*07 Alleles." Hum. Immunol. 64:440-452, 2003.

Lang et al., "High Frequency of Human Cytomegalovirus (HCMV)-Specific CD8+ T Cells Detected in a Healthy CMV-Seropositive Donor." Cell Mol. Life Sci. 59:1076-1080, 2002.

La Rosa et al., "Preclinical Development of an Adjuvant-Free Peptide Vaccine With Activity Against CMV pp65 in HLA Transgenic Mice." Blood 100(10):3681-3689, 2002.

Levy et al., "Using Ubiquitin to Follow the Metabolic Fate of a Protein." Proc. Natl. Acad. Sci. USA 93:4907-4912, 1996.

Li et al., "Human Cytomegalovirus Matrix Protein pp150 is Efficiently Presented as One of Target Antigens for Cytotoxic T Lymphocyte Recognition." Chin. Med. J. (Engl.) 110:397-400, 1997.

Liu et al., "Molecular Analysis of the Immune Response to Human Cytomegalovirus Glycoprotein B. I. Mapping of HLA-Restricted Helper T Cell Epitopes on gp93." J. Gen. Virol. 74:2207-2214, 1993.

Liu et al., "Polynucleotide Viral Vaccines: codon optimization and ubiquitin conjugation enhances prophylactic and therapeutic efficacy." Vaccine 20:862-869, 2002.

Longmate et al., "Population Coverage By HLA Class-I Restricted Cytotoxic T-Lymphocyte Epitopes." Immunogenetics 52:165-173, 2001.

Marshall et al., "An Adenovirus Recombinant That Expresses the Human Cytomegalovirus Major Envelope Glycoprotein and Induces Neutralizing Antibodies." J. Infect. Dis. 162:1177-1181, 1990.

Marshall et al., "Antibodies to Recombinant-Derived Glycoprotein B After Natural Human Cytomegalovirus Infection Correlate With Neutralizing Activity." J. Infect. Dis. 165:381-384, 1992.

Marshall et al., "Antibodies to the Major Linear Neutralizing Domains of Cytomegalovirus Glycoprotein B Among Natural Seropositives and CMV Subunit Vaccine Recipients." Virol. Immunol. 13(3):329-341, 2000.

McConkey et al., "Enhanced T-Cell Immunogenicity of Plasmid DNA Vaccines Boosted by Recombinant Modified Vaccinia Virus Ankara in Humans." Nat.Med. 9(6):729-735, 2003.

McLaughlin-Taylor et al., "Identification of the Major Late Human Cytomegalovirus Matrix Protein pp65 as a Target Antigen for CD8* Virus-Specific Cytotoxic T Lymphocytes." J. Med. Virol. 43:103-110, 1994.

Men et al., "Immunization of Rhesus Monkeys With a Recombinant of Modified Vaccinia Virus Ankara Expressing a Truncated Envelope Glycoprotein of Dengue Type 2 Virus Induced Resistance to Dengue Type 2 Virus Challenge." Vaccine 18:3113-3122, 2000.

Meyer et al., "Glycoprotein gp116 of Human Cytomegalovirus Contains Epitopes for Strain-Common and Strain-Specific Antibodies." J. Gen. Virol. 73:2375-2383, 1992.

Morello et al., "Development of a Vaccine Against Murine Cytomegalovirus (MCMV), Consisting of Plasmid DNA and Formalin-Inactivated MCMV, That Provides Long-Term, Complete Protection Against Viral Replication." J. Virol. 76(10):4822-4835, 2002.

Morello et al., "Suppression of murine cytomegalovirus (MCMV) replication with a DNA vaccine encoding MCMV M84 (a homolog of human cytomegalovirus pp65)." J. Virol. 74:3696-3708, 2000.

Moss et al., "Host Range Restricted, Non-Replicating Vaccinia Virus Vectors As Vaccine Candidates." Adv. Exp. Med. Biol. 397:7-13, 1996.

Niethammer et al., "Targeted Interleukin 2 Therapy Enhances Protective Immunity Induced by An Autologous Oral DNA Vaccine Against Murine Melanoma." Cancer Research 61:6178-6184, 2001.

Pande et al., Human Cytomegalovirus Strain Towne pp28 Gene: Sequence Comparison to pp28 of HCMV AD169 and Stable Expression in Chinese Hamster Ovary Cells. Virology 184:762-767, 1991.

Pande et al., "Human Cytomegalovirus Strain Towne pp65 Gene: Nucleotide Sequence and Expression in *Escherichia Coli*". Virology 182:220-228,1991.

Pande et al., "Direct DNA Immunization of Mice With Plasmid DNA Encoding the Tegument Protein pp65 (ppUL83) of Human Cytomegalovirus Induces High Levels of Circulating Antibody to the Encoded Protein." Scand. J. Infect. Dis. Suppl. 99:117-120, 1995.

Pandeet al., "Structural Analysis of a 64-Kda Major Structural Protein of Human Cytomegalovirus (Towne): Identification of a Phosphorylation Site and Comparison to pp65 of HCMV (AD 169)." Virology 178:6-14, 1990.

Papanicolaou et al., "Rapid expansion of cytomegalovirus-specific cytotoxic T lymphocytes by artificial antigen-presenting cells expressing a single HLA allele." Blood 102:2498-2505, 2003.

Pass et al., "A Subunit Cytomegalovirus Vaccine Based on Recombinant Envelope Glycoprotein B and a New Adjuvant." J. Infect. Dis. 180:970-975, 1999.

Prod'Homme et al., "Modulation of HLA-A*0201-Restricted T Cell Responses By Natural Polymorphism in the $HE1_{315-324}$ Epitope of Human Cytomegalovirus." J. Immunol. 170:2030-2036, 2003.

Ramirez et al., "Biology of Attenuated Modified Vaccinia Virus Ankara Recombinant Vector in Mice: Virus Fate and Activation of B- and T-Cell Immune Responses in Comparison With the Western Reserve Strain and Advantages as a Vaccine." J. Virol. 74(2):923-933, 2000.

Ramirez et al., "Attenuated Modified Vaccinia Virus Ankara Can Be Used as an Immunizing Agent Under Conditions of Preexisting Immunity to the Vector." J. Virol. 74(16):7651-7655, 2000.

Rasmussen et al., "Antibody Response to Human Cytomegalovirus Glycoproteins gB and gH After Natural Infection in Humans." J. Infect. Dis. 164:835-842, 1991.

Retiere et al., "Generation of Cytomegatovirus-Specific Human T-Lymphocyte Clones by Using Autologous B-Lymphoblastoid Cells With Stable Expression of pp65 or IE1 Proteins: a Tool to Study the Fine Specificity of the Antiviral Response." J. Virol. 74(9):3948-3952, 2000.

Revello et al., "Human Cytomegalovirus Immediate-Early Messenger RNA in Blood of Pregnant Women With Primary Infection and of Congenitally Infected Newborns." J. Infect. Dis. 184:1078-1081, 2001.

Riddell et al., "Class I MHC-Restricted cytotoxic T Lymphocyte Recognition of cells infected with human cytomegalovirus does not require endogenous viral gene expression." J. Immunol. 146:2795-2804, 1991.

Rock et al., "Degradation of Cell Proteins and the Generation of MHC Class I-Presented Peptides." Annu. Rev. Immunol. 17:739-779, 1999.

Rodriguez et al., "DNA Immunization: Ubiquitination of a Viral Protein Enhances Cytotoxic T-Lymphocyte Induction and Antiviral Protection But Abrogates Antibody Induction." J. Virol. 71(11):8497-8503,1997.

Rodriguez et al., "DNA immunization with minigenes: low frequency of memory cytotoxic T lymphocytes and inefficient antiviral protection are rectified by ubiquitination." J. Virol. 72:5174-5181, 1998.

Rothe et al., "An Antigen Fragment Encompassing the AD2 Domains of Glycoprotein B From Two Different Strains is Sufficient for Differentiation of Primary Vs. Recurrent Human Cytomegalovirus Infection by ELISA." J. Med. Virol. 65:719-729, 2001.

Rowell et al., "Lysosome-associated membrane protein-1-mediated targeting of the HIV-1 envelope protein to an endosomal/lysosomal compartment enhances its presentation to MHC class II-restricted T cells." J. Immunol. 155:1818-1828, 1995.

Roy et al., "Sequence Variation Within Neutralizing Epitopes of the Envelope Glycoprotein B of Human Cytomegalovirus: Comparison of Isolates From Renal Transplant Recipients and AIDS Patient." J. Gen. Virol. 74:2499-2505, 1993.

Ruff et al., "The Enhanced Immune Response to the HIV gp160/LAMP Chimeric Gene Product Targeted to the Lysosome Membrane Protein Trafficking Pathway." J. Biol. Chem. 272:8671-8678, 1997.

Schipper et al., "Minimal Phenotype Panels; A method for achieving maximum population coverage with a minimum of HLA antigens." Human Immunology 51:95-98, 1996.

Seth et al., "Recombinant Modified Vaccinia Virus Ankara-Simian Immunodeficiency Virus Gag-Pol Elicits Cytotoxic T-Lymphocytes in Rhesus Monkeys Detected by a Major Histocompatibility Complex Class I/Peptide Tetramer." Proc. Natl. Acad. Sci. USA 95:10112-10116, 1998.

Seth et al., "Immunization With a Modified Vaccinia Virus Expressing Simian Immunodeficiency Virus (SIV) Gag-Pol Primes for an Anamnestic Gag-Specific Cytotoxic T-Lymphocyte Response and Is Associated With Reduction of Viremia After SIV Challenge," J. Virol. 74(6):2502-2509, 2000.

Sijts et al., "The Role of the Ubiquitin- Proteasome Pathway in MHC Class I Antigen Processing: Implications for Vaccine Design." Curr. Mol. Med. 1:665-676, 2001.

Solache et al., "Identification of Three HLA-A*0201-Restricted Cytotoxic T Cell Epitopes in the Cytomegalovirus Protein pp65 That Are Conserved Between Eight Strains of the Virus[1.]" J. Immunol. 163:5512-5518, 1999.

Spaete et al., "Human Cytomegalovirus Strain Towne Glycoprotein B Is Processed by Proteolytic Cleavage." Virology 167:207-225, 1988.

Spaete et al., "Human Cytomegalovirus Structural Proteins," J. Gen. Virol.75:3287-3308, 1994.

Spaete, "A Recombinant Subunit Vaccine Approach to HCMV Vaccine Development," Transplantation Proceedings 23(3)(3):90-96, 1991.

Stittelaar et al., "Safety of Modified Vaccinia Virus Ankara (MVA) in Immune-Suppressed Macaques." Vaccine 19:3700-3709, 2001.

Sutter et al., "A Recombinant Vector Derived From the Host Range-Restricted and Highly Attenuated MVA Strain of Vaccinia Virus Stimulates Protective Immunity in Mice to Influenza Virus." Vaccine 12(11):1032-1040, 1994.

Sutter et al., "Stable expression of the vaccinia virus K1L gene in rabbit cells complements the host range defect of a vaccinia virus mutant." J. Virol., 68:4109-4116, 1994.

Suzuki et al., "Degradation Signals in the Lysine-Asparagine Sequence Space." EMBO J. 18(21):6017-6026, 1999.

Tobery et al., "Targeting of HIV-1 Antigens for Rapid Intracellular Degradation Enhances Ctyotoxic T Lymphocyte (CTL) Recognition and the Induction of De Novo CTL Responses in Vivo After Immunization." J. Exp. Med. 185(5):909-920, 1997.

Tobery et al., "Cutting Edge: Induction of Enhanced CTL-Dependent Protective Immunity in Vivo by N-End Rule Targeting of a Model Tumor Antigen." J. Immunol. 162:639-642, 1999.

Townsend et al., "Defective Presentation to Class I-Restricted Cytotoxic T Lymphocytes in Vaccinia-Infected Cells Is Overcome by Enhanced Degradation of Antigen." J. Exp. Med. 168:1211-1224, 1988.

Urban et al., "Glycoprotein H of Human Cytomegalovirus is a Major Antigen for the Neutralizing Humoral Immune Response." J. Gen Virol. 77:1537-1547, 1996.

Urban et al., "The Dominant Linear Neutralizing Antibody-Binding Site of Glycoprotein gp86 of Human Cytomegalovirus is Strain Specific," J. Virol. 66(3):1303-1311, 1992.

Utz et al., "Identification of a neutralizing epitope on glycoprotein gp58 of human cytomegalovirus." J Virol. 63:1995-2001, 1989.

Varshavsky et al., "The Ubiquitin System and the N-End Rule Pathway." Biol. Chem. 381:779-789, 2000.

Varshavsky, "The N-End Rule: Functions, Mysteries, Uses." Proc. Natl. Acad. Sci. USA 93:12142-12149, 1996.

Vaz-Santiago et al., "Ex Vivo Stimulation and Expansion of Both CD4* and CD8* T Cells From Peripheral Blood Mononuclear Cells of Human Cytomegalovirus-Seropositive Blood Donors by Using a Soluble Recombinant Chimeric Protein, IE1-pp65." J. Virol. 75(17):7840-7847, 2001.

Velders et al., "Defined Flanking Spacers and Enhanced Proteolysis is Essential for Eradication of Established Tumors by an Epitope String DNA Vaccine," J. Immunol. 166:5366-5373, 2001.

Vidalin, et al., "Targeting of hepatitis C virus core protein for MHC I or MHC II presentation does not enhance induction of immune responses to DNA vaccination." DNA Cell. Biol. 18:611-621, 1999.

Villanueva et al., "Efficiency of MHC class I Antigen Processing: a Quantitative Analysis." Immunity 1:479-489, 1994.

Wells et al., "Structural and Immunological Characterization of Human Cytomegalovirus gp55-116 (gB) Expressed in Insect Cells." J. Gen. Virol. 71:873-880, 1990.

Wills et al., "The Human Cytotoxic T-Lymphocyte (CTL) Response to Cytomegalovirus Is Dominated by Structural Protein pp65: Frequency, Specificity, and T-Cell Receptor Usage of pp65-Specific CTL." J. Virol. 70(11):7569-7579, 1996.

Wolf et al., How MHC Class II Molecules Acquire Peptide Cargo: biosynthesis and trafficking through the endocytic pathway. Annu. Rev. Cell Dev. Biol. 11:267-306, 1995.

Wu et al., "Deoxyribonucleic Acid Vaccines Encoding Antigens with Rapid Proteasome-Dependent Degradation are Highly Efficient Inducers of Cytolytic T Lymphocytes." J. Immunol. 159:6037-6043, 1997.

Wu et al., "Engineering an Intracellular Pathway for Major Histocompatibility Complex Class II Presentation of Antigens." Proc. Natl. Acad. Sci. USA 92:11671-11675, 1995.

Wyatt et al., "Priming and Boosting Immunity to Respiratory Syncytial Virus by Recombinant Replication-Defective Vaccinia Virus MVA." Vaccine 18:392-397, 2000.

Wyatt et al., "Development of a Replication-Deficient Recombinant Vaccinia Virus Vaccine Effective Against Parainfluenza Virus 3 Infection in an Animal Model." Vaccine 14(15):1451-1458, 1996.

Xiang et al., "An Autologous Oral DNA Vaccine Protects Against Murine Melanoma." Proc. Natl. Acad. Sci. USA 97(10):5492-5497, 2000.

Yao et al., "Site-Directed Mutation in a Conserved Kinase Domain of Human Cytomegalovirus With Preservation of Cytotoxic T Lymphocyte Targeting." Vaccine 19:1628-1635, 2001.

Ye et al., "Strong CD8 T-Cell Responses following Coimmunization with Plasmids Expressing the Dominant pp89 and Subdominant M84 Antigens of Murine Cytomegalovirus Correlate with Long-Term Protection against Subsequent Viral Challenge." J Virol. 76:5, 2100-2112, 2002.

Zaia et al., "Status of Cytomegalovirus Prevention and Treatment in 2000." In *Hematology 2000* pp. 339-355.

* cited by examiner

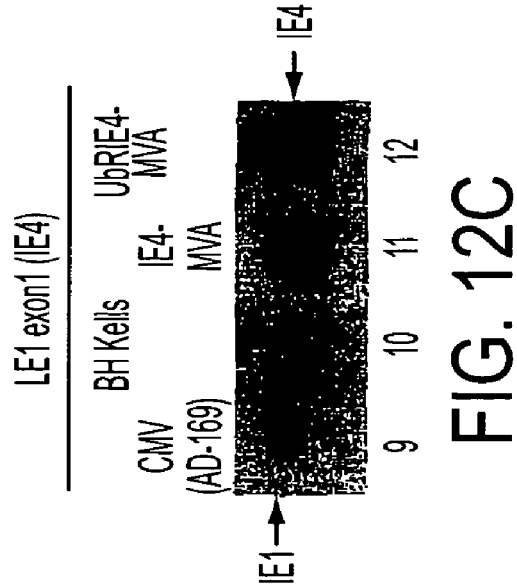
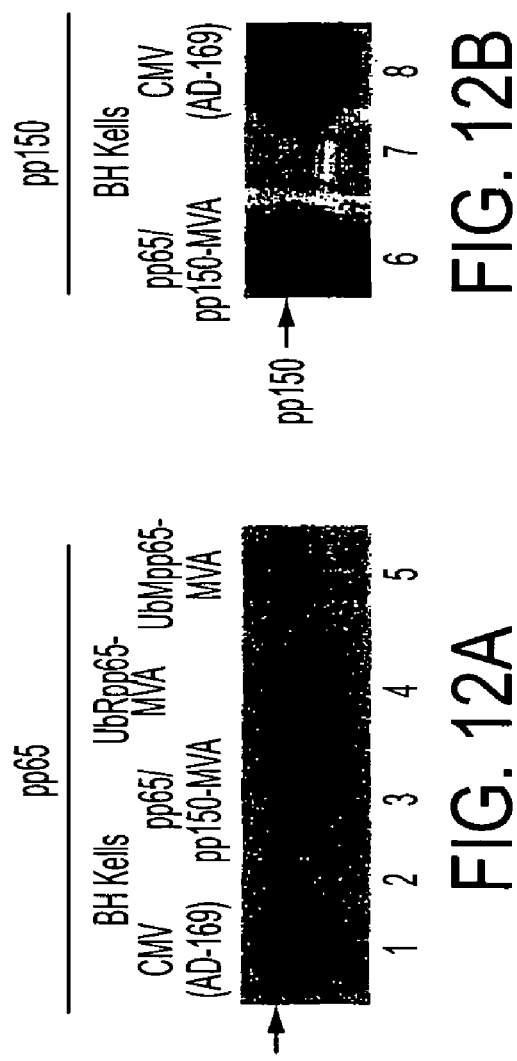
FIG. 12C
FIG. 12B
FIG. 12A

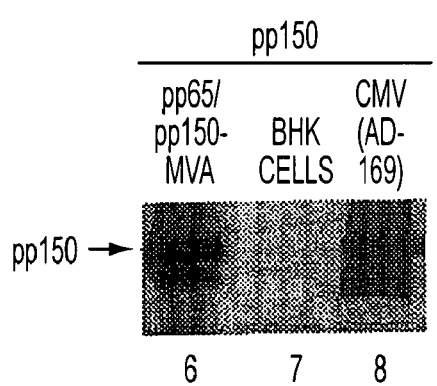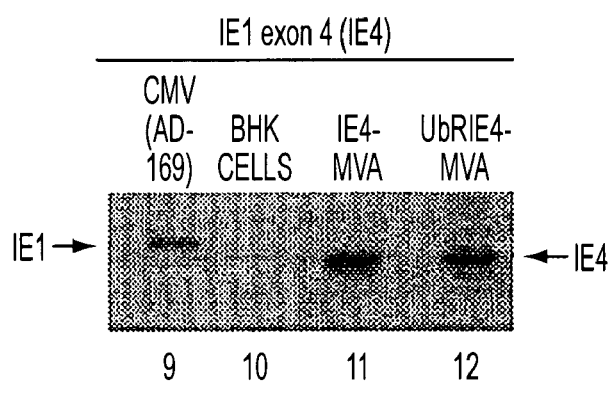
FIG. 14A
FIG. 14B

SEQUENCE LISTING

<160> NUMBER OF SEQ ID NOS: 24

<210> SEQ ID NO 1
<211> LENGTH: 39
<212> TYPE: PRT
<213> ORGANISM: Cytomegalovirus

<400> SEQUENCE: 1

His Gly Ser Gly Ala Trp Leu Leu Pro Val Ser Leu Val Lys Arg Lys
1               5                   10                  15

Thr Thr Leu Ala Pro Asn Thr Gln Thr Ala Ser Phe Arg Ala Leu Ala
            20                  25                  30

Asp Ser Leu Met Gln Arg Ser
        35

<210> SEQ ID NO 2
<211> LENGTH: 25
<212> TYPE: PRT
<213> ORGANISM: Artificial Sequence
<220> FEATURE:
<223> OTHER INFORMATION: fusion of CMV pp65 epitope and PADRE (T help epitope)
<220> FEATURE:
<221> NAME/KEY: MISC_FEATURE
<222> LOCATION: (6)..(6)
<223> OTHER INFORMATION: cyclohexylalanine

<400> SEQUENCE: 2

Lys Ser Ser Ala Lys Xaa Val Ala Ala Trp Thr Leu Lys Ala Ala Ala
1               5                   10                  15

Asn Leu Val Pro Met Val Ala Thr Val
            20                  25

<210> SEQ ID NO 3
<211> LENGTH: 9
<212> TYPE: PRT
<213> ORGANISM: Cytomegalovirus

<400> SEQUENCE: 3

Asn Leu Val Pro Met Val Ala Thr Val
1               5

<210> SEQ ID NO 4
<211> LENGTH: 19
<212> TYPE: DNA
<213> ORGANISM: modified Vaccinia Ankara

<400> SEQUENCE: 4
tgcatttaag gcggatgtc                                            19

<210> SEQ ID NO 5
<211> LENGTH: 19
<212> TYPE: DNA
<213> ORGANISM: modified Vaccinia Ankara

<400> SEQUENCE: 5
tcaatcgcca tttgttcgt                                            19

<210> SEQ ID NO 6
<211> LENGTH: 25
<212> TYPE: DNA
<213> ORGANISM: modified Vaccinia Ankara

<400> SEQUENCE: 6
gtgcgtgtat agagttaaat tcata                                     25

<210> SEQ ID NO 7
<211> LENGTH: 21
<212> TYPE: DNA
<213> ORGANISM: modified Vaccinia Ankara

<400> SEQUENCE: 7
catacataag taccggcatc t                                         21

<210> SEQ ID NO 8
<211> LENGTH: 41
<212> TYPE: DNA
<213> ORGANISM: Homo sapiens

-continued

```
<400> SEQUENCE: 8
cagtcagcta gcgtttaaac atgcagatct tcgtgaagac c                    41

<210> SEQ ID NO 9
<211> LENGTH: 47
<212> TYPE: DNA
<213> ORGANISM: Homo sapiens

<400> SEQUENCE: 9
ggacaacggc gaccgcgcga ctccctaccc ccctcaagc gcaggac                47

<210> SEQ ID NO 10
<211> LENGTH: 47
<212> TYPE: DNA
<213> ORGANISM: Homo sapiens

<400> SEQUENCE: 10
gtcctgcgct tgagggggg tagggagtcg cgcggtcgcc gttgtcc                47

<210> SEQ ID NO 11
<211> LENGTH: 34
<212> TYPE: DNA
<213> ORGANISM: Homo sapiens

<400> SEQUENCE: 11
ccgggtacct caacctcggt gcttttggg cgtc                             34

<210> SEQ ID NO 12
<211> LENGTH: 27
<212> TYPE: DNA
<213> ORGANISM: Cytomegalovirus

<400> SEQUENCE: 12
gcagtcaccg tccttgacac gatggag                                    27

<210> SEQ ID NO 13
<211> LENGTH: 23
<212> TYPE: DNA
<213> ORGANISM: Cytomegalovirus

<400> SEQUENCE: 13
gtgacgtggg atccataaca gta                                        23

<210> SEQ ID NO 14
<211> LENGTH: 46
<212> TYPE: DNA
<213> ORGANISM: Cytomegalovirus

<400> SEQUENCE: 14
agctttgttt aaacgccacc accatggtca aacagattaa ggttcg                46

<210> SEQ ID NO 15
<211> LENGTH: 41
<212> TYPE: DNA
<213> ORGANISM: Cytomegalovirus

<400> SEQUENCE: 15
ttggccgcct ttatttgacg tgggatccat aacagtaact g                    41

<210> SEQ ID NO 16
<211> LENGTH: 33
<212> TYPE: DNA
<213> ORGANISM: Cytomegalovirus
```

```
<400> SEQUENCE: 16
ttgatcgggc ccatacagat cttcgtgaag acc                            33

<210> SEQ ID NO 17
<211> LENGTH: 46
<212> TYPE: DNA
<213> ORGANISM: Cytomegalovirus

<400> SEQUENCE: 17
ctcgaacctt aatctgtttg accctacccc ccctcaagcg caggac              46

<210> SEQ ID NO 18
<211> LENGTH: 46
<212> TYPE: DNA
<213> ORGANISM: Cytomegalovirus

<400> SEQUENCE: 18
gtcctgcgct tgaggggggg tatggtcaaa cagattaagg ttcgag              46

<210> SEQ ID NO 19
<211> LENGTH: 41
<212> TYPE: DNA
<213> ORGANISM: Cytomegalovirus

<400> SEQUENCE: 19
aagaaggcct ggcgcgcctt actggtcagc cttgcttcta g                   41

<210> SEQ ID NO 20
<211> LENGTH: 53
<212> TYPE: DNA
<213> ORGANISM: Cytomegalovirus

<400> SEQUENCE: 20
aaggaaaaaa gcggccgcgc caccaccatg gagtcgcgcg gtcgccgttg tcc      53

<210> SEQ ID NO 21
<211> LENGTH: 40
<212> TYPE: DNA
<213> ORGANISM: Cytomegalovirus

<400> SEQUENCE: 21
aagaaggcct ttatttcacc ctcggtgctt tttgggcgtc                     40

<210> SEQ ID NO 22
<211> LENGTH: 44
<212> TYPE: DNA
<213> ORGANISM: Cytomegalovirus

<400> SEQUENCE: 22
agctttgttt aaacgccacc accatgagtt tgcagtttat cggt                44

<210> SEQ ID NO 23
<211> LENGTH: 41
<212> TYPE: DNA
<213> ORGANISM: Cytomegalovirus

<400> SEQUENCE: 23
aagaaggcct tttatttcac cctcggtgct ttttgggcgt c                   41

<210> SEQ ID NO 24
<211> LENGTH: 19
<212> TYPE: DNA
```

```
<213> ORGANISM: Artificial Sequence
<220> FEATURE:
<223> OTHER INFORMATION: vector pLW22 primer

<400> SEQUENCE: 24
caagcggcct ctgataccc                                                  19
```

HUMAN CYTOMEGALOVIRUS ANTIGENS EXPRESSED IN MVA AND METHODS OF USE

This application claims benefit of prior U.S. provisional application Ser. No. 60/463,026, filed Apr. 16, 2003, the contents of which are hereby incorporated by reference.

STATEMENT REGARDING FEDERALLY SPONSORED RESEARCH

This invention was made with government support in the form of grant nos. CA30206 and CA77544 from the United States Department of Health and Human Services, National Cancer Institute; AI44313 and AI52065 from the United States Department of Health and Human Services (DAIDS) and LS46116-98 (LLS). The government may have certain rights in the invention.

BACKGROUND OF THE INVENTION

1. Technical Field

This invention relates to human cytomegalovirus (CMV), and in particular to methods and compounds for modifying immune responses to CMV in mammals. Specifically, the invention relates to single, tandem multiple and modified CMV proteins which can be expressed in cells using a vector such as an MVA vector or otherwise administered and to methods and compounds for expressing and using these proteins. The compounds of this invention are capable of augmenting immunity to CMV, for example by directing human cytotoxic T lymphocytes (CTL) to recognize and lyse human cells that are infected with CMV. Therefore, vaccines formulated using those compounds also are provided by this invention.

2. Description of the Background Art

The CMV genome is relatively large (about 235 k base pairs) and has the capacity to encode more than two hundred proteins. CMV consists of a nuclear complex of double-stranded DNA surrounded by capsid proteins having structural or enzymatic functions, and an external glycopeptide- and glycolipid-containing membrane envelope. CMV is a member of the herpes virus family and has been associated with a number of clinical syndromes. The major human cellular immune response targets of CMV have been described: pp65, pp150 and IE1. See, for example, U.S. Pat. Nos. 6,133,433 and 6,242,567. Glycoprotein B (gB) also is a CMV target recognized by the humoral immune system.

CMV infection is relatively common and is usually self-limiting in the healthy, immunocompetent child or adult (L. Rasmussen, *Curr. Top. Microbiol. Immunol.* 154:221–254, 1990), however the viral genome is not cleared from the individual and remains in a latent state. CMV persists in this latent state for life, under control and surveillance of cell-mediated immunity against CMV. In addition, approximately 10% of all newborn infants carry CMV. The virus can cause severe congenital disease in the fetus or infant. Some of these newborn infants suffer congenital birth defects. Others carry cytomegalovirus for some time after birth before they show symptoms of disease. CMV is a common cause of mental retardation in children who acquire the infection in utero from mothers carrying an active infection.

Several studies have begun to question whether persistent and apparently asymptomatic CMV infection in an otherwise healthy adult poses health risks in certain individuals. For example, individuals who have undergone coronary angioplasty sometimes subsequently develop restenosis as a result of arterial remodeling. In one study, about one third of such patients with restenosis had detectable CMV DNA in their arterial lesions (E. Speir et al., *Science* 265:391–394 (1994)). In another study, CMV seropositive patients were five times more likely to develop restenosis than their seronegative counterparts (Zhou et al., *New England J. Med.* 335:624–630 (1996)). These studies suggest that decreasing the number of CMV-infected host cells can benefit certain individuals with latent CMV infection, as well as those with an active infection.

CMV is an important consideration in the treatment of patients suffering from Acquired Immunodeficiency Syndrome (AIDS). The defining complication is viral retinitis, which, if left untreated, can lead to blindness. Historically, CMV disease has been one of the more devastating of the opportunistic infections that beset HIV-1-infected individuals. Disease manifestations of CMV viremia which appear as the $CD4^+$ T cell counts drops below $100/mm^3$ include encephalitis, enteritis and pneumonia. At autopsy, there is multi-organ involvement of CMV disease in a great many AIDS patients who suffered from severe CMV retinitis. Patients infected with CMV often suffer impairment of at least some of their vital organs, including the salivary glands, brain, kidney, liver and lungs. Furthermore, CMV is associated with a wide spectrum of classical syndromes including mononucleosis and interstitial pneumonia.

CMV also has an oncogenic potential and a possible association with certain types of malignancies, including Kaposi's sarcoma. Recent studies have shown that CMV antigens are found in association with glioma cells and other brain tumors and with colorectal cancer. Harkins et al., *Lancet* 360(9345): 1557–1563, 2002; Cobbs et al., *Cancer Res.* 62(12): 3347–3350, 2002. CMV therefore may be responsible for part of the malignant transformation process or have some role in the progression of disease.

Since the first use of hematopoietic stem cell transplant as a therapy for hematological malignancies, one of the main infectious complications during the first one hundred days of recovery is pneumonia caused by CMV infection. CMV causes serious opportunistic infection in immunocompromised patients including but not limited to hematopoietic stem cell transplant patients, bone marrow transplant patients, solid organ transplant patients, HIV patients, gestational fetuses, infants and the like. Methods for vaccinating these patients in particular, and certain other individuals such as coronary angioplasty patients and women of child-bearing years, prophylatically or subsequent to infection with CMV to augment the CMV-specific cellular immune response are needed in the art. Strategies both to prevent primary infection and to aid in controlling viremia in patients already carrying CMV are needed, particularly in immunosuppressed or immunocompromised patients.

CMV can cause opportunistic infections which result in a variety of complications, for example immunosuppressed organ transplant patients. Prior to the use of antiviral chemotherapy, CMV infection had been responsible for a substantial proportion of post-bone marrow transplantation complications. Meyers et al., *J. Infect Dis.* 153:478–488, 1986. The use of drugs with substantial anti-CMV activity, such as ganciclovir, has dramatically reduced complications associated with post-bone marrow transplant CMV infections. Schmidt et al., *New England J. Med.* 324:1005–1011, 1991; Goodrich et al., *New England J. Med.* 325:1601–1607, 1991. Ganciclovir is most effective when administered prophylactically before diagnosis of CMV infection. This approach has several negative consequences in patients, however, including neutropenia and increases in fatal bacterial and fungal diseases. Goodrich et al., *Ann. Intern. Med.* 118:173–178, 1993. In addition, because of the acute nature of the potential side-effects of ganciclovir treatment, there is a need for increased hospitalization and growth factor administration to treated patients which, coupled with the cost of ganciclovir prophylaxis, increases the total cost of bone marrow transplant after-care. Other treatments available for CMV disease treatment or prophylaxis, such as Foscarnet, Cidofovir or Valganciclovir, also have been used, but also have significant and potentially dangerous side effects that limit their use. Antiviral drug therapy generally can cause significant morbidity and mortality for some patients.

Because human cytomegalovirus is relatively common, yet is associated with some extremely serious health conditions, a considerable effort has been made to study the biology of the virus with the aims of improving diagnosis of the disease as well as developing preventative and therapeutic strategies. Mounting a $CD8^+$ CTL response is believed to be an important mammalian host response to certain acute viral infections. The observations that CMV infection is widespread and persistent, and can become reactivated and clinically evident in the immunosuppressed patient, suggest that virus-specific CTL are involved both in controlling persistent infection and in recovery from CMV disease.

In bone marrow transplant recipients, protection from the development of CMV disease correlates with the recovery of measurable $CD8^+$ CMV-specific class I MHC-restricted T cell responses. Quinnan et al., *New Eng. J. Med.* 307:7–13, 1982; Reusser et al., *Blood* 78:1373–1380, 1991. These observations led investigators to carry out clinical trials in which donor-derived CMV-specific $CD8^+$ CTL were infused into bone marrow transplant recipients as an alternative to ganciclovir prophylaxis and therapy. Riddell et al., *Science* 257:238–241, 1992. The transfer of $CD8^+$ CTL clones to allogeneic bone marrow transplant recipients resulted in detectable CTL-based CMV immunity, and statistically significant diminution of CMV disease. Walter et al., *New Eng. J. Med.* 333:1038–1044, 1995.

Although successful in application, this approach has the disadvantage that the production of CMV-specific T cells often is problematic. Many culture systems have been developed to generate CMV-specific T cells, such as CMV-infected or retrovirus-infected antigen presenting cells. These antigen presenting cells provide immunodominant CMV antigens, however there is a risk of viral transmission when the cultured T cells are given to severely immunocompromised patients such as bone marrow transplant recipients. Thus, regulatory and safety policies may limit use of virions to stimulate T cells in the clinic.

Other strategies to produce CMV-specific T cells safely include administration of CMV-specific peptide antigens or purified CMV viral protein-pulsed antigen presenting cells, but the high cost and only moderate efficacy of these methods are a concern. To make adoptive immunotherapy treatment widely available to bone marrow transplant patients and other patients, delivery of multiple CMV immunodominant antigens to antigen presenting cells is an important obstacle in the current art to provide expanded CMV-specific T cells in vitro for safe administration to patients. Therefore, a safe, fast and efficient method to prepare CMV-specific T cells for clinical applications have high potential benefits for patients in need of CMV cellular immunity or augmented CMV cellular immunity, such as bone marrow transplant patients.

Another desirable alternative would be to deliver a vaccine derived from CMV that imparts immunity without the need for ex vivo expansion of CMV-specific CTL. No such vaccine presently is available on the market, however. Persons who would benefit from vaccination by compositions according to this invention include, but are not limited to, women of childbearing years, pregnant women, infants, children in a daycare or public school setting, bone marrow transplant recipients and donors, solid organ transplant patients, HIV-positive individuals, coronary angioplasty patients, cancer patients, persons undergoing immunosuppressive therapy or any person at risk for CMV infection or CMV reactivation.

In producing vaccines that are designed to elicit immune response dependent on $CD8^+$ T lymphocytes, it is important to consider that antigens entering the cell through exogenous pathways (pinocytosis, etc.) typically are not processed and presented by Class I MHC molecules. Therefore, methods to introduce proteins directly into the cytoplasm have become one focus of vaccine developers. An approach that has gained favor is to use infection with recombinant vaccinia viruses to deliver and express a large amount of intracellular antigen. The enthusiasm for using vaccinia viruses as vaccines has diminished, however, because these viruses themselves have the potential to cause disease in immunosuppressed people. Another approach to vaccination is to mix antigenic protein with an adjuvant and introduce the mixture under the skin by subcutaneous injection. None of these methods have resulted in production of a clinically useful vaccine to this point. Accordingly, in spite of significant efforts towards identifying the CMV proteins that are recognized by CTL and lead to cellular immunity against the virus, improved methods of preventing and treating CMV infection are needed.

The purpose of (live) viral vaccination is to induce both helper and cytotoxic immunity, which leads to a prolonged and durable memory response against the virus. In the 1970s, Plotkin and co-workers established an attenuated strain of CMV, referred to as Towne, as a proposed therapeutic vaccine. Plotkin et al., *J. Infect. Dis.* 159:860–865, 1989; Plotkin et al., *Ann. Intern. Med.* 114:525–531, 1991. Concerns about using live virus, however, have prevented its use generally. In addition, the effectiveness of Towne at preventing CMV transmission has been questioned. Adler et al., *J. Infect. Dis.* 171:26–32, 1995. Potentially more problematic for an approach using attenuated CMV as a vaccine is the possibility of acquiring infection with a new CMV strain even while having a pre-existing immunity to a different strain. Boppana et al., *N. Engl. J. Med.* 344: 1366–1371, 2001.

Alternative live viral approaches for CMV vaccines have focused on canarypox expressing glycoprotein B (gB) or pp65. Gonczol and Plotkin, *Curr. Top. Microbiol. Immunol.* 154:255–274, 1990; Adler et al., *J. Infect. Dis.* 180:843–846, 1999; Berencsi et al., *J. Infect. Dis.* 183:1171–1179, 2001; Spaete et al., *Virology* 167:207–225, 1988. These methods have not been successful at eliciting both humoral and cellular immunity to CMV. Studies with poxvirus expressing gB and purified gB also did not reveal any additional benefit. Bernstein et al., *J. Infect. Dis.* 185:686–690, 2002. The only gB vaccine with any clinical efficacy is a purified gB protein vaccine, however no published information had demonstrated CMV protection. Pass et al., *J. Infect. Dis.* 180: 970–975, 1999. Some DNA vaccine vectors expressing either gB or pp65 have been evaluated in animal models. Endresz et al., *Vaccine* 19:3972–3980, 2001; Endresz et al., *Vaccine* 17:50–58, 1999; Pande et al., *Scand. J. Infect. Dis.*

Suppl. 99:117–120, 1995. Thus, although there has been some progress in achieving a clinically useful CMV vaccine, a clear-cut strategy in which both cellular and humoral responses are stimulated from a single vector or other modality has been elusive. Therefore, a comprehensive and multifunctional CMV vaccine or other method is needed in the art, particularly a method to augment CMV immunity in the immunocompromised patient and to prevent reactivation of CMV disease.

SUMMARY OF THE INVENTION

Accordingly, this invention is directed to a DNA construct which comprises DNA encoding one or more human cytomegalovirus proteins selected from the group consisting of pp65, pp150, IE1, gB and antigenic fragments thereof, wherein each of the human cytomegalovirus proteins individually optionally is modified by N-terminal ubiquitination, N-end modification or both, and wherein the human cytomegalovirus protein or fragment thereof optionally contains a lysine-containing adapter sequence. Proteins encoded by this construct and vaccine virus vectors that can express this construct also form part of this invention. Additional embodiments of this invention also include methods of vaccinating or augmenting immunity against HCMV.

BRIEF DESCRIPTION OF THE DRAWING

FIG. 12 is a series of western blots showing expression of IE1(4) (FIG. 12A), pp65 (FIG. 12B) and pp150 (FIG. 12C), all expressed from a recombinant MVA.

FIG. 14 shows western blots of pp150 (A) and TE1 exon 4 (B) expressed by pp65/pp150-MVA, IE4-MVA and Ub-R-IE4-MVA. Lane 6=pp65/pp150-MVA infected BHK-21 cells; lanes 7, 10=uninfected BHK cells; lanes 8, 9=AD-169 CMV cells; lane 11=IE4-MVA infected BHK-21 cells; lane 21=Ub-R-IE4-MVA infected BHK-21 cells.

DETAILED DESCRIPTION OF THE PREFERRED EMBODIMENTS

Figure 1:
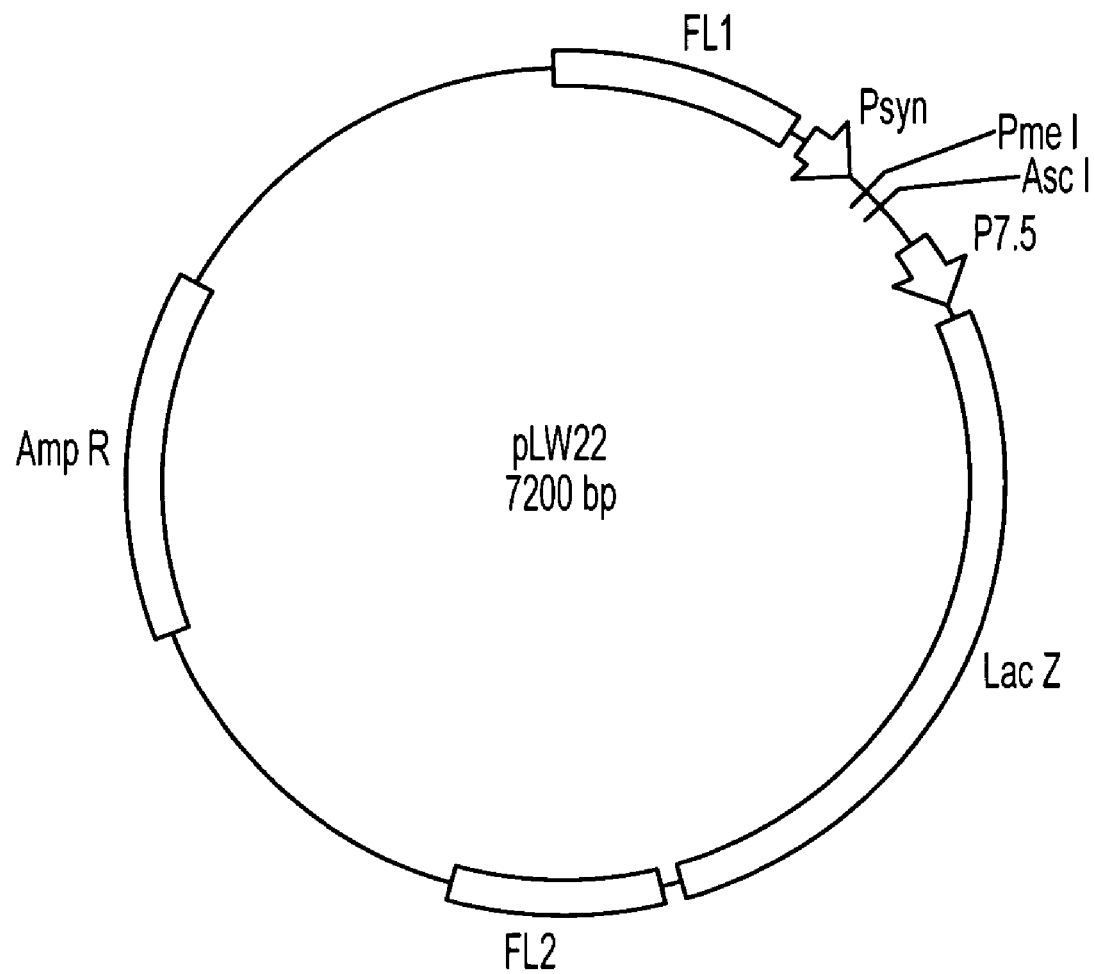
FIG. 1 is a schematic representation of pLW22 insertion plasmid, showing flanking regions FL1 and Fl2, lacZ gene and cloning sites PmeI and AscI. $P_{SYN}$ promoter drives expression of the gene inserted between PmeI and AscI.

This invention relates to DNA and protein constructs that are useful as vaccines to be used prophylactically or in persons already exposed to or infected with CMV. Uses for these constructs include methods for augmenting immune responses to CMV, vaccinating against CMV, diagnosing CMV, producing activated T cells that recognize CMV and producing antigen presenting cells that present CMV epitopes. Vaccines, activated T cells and antigen presenting cells also form part of the invention, including recombinant vaccines such as vaccinia virus or Modified Vaccinia Ankara vaccines that express CMV proteins, fragments thereof and modifications thereof. Ubiquitinated CMV proteins specifically are contemplated.

Stimulation of $T_H$ lymphocytes is known to be essential in mounting a vigorous CMV-specific CTL response. Furthermore, in an immunotherapeutic setting, rapid loss of adoptively transferred CMV-specific CTL in some patients (and a poor clinical outcome) is linked to low CD4 $T_H$ function in bone marrow transplant patients. The vaccines of the present invention preferably are designed to cause both Class I and Class II processing of the antigen(s), which results in the production of both $T_H$ and CTL epitopes, by using CMV proteins that possess a full complement of $T_H$ and CTL epitopes.

The humoral response to pp65, pp150 and IE1 proteins is strong, however there is no evidence that the antibodies produced in response to these antigens neutralize CMV. CMV neutralizing antibodies have been characterized from glycoprotein B (gB), and to a lesser extent, gH. Utz et al., *J. Virol*. 63:1995–2001, 1989; Gonczol et al., *Vaccine* 8:1320–136, 1990; Marshall et al., *J. Infect. Dis*. 165: 381–384, 1992; Rasmussen et al., *Proc. Natl. Acad. Sci. USA* 81:876–880, 1984. The majority of the neutralizing antibody response has been to gB. Britt et al., *J. Virol*. 64:1079–1085, 1990; Banks et al., *J. Gen. Virol*. 70(pt 3):979–985, 1989; Marshall et al., *J. Infect. Dis*. 162:1177–1181, 1990; Rothe et al., *J. Med. Virol*. 65:719–729, 2001. However, different methods described in the prior art of immunizing using gB expressed by poxvirus have been relatively ineffective without booster vaccinations of attenuated Towne strain CMV. Adler et al., *J. Infect. Dis*. 180:843–846, 1999; Bernstein et al., *J. Infect. Dis*. 185:686–690, 2002; Hanke et al., *J. Virol*. 73:7524–7532, 1999; Ourmanov et al., *J. Virol*. 74:2740–2751, 2000. DNA vaccine studies suggest that truncated gB lacking a transmembrane region (gB(s); Carlson et al., Virology 239:198–205, 1997) is more effective at eliciting neutralizing antibodies than gB containing the transmembrane region. Therefore, the constructs of the invention may comprise gB proteins lacking a transmembrane region. Persons of skill in molecular biology are capable of constructing many different DNA constructs to express gB which is truncated or contains a deletion mutation, for example, so that the protein does not become embedded in the cell membrane. Such constructs and proteins are contemplated for use with the this invention, however the native sequence, or any sequence containing one or more desired antigens may be used.

The compounds of this invention preferably involve constructs designed to express one or more full-length or multi-epitope portions of CMV proteins in cells, for the reason that such proteins contain multiple epitopes which are able to induce both humoral and CTL responses in diverse human populations. Full-length proteins therefore are contemplated for use with the invention. However, any antigenic fragment of the protein which contains sufficient material for immune modification also may be used. Fragment, therefore, as used in this application, refers to any portion of a CMV protein that remains antigenic. Antigenicity of a protein or fragment thereof can be determined using an in vitro screen analogous to that described in Example 24 for Ub-R-pp65, or by any known method. The term "antigen fragment" therefore includes, but is not limited to, CTL epitope peptides from the protein, or any portion of the protein that contains one or more such known CTL epitope peptide. Each antigenic protein or fragment may be expressed from an individual expression vector, or multiple antigenic sequences may be expressed from a single expression vector.

It is preferable to inactivate any biological activity in an antigenic protein if there is any risk, however small, of a potential clinical risk when the protein is expressed in vivo. The protein kinase activity associated with pp65, which mimics some cellular kinases, preferably is not present in the expressed protein of the constructs of this invention. Several regions of pp65 have sequences that correspond to protein kinase catalytic domains. One of these seems to be critical for in vitro phospho-transfer. Yao et al., *Vaccine* 19:1628–1635, 2001. A point mutation at amino acid 436, converting the native lysine to asparagine, obliterates protein kinase activity but does not alter immunologic recognition. This mutated protein (pp65(K436N)) therefore is preferred, however the native sequence may be used and has posed no health problems when expressed in ALVAC in short term studies in CMV-negative volunteers. Berencsi et al., *J. Infect. Dis*. 183:1171–1179, 2001. Skilled technicians are able to mutate pp65 or other proteins in any suitable manner to reduce or remove undesired activity, for example cellular kinase activity. Such mutated, truncated or altered proteins (modified proteins) therefore may be used in the invention.

IE1 protein also contains important biologic regulatory activity, including trans-activation of various cellular promoters. Kim et al., *J. Gen. Virol.* 80(pt 4):961–969, 1999; Johnson et al., *J. Gen Virol.* 80(pt 5):1293-1303, 1999; Pajovic et al., *Mol. Cell. Biol.* 17:6459–6464, 1997. To minimize the risk of transcription stimulation from IE1, 85 amino acids coding exons 2 and 3 preferably are deleted from the expressed protein. Deletion of these two coding exons results in a 406 amino acid protein that is no longer nucleus-associated and remains in the cytoplasm. Gyulai et al., *J. Infect. Dis.* 181:1537–1546, 2000. This protein has minimal transactivation activity, but since most of the known CTL epitopes are located in exon 4, the cellular immune recognition is not altered in any important way. Those of skill in the art can readily engineer similar mutated or deleted IE1 proteins using methods known in the art to produce proteins that lack transactivation activity, for example IE1 exon 4 (IE1(4)) or other sequences. The native sequence also may be used.

To improve efficiency of cellular immune recognition of CMV antigens, CMV pp65, pp150, gB and IE1 antigens preferably are modified at the N-terminus with monomeric ubiquitin, together with an optional substitution of the native N-terminal amino acid, methionine, with arginine. These are termed Ub-R (arginine) and Ub-M (methionine) modifications.

The importance of efficient proteasomal processing to the development of cellular immune responses is exemplified by findings in several systems that vaccines composed of processed CTL epitopes are recognized more efficiently than those generated by full-length proteins. Since processed immunologic epitopes are an important means for the cellular immune system to recognize virally infected cells, a vaccination method designed to increase their generation would result in a better vaccine function. Varshavsky and collaborators have engineered modified proteins to affect protein stability by taking advantage of the ubiquitin degradation system. Varshavsky et al., *Biol. Chem.* 381:779–789, 2000. A ubiquitin gene is incorporated into the construct to be expressed at the amino terminus of the target protein. Using the N-end rule, the amino terminal residue of the target protein is changed from methionine (a stabilizing amino acid) to arginine (the most destabilizing amino acid). See Varshavsky, *Proc. Natl. Acad. Sci. USA* 93:12142–12149, 1996; Levy et al., *Proc. Natl. Acad. Sci. USA* 93:4907–4912, 1996, the disclosures of which are hereby incorporated by reference. The most destablizing N-end rule amino acid is arginine, however others may be used. Alternatively, lysosomal-associated membrane protein 1 (LAMP1) cytoplasmic tail sequences may be linked to the antigen to enhance presentation as described in Wu et al., *Proc. Natl. Acad. Sci. USA* 92:11671, 1995; Lin et al., *Cancer Res.* 56:21, 1996, Bonini et al., *J. Immunol.* 166(8): 5250–5257, 2001.

A lysine-containing adapter sequence also may be engineered adjacent to and upstream from the designated first codon of the target antigenic protein to ensure proper function of the ubiquitin system, if desired. Suzuki and Varshavsky, *EMBO J.* 18:6017–6026, 1999. The lysine adapter sequence is derived from a prokaryotic regulatory region and contains multiple sites that allow engagement of the ubiquitin complex. This sequence contains a lysine residue that can serve as a substrate for linkage with a multi-Ub chain, which is the initial step in the protein degradation process. The above linker structure is known as a N-degron, and generally is fused to an antigen at its amino terminus. Rock and Goldberg, *Annu. Rev. Immunol.* 17:739–779, 1999; Townsend et al., *J. Exp. Med.* 168: 1211–1224, 1988. If a protein naturally contains a targetable lysine residue, then the lysine adapter sequence may not be necessary.

The recombinant virus may be made by inserting a single CMV protein-encoding gene or multiple CMV protein-encoding genes, for example 2, 3, or 4 genes, into a poxvirus such as Vac or MVA via homologous recombination. Genes such as gB, pp65, pp150 and IE1 and fragments and modifications thereof are particularly useful. Vectors preferably are designed to target the deletion regions of MVA since these are dispensable for virus growth on chicken embryo fibroblast (CEF) and BHK cells. This may be accomplished by including flanking regions of the deletions into the targeting plasmids to provide a homologous region for recombination.

MVA is a live attenuated viral vector that can easily accommodate multiple foreign genes and has several attractive properties. Hanke et al., Vaccine 20:1995–1998, 2002. Due to lack of viral assembly and avirulence in mammals, MVA is safe for use in immunosuppressed patients. Stittelaar et al., Vaccine 19:3700–3709, 2001. It also is capable of producing recombinant proteins and inducing potent immune responses in non-permissive hosts. See Moss, Proc. Natl. Acad. Sci. USA 93:11341–11348; 1996; Belyakov et al., Proc. Natl. Acad. Sci. USA 100:9458–9463, 2003.

Either rvac or rMVA, used in vitro to stimulate PBMC from seropositive volunteers, elicited remarkable numbers of CMV T-cells in 7–12 days. Simultaneous in vitro expansion of both pp65-and IE1 were used as stimulators. In addition, HHDII transgenic mice immunized with rMVA consistently showed a strong and specific primary CMV cytotoxic response. These findings indicate that rMVA is useful for adoptive immunotherapy in the transplant setting or as a CMV vaccine candidate.

Figure 2:
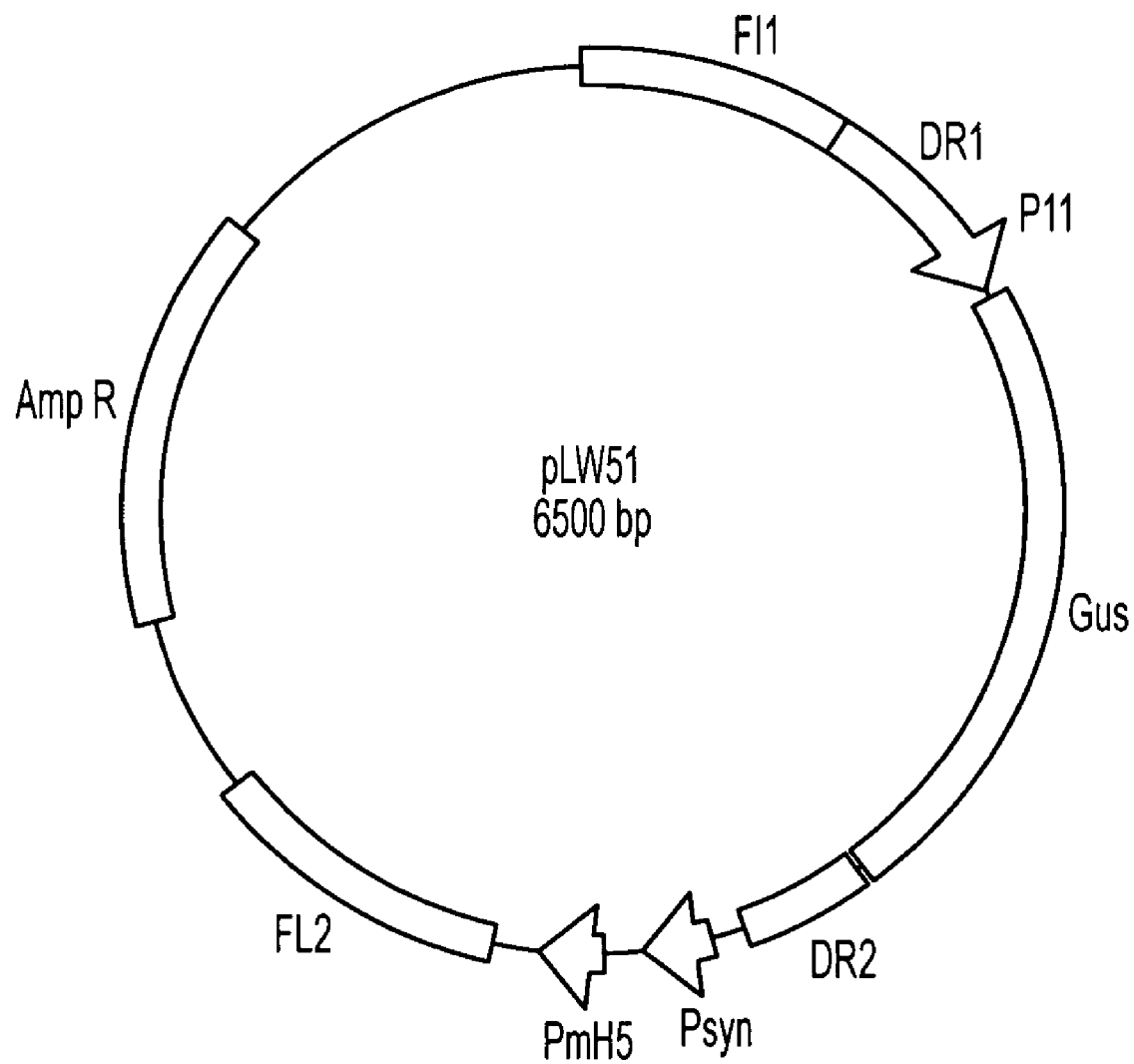
FIG. 2 is a schematic representation of the pLW51 insertion plasmid, showing flanking regions FL1 and FL2, direct repeats DR1 and DR2 and Gus gene. The plasmid also contains two multiple cloning sites MCS1 and MCS2 (not labeled). The $P_{SYN}$ promoter drives expression of the gene inserted into MCS1 and the $P_{mH5}$ promoter drives the expression of the gene inserted into MCS2.

Two deletion regions referred to as delII and delIII may be used effectively to insert foreign genes by homologous recombination into MVA. Meyer et al., *J. Gen. Virol.* 72(pt 5):1031–1038, 1991. This can be done in two stages using two plasmid insertion vectors, however those of skill in the art can devise different methods to insert the desired genes into Vac or MVA. Preferably, the first stage involves putting a gene or modification thereof, for example an Immediate Early gene 1 (IE1) protein, such as exon 4 (IE1(4)) into deletion II of MVA using the pLW22 insertion plasmid. See FIG. 1. CMV phosphoprotein 65 (pp65) and phosphoprotein 150 (pp150) genes can be inserted simultaneously into deletion III of the recombinant IE1(4)-MVA using the pLW51 insertion plasmid with dual viral promoters to generate pp65/pp150/IE1(4)-rMVA. See FIG. 2. Of course, these methods can be used to insert any combination of any desired CMV-antigenic-material-encoding DNA into MVA, in any desired order.

The completed recombinant (in this example pp65/pp150/IE1(4)-rMVA) preferably is characterized by western blot, immunostain, and or PCR analyses before initial expansion. The final product preferably is analyzed by performing testing for its identity, purity, potency, and stability, for example as required by federal Food and Drug Administration regulations.

To obtain a good level of foreign protein expression, a synthetic ($p_{SYN}$E/L) promoter combining early and late vaccinia gene expression elements is suitable for use in MVA. Chakrabarti et al., *BioTechniques* 23:1094–1097, 1997. This promoter powerfully transcribes foreign inserts in delII and delIII regions, including pp65, pp150 and IE1 exon 4. This promoter was not effective to stably express gB, possibly because some membrane glycoproteins overexpressed by $p_{SYN}$E/L can disrupt production of MVA. Therefore, if $p_{SYN}$E/L is not effective, an intermediate strength or weaker promoter such as $p_{H5}$E/L or $p_{7.5}$E/L may be used. For example, the modified H5 promoter ($P_{H5}$E/L) allowed strong expression of gB(s) and also allowed for expansion of the virus to usable titers ($10^{9-10^{10}}$/ml). Those of skill in the art are aware, however, of many suitable promoters which can be used to good effect with this invention and can be adapted to the methods, depending on the needs of the system.

Figure 3:
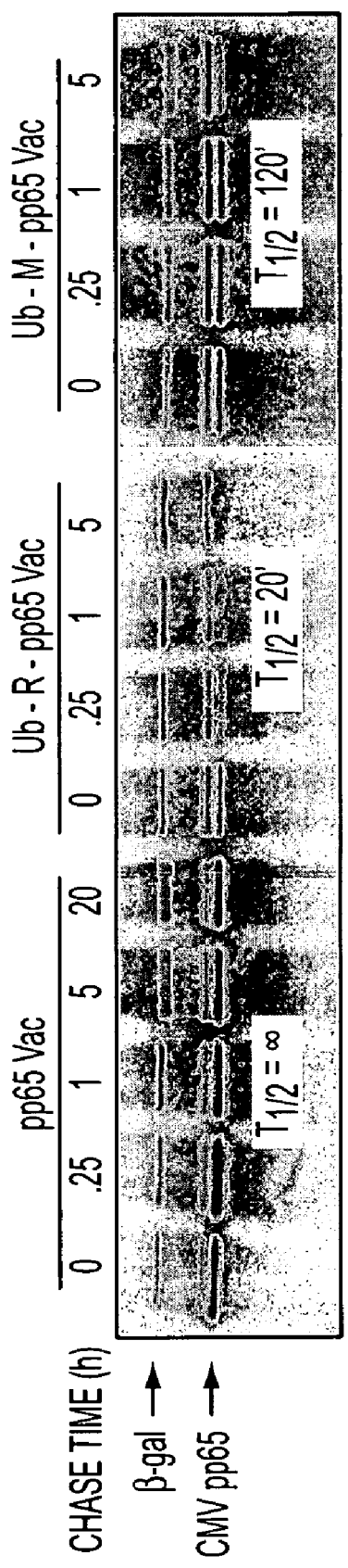
FIG. 3 is a western blot with results of a pulse-chase experiment showing the half-life of pp65, Ub-R-pp65 and Ub-M-pp65 expressed in human TK⁻ cells using Vac constructs.

Expression of these modified forms of CMV-pp65 was evaluated using western blot and by pulse-chase analysis to distinguish any changes in the half-life of the protein. FIG. 3 shows the results of pulse-chase analysis of three forms of CMV pp65 protein as indicated. See also Examples. Human TK− cells were infected with Vac for 1 hour in met/cys-free medium in the presence of $^{35}$S-labeled met/cys. Unlabeled met/cys was added for the indicated chase time. Compared to unmodified pp65, Ub-R expression product showed a dramatically reduced half-life in the cell (about 20 minutes), indicating much more rapid degradation. Similar studies were conducted with modified forms of both IE and pp150 antigens, with substantially similar results (data not shown).

Poxviruses such a vaccinia virus (Vac) or modified Vaccinia Ankara (MVA) can be used in generating and expanding CMV-specific T cells to deliver single or multiple CMV antigens to antigen presenting cells. A serious obstacle to using replication competent Vac strains for clinical application is their strong immunogenicity. Moss et al., *Adv. Exp. Med Biol*. 397:7–13, 1996, Hirsch et al., *J. Virol*. 70:3741–3752, 1996. Even one immunization without prior exposure to the virus can result in severe viremia in the immunocompromised patient. In addition, the strong immunogenicity of Vac abrogates the effect of subsequent booster vaccinations in immunocompetent individuals.

MVA has a very good safety record for human use, a large foreign gene capacity, and is relatively cheap to produce. MVA is an attenuated poxvirus derived from the highly virulent Ankara strain by 570 passages in chicken embryo fibroblasts, which has lost about 30 kb of its genome and its ability to reproduce in mammalian cells. MVA has been used successfully in Europe as a safer alternative to the traditional smallpox vaccine in 120,000 high-risk individuals, including children and the elderly, and therefore is preferred for use with the invention, both for safety reasons and for reasons of effectiveness in delivering antigens to humans.

MVA's good safety record is due to its inability to replicate in mammalian cells and its avirulence in humans. Lack of viral assembly and avirulence in mammals makes it suitable for use in immunocompromised patients. Unlike other attenuated poxviruses, the block in viral assembly does not interfere with its ability to produce abundant recombinant proteins under the control of strong promoters in non-permissive hosts. Multiple sites of insert integration allow the flexibility to include full length CMV proteins, immunologic epitopes or cytokines. MVA is especially suited to programs in which a booster immunization is desired because it has lost genes which cause inflammation in mammalian hosts and its attenuated infectivity does not interfere with robust expression of foreign genes.

Expression of recombinant proteins by MVA is unimpaired compared to non-attenuated strains, even at high levels of expression, because the block of MVA reproduction in human cells occurs late in virus assembly, after viral DNA replication. Several vaccines based on the MVA vector have been developed for influenza, malaria, SIV and HIV. MVA vaccines also have shown efficient priming of both cellular and humoral immunity and protection from diseases in well-known animal models.

CMV antigen constructs preferably are engineered with amino-terminal ubiquitin, a lysine-rich adapter sequence ($e^K$) and replacement of initiator methionine with arginine to enhance processing of each antigen. The lysine-rich adaptor is not required, particularly with pp65, IE1 and pp150, which contain internal lysine residues, but can be used to enhance degradation in these proteins as well as those which do not contain such native lysine residues. More rapid degradation in the cell has important implications for vaccines intended to generate enhanced CTL immunity.

Neutralizing antibodies are desirable to prevent virus infection. A neutralizing antibody response therefore is important to prevent congenital infection of a gestational fetus. The main viral protein that causes a neutralizing response is glycoprotein B (gB). Neutralizing epitopes located in this antigenic protein can prevent infection of mammalian cells by a wide variety of CMV strains. Therefore, incorporation of gB or a modification or fragment thereof into the compositions of this invention is preferred, particularly for vaccines administered for prophylactic purposes to prevent new infections. Because vaccines and constructs containing gB or a gB gene product are intended to produce a humoral response, ubiquitin modification, which would encourage Class II processing, preferably is absent for gB antigens.

To ensure potent cell-mediated immunity, both cytotoxic and helper T cells must be stimulated, however targeting CMV proteins to the Class I pathway of degradation may diminish helper T cell responses. Therefore, if a particular vaccine results in an imbalance of T cell responses favoring too greatly stimulation of Class I restricted CTL (which may be short-lived without CD4 T help), an alternative modification of one or more of the CMV antigens using lysosomal targeting may be used in accordance with this invention. LAMP-1 modification of CMV pp65 enables enhanced stimulation of memory CD4 T cells in human peripheral blood mononuclear cells in CMV seropositive individuals. Bonini et al., *J. Immunol*. 166(8): 5250–5257, 2001. Therefore, the constructs and compositions according to this invention may be optionally modified by adding an additional antigen or substituting an antigen that is targeted for Class II mediated degradation in this manner. Additionally, using unmodified forms of one or more antigen can avoid potential emphasis on the Class I pathway by vaccine products.

Mutated proteins which are contemplated for expression by the constructs and methods of the invention may include those with point, deletion or insertion mutations, truncation or any mutation that does not eliminate the antigenic recognition of the protein. Such mutated proteins or DNAs are referred to in this application also as "modified" proteins or DNA constructs. Therefore, modified DNAs, modified proteins and modifications generally may include any mutation as described above, as well as modifications by addition of sequences, such as ubiquitination or LAMP-1 modification, or other modifications such as, for example, N-end modification. Modifications also may include, in particular, deletion of transmembrane regions, deletions or other mutations that decrease or eliminate undesired activities in a protein or DNA molecule or use of only portions of a protein that contain desired antigens, such as exon 4 of IE1.

The described CMV antigens and fragments and modifications thereof can be expressed in an adenovirus, a retrovirus, including lentiviruses, or any known viral transfer agent, but preferably in a pox virus such as Vac, Modified Vaccinia Ankara (MVA), Canary Pox, Modified Vaccinia Virus Lister or others. Antigens can be expressed alone or in combination with one, two, three or more additional antigens in any of these viruses. Any combination of pp65, pp150, IE1 and gB or any modification or fragment thereof can be expressed in any order. Combinations of antigens may be expressed all from the same recombinant virus or, alternatively, in two or more virus constructs.

pLW22 plasmid insertion vector for making recombinant MVA has three relevant components: (1) MVA flanking regions of deletion II, named F11 and F12, allowing it to insert into the deletion II region of MVA via homologous recombination; (2) an expression cassette which includes $P_{SYN}$, a strong synthetic vaccinia promoter to drive foreign gene expression, and the restriction enzyme cloning sites PmeI and AscI for insertion of genes of interest; and (3) a color screening marker gene, lacZ, under the control of the $P_{7.5}$ vaccinia promoter for color selection and screening of recombinant MVAs. See FIG. 1. The pLW22 shuttle vector supports the expression of one marker gene and one antigen sequence. Detection of recombinant virus advantageously may be accomplished using an incorporated bacterial marker gene, for example (lacZ) β-galactosidase or (GUS) β-glucuronidase.

The recently developed plasmid insertion vector pLW51 has the following four features: (1) MVA flanking regions of deletion III that allow it to insert into the deletion III region of MVA via homologous recombination; (2) a color screening marker gene, β-glucuronidase (gus), under control of a vaccinia promoter called $P_{11}$; (3) two direct repeats composed of MVA sequence (designated as DR1 and DR2) flanking the gus screening marker gene to allow the gus gene to be removed from recombinant MVA; and (4) two vaccinia promoters ($P_{SYN}II$ and $P_{mH5}$) and two multiple cloning sites, permitting the insertion of two separate foreign genes under the control of the $P_{SYN}II$ and $P_{mH5}$ promoters. The first multiple cloning site is behind an early/late $P_{SYN}$ promoter, while the second multiple cloning site uses an early/late $P_{mH5}$ promoter. pLW51 may be modified to include a PmeI and an AscI site in the second multiple cloning site to facilitate the cloning of CMV genes. We included the PmeI and an AscI sites in the pLW51 derived vector used in these studies, and we continue to refer to our vector which includes the PmeI/AscI modification as pLW51. See FIG. 2.

In addition, vectors incorporating the xanthine-guanine phosphoribosyltransferase (gpt) gene may be used as described by Moss and collaborators. Vectors incorporating the gpt gene are a means to eliminate bacterial marker genes and to provide a quicker means to purify recombinants. Wyatt et al., *Vaccine* 14:1451–1458, 1996; Falkner and Moss, *J. Virol.* 64:3108–3111, 1990. Live immunostaining can detect CEF cells that contain rMVA expressing the gpt gene. The gpt selection method results in wild-type-free rMVA faster than color screening because there is suppression of wild type virus at each purification round. MPA (mycophenolic acid) is used as the selection agent in the presence of xanthine and hypoxanthine as described for standard vaccinia strains according to the methods described in Falkner and Moss, *J. Virol.* 62:1849–1854, 1988, the disclosures of which are hereby incorporated by reference. This methodology is an alternative to color screening that is compatible with other bacterial markers which may be incorporated into rMVA in accordance with this invention.

There are existing vectors with transient gpt expression which can be used to insert foreign genes into delIII, allowing independent manipulation of both the tk and delII sites for additional foreign gene insertions, either with or without accompanying bacterial marker genes according to any convenient method known in the art.

For color screening, the initial step in creating a recombinant poxvirus by homologous recombination is to simultaneously transfect/infect permissive cells with a transfer vector containing the foreign insert gene flanked by poxvirus genomic sequences, together with wild type MVA into a permissive cell line such as CEF.

Multi-antigen MVAs are constructed either with multiple genes expressed from a single shuttle plasmid utilizing multiple promoters and inserted in a single deletion site, or multiple shuttle plasmids are inserted in more than one deletion site. Either approach is equally suitable. For construction of a multi-antigen CMV-MVA with transient bacterial marker gene expression, the following vectors may be used to insert the genes into MVA using established homologous recombination methods. Moss et al., in Coligan et al., (Eds.) Current Protocols in Immunology. New York, Greene Publishing, 1998, pp. 16.15.1–16.21.9. Bacterial gene markers are used to make isolation of the recombinant virus easier, however in some instances, viral or DNA vectors that express bacterial gene products as tracking markers cause potent immune stimulation because the bacterial gene products may overwhelm the viral immunity which is intended to be stimulated. Riddell et al., *Nat. Med.* 2:219–223, 1996; Berger et al., *J. Virol.* 75:799–808, 2001. A vector system using transient marker stabilization (TMS) results in a final virus in which the bacterial markers are deleted. Scheiflinger et al., *Arch. Virol.* 143:467–474, 1998. The transfer plasmid vector pLW51 inserts into delIII of MVA and contains two early/late promoters (mH5 and $P_{SYN}II$) for expression of two foreign genes. See FIG. 2.

Construction may be begun by inserting a CMV-antigen-encoding sequence, for example gB(s), under the control of mH5 and a different CMV-antigen-encoding sequence, for example Ub-R-pp65, expressed via $P_{SYN}II$ in pLW51. Initial screening can be done with a GUS marker. The GUS marker is deleted in the final recombinant virus because it is flanked on either side by direct repeats. This creates a recombinant virus that does not contain bacterial protein genes. Therefore, in the first screening one can use a color substrate to distinguish colored plaques from those which have not recombined the bacterial marker gene. In subsequent rounds of screening, the screening gene is absent. A different method of screening is therefore needed, such as a PCR or antibody staining method to detect the virus with the recombined foreign gene. To complete the virus, a vector targeting delII may be used to insert a third CMV-antigen-encoding sequence, for example IE1 exon 4, under the control of $p_{SYN}E/L$ and screened for LacZ expression using a convenient substrate, for example the Bluo-gal™ (Sigma) substrate.

Figure 4:
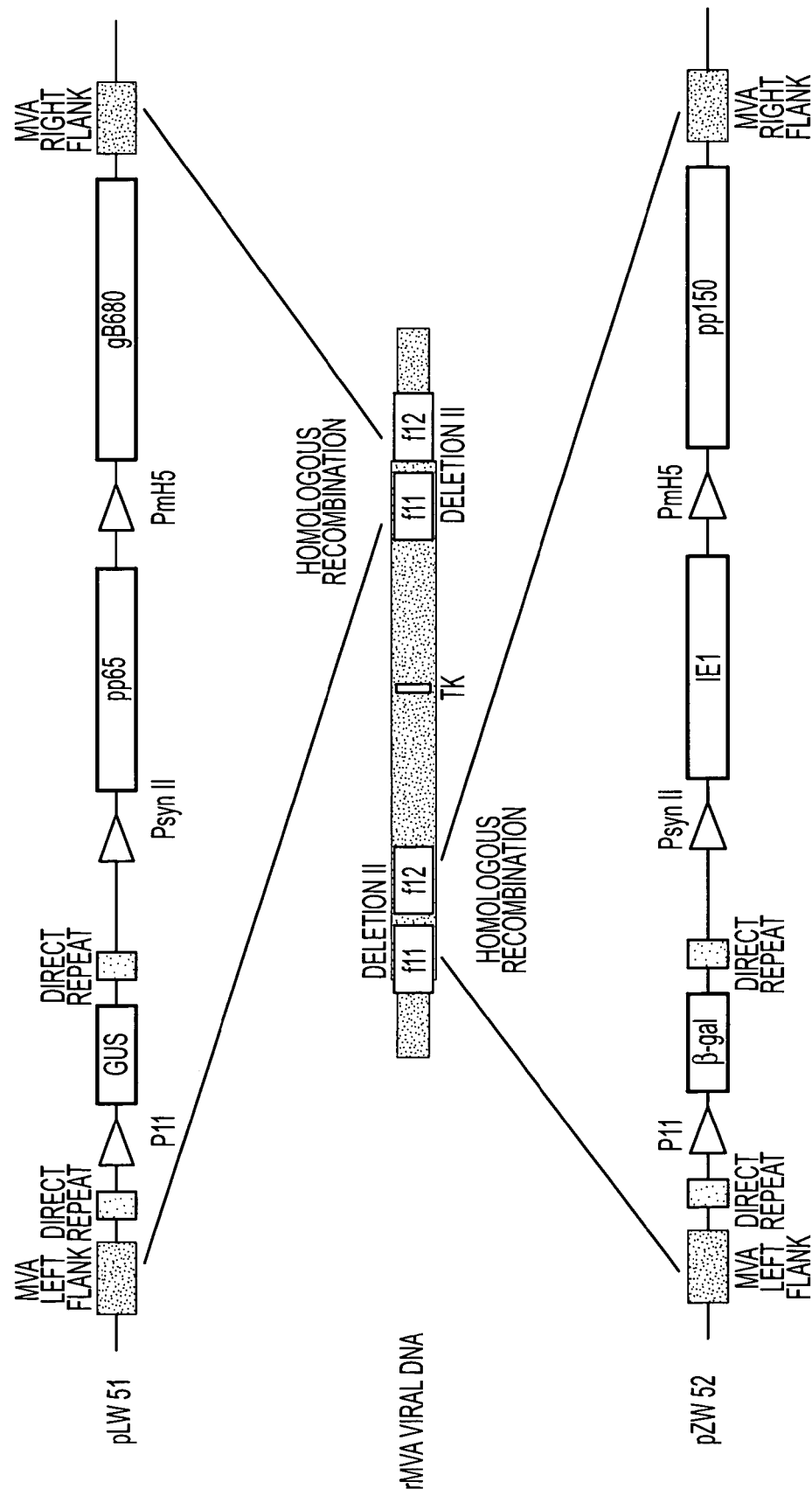
FIG. 4 is a schematic representation showing an example of rMVA viral DNA insertions of pLW51 plasmid carrying a pp65 antigenic sequence and a gB(s) (termed gB680 in the Figure) antigenic sequence and a potential plasmid (pZW52) carrying an IE antigenic sequence and a pp150 antigenic sequence.

A companion vector to pLW51 (pZW52) that targets delII may be used with transient expression of LacZ for screening purposes. See FIG. 4, which presents an example of rMVA construction. It is understood that the proteins pp65, gB680 (gB(s)), IE1 and pp150 depicted in this figure represent the native sequence or any fragment or modification thereof. This vector has dual promoters to allow expression of two genes, for example IE1 exon 4 and pp150. pZW52 expressing one or two genes may be introduced by homologous recombination into MVA already expressing two genes, as described above and shown in FIG. 4. The final vector then can be purified as is convenient, for example first using a color screen for LacZ expression, then additional rounds of screening by immunostaining or PCR. The final rMVA preferably is analyzed by PCR for detection of wild type virus because PCR is more sensitive than immunostaining methods. Construction of pZW52 is designed to carry all features of pLW51 and target del II site of MVA. Therefore Flanking region 1 and 2 (FL1 and FL2) for targeting del III site of MVA is replaced with Flanking region 1 and 2, which are designed to target del II site of MVA.

These methods may be used to create rMVA containing any desired combination of CMV antigens, including 1, 2, 3, 4, 5 or more separate genes. These genes may be the native CMV genes or modified CMV genes, for example Ub-R or Ub-M forms of the genes, truncated genes, mutated genes or any combination thereof, with or without additional sequences added for enhanced performance, such as an $e^K$ sequence, or for convenience such as a bacterial marker gene or the like. The contents of a few exemplary but non-limiting rMVA constructs that are contemplated as part of the invention are provided in Table I, below.

TABLE I

Expressed CMV Antigens of
Exemplary rMVA Construct(s).

1. Ub-R-pp65, Ub-R-pp150, Ub-R-IE(4), gB(s)
2. gB(s), IE, Ub-R-pp65(K436N), gH, Ub-R-pp150
3. Ub-M-pp150, gB, IE1(4), pp65(K436N)
4. IE1(4), gB(s), pp65
5. Ub-M-pp65, gB(s)
6. Ub-R-pp65(K436N)
7. Ub-R-pp65, pp150, IE1(4), gB(s)
8. Ub-R-pp65, gB(s) and IE1(4)
9. pp150 and gB(s)

BHK cells provide a convenient way to screen for rMVA because they are a continuously dividing transformed cell line. BHK-21 is the only mammalian cell line permissive for infection of MVA, and these cells allow efficient propagation of MVA to titers exceeding $10^{10}$/ml. They cannot be used to detect recombinant virus using immunostain without acetone-methanol fixation, which inactivates the virus. Therefore, an alternative method is to use primary CEF, which may be passaged up to two times. These cells adhere to plastic tissue culture dishes in the presence of concanavalin A without fixation. CEF cells are commercially available, for example from Charles River Laboratories, and can be stored in monolayers for several weeks at 31° C. in a 5% $CO_2$ incubator. Moreover, CEF are acceptable by the FDA-CBER for vaccine production, unlike BHK cells. Suitable medium for CEF cells is BME containing penicillin/streptomycin, 1% fetal calf serum and 4% newborn calf serum. All serum preferably is tested to be free of bovine spongiform encephalitis and other adventitious agents.

When using pLW51, about 40–50 foci may be pulled from the first several selection rounds for screening to insure a correct recombinant, after which 5–10 may be pulled each subsequent round. After each round of selection on pLW51 recombinants, either immunostaining or immunofluorescence preferably is performed on each plug to make sure that the plug is expressing the necessary inserted gene(s). This typically is needed only in the first several rounds, but can be repeated throughout the entire screening, if desired. When using pLW22, about 5–10 foci may be pulled each round, and immunostaining between each round is not required because pLW22 does not contain direct repeat sequences. It is preferable to go through 8 to 10 rounds of screening before the initial expansions and to check for wild type MVA.

Western Blot analysis, or any other convenient method, advantageously is performed to test rMVA-infected cells for the expression of the inserted CMV proteins. For example, western blot analysis may be performed as described below. Those of skill in the art are aware of many different variations and modifications to these types of methods, therefore any of these known modifications are contemplated as useful with this invention.

A 100 mm tissue culture dish of 80–90% confluent CEF cells is infected with the rMVA at an MOI of approximately 0.01 or any MOI suitable for the assay conditions. Virus-infected cells are harvested, for example, 24 hours post infection, and cell pellets are resuspended in buffer for cell lysis. Controls may include lysates of uninfected CEF cells, wild type MVA-infected CEF cells, and/or CMV-infected cells. Samples may be run on a 10% SDS-PAGE gel and transferred onto a membrane, for example an Immuno-Blot PVDF Membrane (Bio-Rad) using a Mini-blot system (Bio-Rad) or any convenient method known in the art. The transferred PVDF membrane advantageously may be blotted with 5% non-fat dry milk overnight at 4° C. to reduce non-specific background, and then blotted with primary monoclonal antibodies against each specific CMV protein (for example pp65, pp150, gB and/or IE1(4)) under suitable conditions, for example at room temperature for two hours. After washing, diluted labeled secondary antibody, for example goat anti-mouse antibody conjugated with peroxidase diluted in PBS (1:5000), may be added to the membrane. The protein bands thus are visualized on film using chemiluminescent detection reagents provided in an ECL kit (Amersham Pharmacia) or by any convenient known method.

Immunostaining preferably is performed during the screening process to confirm that the rMVAs being selected are expressing the desired CMV proteins, as follows or by any suitable method. The viral plugs may be diluted in MEM-2 and used to infect three wells of a 12-well tissue culture dish of CEF cells. Several candidate viral plugs may be screened simultaneously, if desired. The following day, the virus-infected cells may be fixed and stained using, for example, the peroxidase conjugated mouse IgG VECTASTAIN ABC Kit and DAB Peroxidase Substrate kit (Vector Laboratories, Inc., CA). The same primary antibodies to be used in the western blot analysis may be used for convenience. Following addition of the substrate, each well is examined for stained foci, which represent protein-positive viruses. Only those viral plugs that stain positively for the CMV proteins should be chosen to continue the screening process.

At the end of 8–10 rounds of selection, the virus advantageously is checked for the presence of wild type MVA contamination (in the first stage) or contamination by rMVA containing less than all the inserted CMV antigens (in the second and subsequent stages) before making large-scale expansions. To do this, a portion of the virus plug pulled from the final round of selection may be diluted and used to infect a 100 mm tissue culture dish of CEF cells. The cells may be harvested after cytopathic effect is evident over the entire plate (usually 48 hours). A standard DNA extraction, phenol/chloroform extraction, and ethanol precipitation is convenient perform on, for example, 50 µl of the cell lysate. DNA from the selectant conveniently is dissolved in buffer, for example 10 mM Tris-EDTA, and 1 µl may be used in a PCR reaction.

Suitable PCR primers may be designed outside of the flanking regions of MVA to detect the absence of insertions in the virus (indicating wild-type virus). For deletion II inserts, the forward primer 5'-TGCATTTAAGGCGGAT-GTC-3' (SEQ ID NO:4) and reverse primer 5'-TCAATCGC-CATTTGTTCGT-3' (SEQ ID NO:5) are suitable and convenient. For deletion III inserts, the forward primer 5'-GTGCGTGTATAGAGTTAAATTCATA-3' (SEQ ID NO:6) and reverse primer 5'-CATACATAAGTACCG-GCATCT-3' (SEQ ID NO:7) are suitable and convenient. Standard PCR conditions, which can be used here, may include 1 cycle of 95° C. for 5 minutes, and 35 cycles of 95° C. for 1 minute, 55° C. for 1 minute, and 72° C. for 1 minute.

The presence of unmodified wild type MVA sequence in delII will result in a 500 bp PCR product using the above primer sets, whereas the insertion of the sequence containing the inserted antigen in rMVA will have a much larger fragment (>6 kb), which usually is difficult to amplify in standard PCR conditions and therefore not detected. Similarly, the presence of rMVA containing no insert at delIII in the second stage will generate a 919 bp PCR product, whereas the insertion of pLW51 sequences to create, for example, pp65/pp150/IE1(4)-rMVA, results in a 9 kb fragment, which also is not detectable using standard PCR conditions. The PCR samples may be run on a 1% agarose gel and analyzed to determine if additional screenings will be necessary to remove any remaining wild-type virus.

After PCR has confirmed that the rMVA is free from parental virus contamination, the expansion process may be started. Expansion of the virus suitably may be accomplished in several stages. The remainder of the plug from the final round of selection may be used to infect a single well of a 6-well tissue culture dish of CEF cells. After cytopathic effect is evident, the cells may be harvested and subjected to three cycles of freezing, thawing, and sonication to release the virus. The process may be repeated, using half of the viral lysate from the 6-well plate to infect a 100 mm dish of CEF. After cytopathic effect is apparent, the cells may be harvested and subjected to three cycles of freezing, thawing, and sonication to release the virus. This viral lysate may be used conveniently as the initial expansion stock. A large-scale expansion then may be performed. Half of the initial expansion may be used to infect ten 150 mm tissue culture dishes of CEF cells. The cells may be harvested when CPE is apparent over the entire dish, and the cells may be subjected to three freezing/thawing/sonication cycles to release the virus. This viral lysate may be used conveniently as the permanent expansion stock, from which all other expansions can be made. See below for a more detailed description. Lysates conveniently are labeled and stored at –80° C.

Titration of complete rMVA containing inserts of the desired CMV antigens, for example pp65/pp150/IE1(4)-rMVA, on CEF cells may be performed as follows or using any convenient known method. Serial dilutions of the pp65/pp150/IE1(4)-MVA may be set up in MEM-2. A six-well tissue culture dish of CEF may be infected in duplicate with a 1 ml dilution series of $10^{-7}$, $10^{-8}$, and $10^{-9}$ for two hours at 37° C. MEM-10 (Minimum Eagles Medium containing 10% fetal calf serum) may be used to bring the total volume up to 5 ml per well for incubation at 37° C. On the following day, the cells may be fixed and stained using, for example, the peroxidase conjugated rabbit IgG VECTASTAIN ABC Kit and DAB Peroxidase Substrate kit (Vector Laboratories, Inc., CA). The primary antibody can be a polyclonal antibody to vaccinia virus, generated in a rabbit host (Biogenesis Inc.) or any suitable monoclonal or polyclonal antibody or binding fragment thereof. Following addition of the substrate, each well can be examined for stained foci, which represent infectious units. The titer then can be then calculated as infectious units/ml.

Live virus detection can be accomplished conveniently using any known methods, for example, peroxidase-conjugated secondary antibodies followed by reaction with substrate. Live virus can be harvested from colored foci, and, following three freeze-thaw cycles, replated on fresh CEF monolayers for further purification. Cytoplasmic proteins can be detected if the cell membrane is cracked with a 90 minute incubation at –20° C. followed by immunostaining according to conventional methods. To pick a virus that expresses the targeted CMV genes, it is convenient to choose 10 primary foci, replate in three separate 6-well dishes with a titration between $10^{-1}$ and $10^{-6}$ dilution and detect virus using three different methods. One dish is fixed and stained for the bacterial marker, another fixed and immunostained and the third live-immunostained. If the majority of foci express the CMV protein but are not stained by a bacterial marker substrate, they likely have deleted the bacterial gene. Further rounds of screening preferably are performed, until wild type MVA is not detectable, by comparing immunostain with anti-vaccinia antibody (for example, by Biogenesis) to immunostain with CMV specific antibody (for example, anti-gB(s) antibody) to achieve a one-to-one correspondence of foci in different dishes. After screening, the virus is ready for scale-up for use in expression testing and immunizations.

In preparation for virus purification, 25–40 150 mm tissue cultures of CEF cells can be grown to 80–90% confluency. The dishes may be infected with the recombinant MVA and harvested with a cell scraper when cytopathic effect is visible over the entire dish. The cells from all dishes advantageously are pooled together and lysed, for example using a Dounce™ homogenizer with tight pestle. The virus then may be sonicated on ice three times, and cell debris removed by centrifugation at a low speed. The viral supernatant may be further purified by layering onto a 36% sucrose cushion and spinning at 32,000×g (Surespin™ 630 rotor, Sorvall) for 1 hour in an ultracentrifuge or by any convenient method. The viral pellet preferably is washed one or more times. The final viral pellet then may be resuspended in 1 to 4 ml of 1 mM Tris-HCl, pH 9.0, or 1×PBS containing 5% lactose or any suitable buffer or solution.

A suitable method for amplifying rMVA is as follows. The final screened virus, with confirmed absence of wild type MVA, may be amplified on CEF cells according to known methods, including sequential amplification using a 35 mm dish, a 100 mm dish, and then 30–40 150 mm dishes. The virus may be harvested from the dishes after observation of cytopathic effect. The cell pellet from the 30–40 plates then may be diluted in a suitable buffer, for example 14.0 ml 10 mM Tris-HCl, pH 9.0, and homogenized in a glass Dounce™ mortar with a tight (A) pestle until all cells are broken. The homogenate then may be disrupted using a cup sonicator, then the lysate pooled, clarified at low speed (1600×g) and layered over a 36% sucrose cushion (15 ml). After sedimentation for 60 minutes at 32,000×g in a Sorvall Surespin™ 630 swinging bucket rotor, the pellet may be resuspended in PBS or 10 mM Tris-HCl, pH 9.0, sonicated and distributed in cryovials for long-term storage. The viral stock can be titered using an immunostaining procedure. Generally, about $10^{10}$ plaque-forming units or more are produced from a single preparation.

To confirm that the foreign gene insert(s) are being properly expressed in multi-antigen rMVA, protein expression studies preferably are carried out using western blot. Each of the expressed CMV antigens can be detected either in the native conformation or after denaturation in SDS using several different available antibodies as described by Sanchez et al., *J. Virol.* 74:975–986, 2000 (for example, IE1, P63–67; pp65, 28–19; pp150, 36–34; gB, 58–15). Approximately $10^7$ CEF (permissive), Epstein-Barr virus transformed human B lymphocyte cell line (EBVLCL, non-permissive) or mouse cell line (P815, non-permissive) are infected with CMV-MVA at an appropriate MOI between 1 and 50, overnight. Use of permissive and non-permissive lines is important because expression levels will vary depending on the ability of MVA to propagate. The purpose of these studies is to confirm that expression levels of co-expressed CMV antigens have not been altered when incorporated into MVA expressing the other CMV antigens, in modified or unmodified form. Adherent cells are infected in 100 mm dishes and suspension cells are infected in 15 ml conical tubes. For western blot analysis, cells are scraped from monolayers or harvested from suspension culture. After extensive washing, they are lysed in protein lysis buffer containing protease inhibitors PMSF and aprotinin. Aliquots of either nuclear or cytoplasmic fractions are subjected to electrophoresis on polyacrylamide gels of an appropriate percentage using a Mini-Protean™ gel system (BiORad Laboratories). The separated proteins are transferred to PVDF membranes using a commercially available transfer apparatus. The membranes are blocked overnight and then incubated with primary antibody against the appropriate CMV protein. Exposure on film may be performed by enhanced chemiluminescence fluorography in the presence of light-emitting substrate that reacts with secondary antibody modified with horseradish peroxidase.

Commonly used human antigen presenting cells such as EBVLCL can be infected with the vaccine for testing to determine if CMV antigen-specific T cell clones from humans who have been infected with CMV are able to lyse cells expressing the rMVA vaccine. Such testing was performed for an rMVA vaccine according to the invention and is presented in Example 11. The results show that the vaccine effectively causes expression of CMV antigens in human antigen presenting cells that are recognized by human CMV-specific T cell clones, and indicates that the vaccine and the method is effective to produce an immune response to CMV in humans. CTL clones that are specific for pp65, pp150 and IE1 are available. Longmate et al., *Immunogenetics* 52:165–173, 2001. Standard chromium release assays are conveniently used to evaluate CTL lysis at a range of effector:target ratios.

An additional test of immune recognition of antigens expressed by CMV-MVA constructs is an infectious stimulation assay of peripheral blood mononuclear cells followed by a quantitating effector function assay such as cytolysis or lymphoproliferation. This type of test provides an evaluation of T cell memory responses, which are highly desirable in the therapeutic setting, particularly if an immunocompetent transplant donor is the individual being immunized or if the CMV-MVA is used in an in vitro method to produce and expand T cells for adoptive transfer of immunity. The assay may be performed according to the methods described below or any convenient method known in the art.

EBVLCL are infected with the CMV-rMVA to be tested. Separate aliquots of cells may be infected with different rMVA constructs for comparative purposes. Infections generally are performed at an MOI of about 5 for 2 hours in 2% fetal calf serum EBVLCL culture medium. The cells are irradiated (5000 rads). About 20 million fresh Ficoll-separated peripheral blood mononuclear cells are incubated with saturating concentrations of purified mouse anti-human CD4, CD16 and CD56 monoclonal antibodies, such as are available commercially from PharMingen. A labeled or bead-conjugated anti-mouse antibody, for example Dynabead™ goat anti-mouse immunoglobulin G (Dynal AS, Oslo, Norway) may be used for removal of bound cells. The resulting population of cells is more than 80% $CD8^+$ as determined by flow cytometry. LaRosa et al., *Blood* 97:1776–1786, 2001. It is convenient to use a half million of these depleted peripheral blood mononuclear cells as effectors, together with $4 \times 10^5$ CMV-MVA infected/irradiated EBVLCL antigen presenting cells and $2.5 \times 10^6$ autologous γ-irradiated (2400 rads) peripheral blood mononuclear cells as feeder cells. These in vitro stimulation (IVS) cultures may be analyzed after about 7–12 days, both for CMV-specific cytotoxic response (by, for example, chromium release assay) and binding to CMV-specific HLA tetramer reagents. For cytolysis, autologous EBVLCL are convenient to use for targets, pulsed with 10 μM of the relevant CMV peptide or an equal concentration of an unrelated synthetic control sequence and labeled with $Na^{51}CrO_4^-$. Background lysis by Vac and/or EBV-specific CTL is reduced by cold target inhibition as described. Lubaki et al., *AIDS Res. Hum. Retroviruses* 10:1427–1431, 1994. Preferably, experimental determinations are performed in triplicate and assay data is considered acceptable if spontaneous release is less than 30%.

Counting CMV-specific T cells using HLA tetramers provides dramatic evidence that recombinant-virus-expressed antigens, including ubiquitinated antigens, elicit memory T cells. This assay combined with intra-cellular cytokine (ICC) assays, which detect a cytokine, for example IFN-γ, after peptide stimulation is even more reliable as a functional assay.

Flow cytometric methods allow multiple parameters to be evaluated at once using different fluorochromes. T cells can be evaluated for defined phenotypes based on well-known cell-surface markers such as CCR7, $CD45RO^+$ or $CD62L^{low}$, for example. IFN-γ is a convenient $T_H1$ cytokine to measure as an indicator of T help. Companion aliquots from chromium release assays after stimulation by cells expressing CMV antigens from recombinant virus for 7–12 days may be incubated with HLA tetramers and stained for intracellular IFN-γ with a specific anti-cytokine antibody. Peripheral blood mononuclear cells also may be stained for phenotype markers in conjunction with ICC for IFN-γ: anti-CD4 in combination with either anti-CD62L or CD69 antibodies for analysis of memory CD4 T cells and anti-CD8 in combination with either anti-CD62L or anti-CD69 antibodies for memory $CD8^+$ T cells.

Stained samples and controls may be analyzed by any convenient method, for example using a FACSCalibur® instrument equipped with two lasers using CellQuest" software (Becton Dickinson). This equipment is capable of simultaneous detection of 4 colors. The data can indicate whether CMV-specific, IFN-γ secreting cells are amplified in response to the recombinant virus, whether they express the CD4 or CD8 surface markers and whether they possess an effector or memory phenotype.

For lymphoproliferation studies, irradiated autologous and HLA-mismatched EBVLCL may be infected for about 12–24 hours with either CMV-specific or control virus, followed by incubation with fresh peripheral blood mononuclear cells from healthy donors. After co-incubation (generally about 2–3 days, with the last 6–12 hours including $^3$H-thymidine in the medium), the cells are assayed for ³H-thymidine incorporation. Preferably, only human AB⁺ serum from CMV-seronegative donors is used in this assay. Since many patients and donors have been given smallpox vaccine, it is important to have controls using MVA without foreign genes to rule out vector-specific stimulation of lymphocyte proliferation.

Immunization of mice has proven of value in translating results to the study of vaccination against human clinical infectious disease. The transgenic mouse model correlates well to human in vivo responses and is accepted in the art to provide useful indication of success in humans. Previous studies with a Balb/c mouse model on antibody elicitation by proteinaceous gB or gB expressed from either naked DNA or poxvirus have been performed. Endresz et al., *Vaccine* 19:3972–3980, 2001; Britt et al., *J. Infect. Dis.* 171:18–25, 1995; Berencsi et al., *J. Gen. Virol.* 74(pt 11): 2507–2512, 1993. MVA vaccines can be evaluated in Balb/c mice or in transgenic HLA A2.1/Kb mice, another well-recognized mouse model known to correlate with clinical results in humans. Preferably, however, validation of effective processing of a vaccine is performed in more than one haplotype (for example HLA All or HLA B7.2) because HLA A2.1 is carried by less than 50% of people in many ethnic groups.

HHDII mice are a combined knockout/transgenic line in which the beta-2 microglobulin gene and the H-2D$^b$ Class II gene are deleted. This effectively prevents development of most murine-specific T cell responses. Inserted into these double knockout mice is a transgene referred to as HHD described in Pascolo et al., *J. Exp. Med.* 185(12): 2043–2051, 1997, the disclosures of which are hereby incorporated by reference. The transgene is composed of the alpha1/alpha2 domains of the HLA A2.1 gene, genetically engineered to the alpha 3 domain from the murine K$^b$ molecule, which is connected to the human beta-2 microglobulin gene. This transgene, therefore, allows the mice to develop immune responses that are restricted by expression of human HLA A2.1. HHDII mice can be used in place of HLA transgenic mice because the deletion of the H-2 Class I genes causes a more robust HLA-restricted response and hence a more sensitive detection of recognition.

Evaluation of CMV-specific human CTL responses may be performed in HLA-A2.1/Kb transgenic mice, as follows. The mice are injected with the vaccine preparation. A booster may be given 12–30 days later if desired. Multiple boosters may be given to achieve greater durability of immune response. About one week after the final immunization, splenocytes are prepared from the spleens of immunized mice and cultured. Lipopolysaccharide (LPS) blasts for in vitro stimulation of the immunized cells may be prepared aseptically from suspensions of unimmunized mouse spleen cells ($1.0-1.5 \times 10^6$ cells/mL) by addition of 25 µg/mL LPS and 7 µg/mL dextran sulfate. These cells are loaded with the same CTL epitope peptide as was used to immunize the transgenic mice to create antigen-presenting cells. These antigen-presenting cells are used to stimulate the cultured splenocytes from the immunized transgenic mice in vitro, approximately 12–14 days after the final immunization. A second in vitro stimulation, or further in vitro stimulations, may be performed, if desired, 5–7 days after the first in vitro stimulation. About a week after the last in vitro stimulation, a chromium release assay may be performed to test the ability of the immunized transgenic splenocytes to specifically recognize and kill either mouse or human target cells loaded with the antigenic peptide of the vaccine.

Mice generally are immunized with about 20–50 million plaque-forming units of virus to achieve a sufficient response. For vaccination of a human individual, a first immunization with $10^8$ plaque-forming units of rMVA is suitable, preferably about $10^6$ to about $10^{10}$ and most preferably about $10^7$ to about $10^9$ plaque-forming units. Booster vaccinations may be given at any desired and suitable interval. Generally, it is preferable to give 1–3 doses of virus in a 4 month period, with boosters containing about 50% of the dose given in the first vaccination to minimize unwanted immune responses against MVA. Practicing physicians and others of skill in the art are aware that the dose given to a particular patient will depend on such factors as age, weight and general health, status of the immune system, etc. Thus, it is considered routine for those of skill to modify the above doses to fit the needs of any particular patient, and such modifications are contemplated to be within the scope of this invention. Routes of administration which may be used and which are appropriate for administration of vaccines are the intraperitoneal, intramuscular, intradermal, subcutaneous or mucosal (e.g. intranasal or rectal) routes. The vaccines of this invention are particularly suited for intramuscular or mucosal (intranasal) administration.

One goal when designing a vaccine for public health purposes is to ensure that at least 80%, preferably at least 90% and most preferably at least 95% of a multi-ethnic population will recognize the antigens in the vaccine and therefore benefit from it. Memory CTL can be detected in fresh peripheral blood from healthy CMV-positive persons who have mounted a successful cellular immune response to CMV using tetramer reagents to confirm recognition of specific antigens in vivo and usefulness of the vaccine antigens.

Whether CMV proteins when expressed from poxvirus vectors would result in development of immunity in transgenic mouse models was investigated using proteins modified with human ubiquitin at the amino terminus. The amino terminal amino acid of the CMV protein also was changed in some cases from the native methionine to an arginine. The stability of pp65 protein was examined using radioactive pulse-chase analysis. Ubiquitin addition to the amino terminus greatly decreased the half life of the protein. Insertion of arginine at its amino terminus further destabilized the protein.

This enhanced degradation generates HLA Class I epitopes after infection of targets more efficiently than unmodified pp65 expressed from vaccinia virus. In addition, Ub-R-pp65Vac infection of targets expressing HLA A*0201, and co-incubation with murine immune splenocytes dramatically increases recognition compared to infection with unmodified pp65Vac. This result shows that the inventive methods result in vaccines producing enhanced CTL immunity.

The immunologic properties of the ubiquitin-modified forms of pp65 were investigated in both in vitro studies with human peripheral blood mononuclear cells (PBMC) and in vivo utilizing well-recognized mouse models of HLA genes, including the human HLA A*0201 and A*1101. Evaluation of pp65 protein ubiquitin expression in poxviruses was tested with cloned CMV-specific human cytotoxic T cells, followed by in vitro stimulation by PBMC from CMV-seropositive adults. In a very short-term (approximately one hour) infection of target cells with the ubiquitin-Arg form of pp65 (Ub-R-pp65) versus unmodified pp65, CTL recognized Ub-R-pp65-infected targets much more efficiently, showing that this enhanced degradation technique increases CTL immunity.

In additional studies, unfractionated populations of human PBMC were stimulated with autologous B cells which had been briefly infected with Ub-R-pp65Vac or unmodified pp65Vac for 2 hours. After stimulation, the reactivity of the PBMC to targets sensitized with peptides derived from CMV-pp65 showed 2–5 times greater recognition when infected with Ub-R-pp65 versus unmodified pp65. Staining of the unfractionated effector population (stimulated by ubiquitinated or unmodified pp65) with an HLA-tetramer reagent specific for $pp65_{495-503}$ (NLVPM-VATV; SEQ ID NO:3) showed that about 10-fold more CMV-specific CTL were produced in the case of Ub-R-pp65 expressed in poxvirus versus unmodified pp65. This indicates that ubiquitin modification accelerates the degradation and recognition of pp65, enhancing vaccine function.

Between 10–50 million pfu of sucrose-gradient purified poxvirus (Vac) expressing Ub-R-pp65 or pp65 was introduced intraperitoneally into mice between 8–11 weeks of age to study immunogenicity in vivo. Two to three weeks post-infection, mice were sacrificed for evaluation of their spleen cell populations. After peptide sensitization, the spleen cells were assayed for ability to lyse human T2 cells which had been sensitized with specific and non-specific peptides. Infection with Ub-R-pp65-expressing poxvirus caused an immune response which recognized peptide-sensitized target cells more strongly by several fold over unmodified pp65-expressing poxvirus. Thus, preclinical data from both mouse and human systems demonstrates that ubiquitin modification favorably alters the immunogenicity of the pp65 protein. Studies with ubiquitinated HIV clade B transcriptase also have demonstrated in mouse models that there is more robust recognition of protein epitopes after immunization with ubiquitinated versus unmodified protein.

Effectiveness of MVA immunogens against human cytomegalovirus also was evaluated as follows. Single antigen recombinant rMVA with cDNA encoding either CMV pp65, pp150, or IE1(4) were constructed by homologous recombination as described above. The inserted genes were under the control of the strong synthetic Early/Late vaccinia promoter and were recombined into deletion regions II or III of MVA. Plaque-pure viruses were isolated with the help of color screening using β-galactosidase (GAL) or β-glucuronidase (GUS) bacterial markers, and verified to be free of wild type virus by use of PCR.

Unmodified full length pp65 was not efficiently recognized by epitope-specific CTL, perhaps due to inefficient processing of the unmodified full-length protein. The apparent difficulty in generating sufficient CTL epitope by antigen presenting cells, which are well-recognized when processed minimal peptide is provided (e.g. $pp65_{495-503}$), necessitated modification of the antigen. Therefore, pp65 was modified into a form with enhanced degradation. Ubiquitination of pp65 coupled with destabilization through the use of an N-terminal Arg residue reduced the half life of the protein to less than 20 minutes, a change of more than fifty-fold. The increased rapidity of degradation is a likely explanation for the enhanced ability of targets which are infected with Ub-R-pp65Vac to present sufficient cognate CTL epitope to be recognized by murine CTL after fusion peptide immunization. In addition, enhanced recognition of target cells infected by Ub-R-pp65Vac versus unmodified pp65 was found after immunization with both HLA A2 or A11 fusion peptide vaccines.

The immunological properties of the ubiquitin-modified forms of pp65 were investigated both in in vitro studies with human peripheral blood mononuclear cells and in vivo in mouse models of HLA genes, including HLA A*0201 and A*1101. The pp65 protein was evaluated using cloned human CMV-specific T cells in which the protein was expressed using pox viruses followed by in vitro stimulation of peripheral blood mononuclear cells from CMV-seropositive adults. The Ub-R form of pp65 was more efficiently recognized than unmodified pp65 by the CTL clone in B cell line targets, as demonstrated using a very short term (about 1 hour) infection of the target cells. In a study testing human peripheral blood monocytes stimulated with autologous B cells infected with either ubiquitin-modified or unmodified pp65 (expressed in pox virus) showed 2 to 5 times greater recognition of the ubiquitin-modified form. Staining of the effector cell population with a pp65 epitope HLA tetramer reagent showed about 10-fold greater amounts of CMV-specific CTL in the group stimulated with cells infected with the ubiquitin-modified form of pp65. Further, human CTL clones of 5 different haplotypes which recognize pp65 lysed targets more efficiently when they were infected with Ub-R-pp65Vac versus unmodified pp65Vac (data not shown). This shows that the ubiquitin modification accelerates both degradation and recognition of pp65 such that vaccine function and augmentation of cellular immune response is enhanced.

The vaccines of the present invention include DNA vaccines, including those encoding pp65, pp150, gB and IE1 and fragments thereof, separately or in combination. These DNA vaccines contain genetic material as described herein for expression in rMVA and may be constructed and administered by any convenient method which is known in the art. DNA vaccines may take the form of a modified pcDNA3 expression plasmid, or any suitable construct known in the art. Immunizations of about 10–20 µg DNA, or more, may be administered, or amounts of about 1–5 mg for human use. Timing of boosters, if desired, may be as discussed for MVA vaccinations as described herein. The DNA constructs and vectors encoding them can be used to produce and expand CMV responsive CTL which may be used for adoptive transfer of immunity.

The experimental results presented here demonstrate the improvement in CTL immunity which can be achieved with accelerated degradation of CMV immunogen afforded by ubiquitination. Without wishing to be bound by theory, it is believed that ubiquitination results in generation of CTL epitopes more quickly and that this, combined with modifying the N-terminal methionine to arginine, allows a bigger memory response to develop. This method therefore provides a surprising increase in CTL immunity, which is useful in preparing vaccines for any use, including for protection of gestational fetuses from CMV disease and protection of HIV-positive persons or other immunocompromised individuals from an important opportunistic infection.

EXAMPLES

Example 1

Recombinant Vaccinia Virus Constructs

Figure 5:
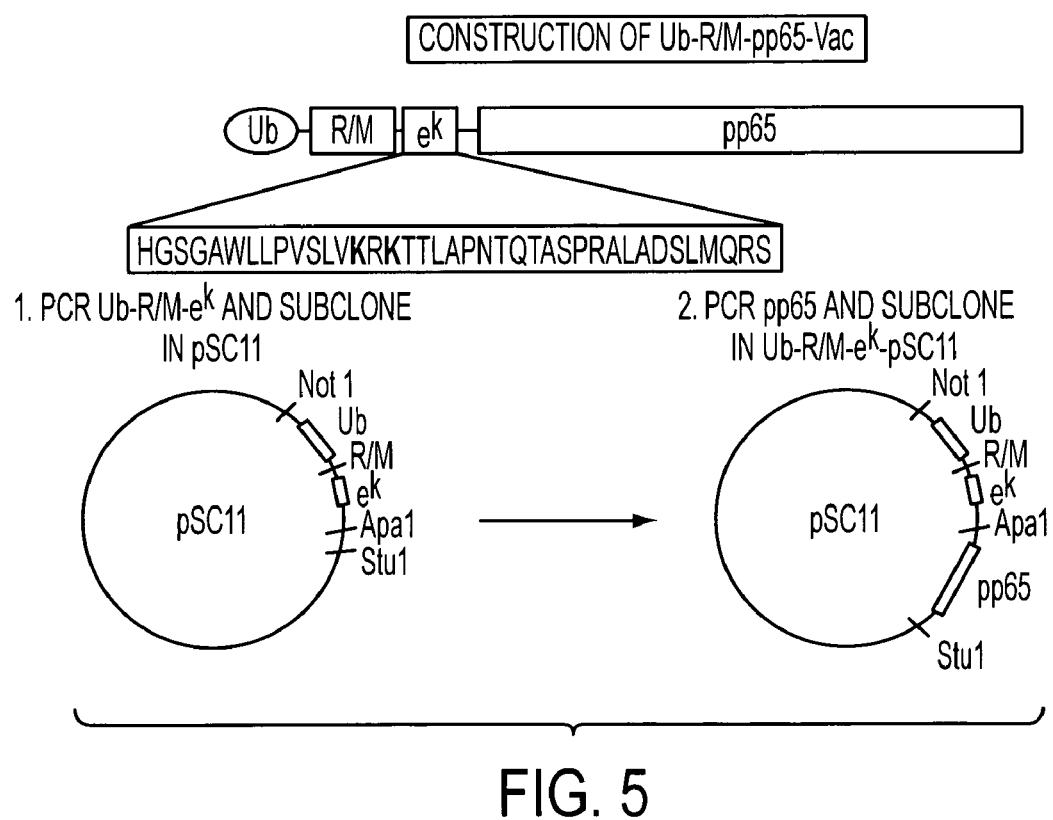
FIG. 5 is a cartoon illustrating construction of Ub-R-pp65Vac. An $e^K$ region (SEQ ID NO:1) is shown.

The human ubiquitin (Ub) gene was amplified using the following pair of primers: 5'-CAGTCAGCTAGCGTT-TAAACATGCAGATCTTCGTGAAGACC-3' (primer A; SEQ ID NO:8) and 5'-GGACAACGGCGACCGCGC-GACTCCCTACCCCCCCTCAAGCGCAGGAC-3' (primer B; SEQ ID NO:9). CMV (AD 169) pp65 gene was amplified using the following pair of primers: 5'-GTCCTGCGCT-TGAGGGGGGGTAGGGAGTCGCGCGGTCGCCGTTG TCC-3' (primer C; SEQ ID NO:10) and 5'-CCGGGTAC-CTCAACCTCGGTGCTTTTTGGGCGTC-3' primer D;

SEQ ID NO:11). Primers B and C were designed not only to complement each other, but also to contain the Arg codon (AGG), replacing Met (ATG) at the amino terminus of pp65. Alternatively, the primers can be designed to retain the ATG codon. The Ub gene (271 bp) and CMV pp65 gene PCR product (1680 bp) were fused together to generate the Ub-R-pp65 fusion gene by PCR using primers A and D. The PCR reaction conditions were five cycles at 94° C., 1 min; 55° C., 1 min; 72° C., 4 min followed by 20 cycles of 94° C., 1 min; 60° C., 1 min; and 72° C., 4 min. The resulting 1926 bp Ub-R-pp65 fusion gene product was gel purified and cloned into pSC11 insertion plasmid using Nhe I and Kpn I sites to generate Ub-R-pp65-pSC11 according to the methods described in Chakrabarti et al., *Mol. Cell Biol.* 5:3403–3409, 1985, the disclosures of which are hereby incorporated by reference. The construct sequence was verified by restriction enzyme digestion and DNA sequencing. Ub-R-pp65 recombinant vaccinia virus (Ub-R-pp65Vac) was generated by transfecting the Ub-R-pp65-pSC11 plasmid into vaccinia virus infected HuTK cells. See FIG. 5. Ub-R-pp65Vac was simultaneously screened and selected by color reaction of substrates (Bluogal", Sigma-Aldrich) to β-galactosidase and resistance to BrdU according to the methods described in Diamond et al., *Blood* 90:1751–1767, 1997, the disclosures of which are hereby incorporated by reference. Purity was tested using PCR. Unmodified pp65Vac also was produced by similar methods.

Figure 6:
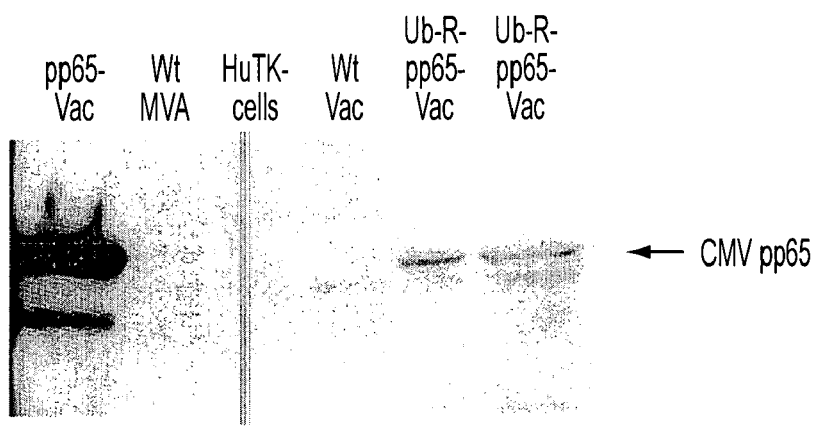
FIG. 6 is a western blot analysis showing expression of modified and unmodified pp65 protein.

The expression of pp65 was detected by western blot according to known methods. See FIG. 6, which shows the results of western blot analysis comparing Ub-modified pp65 (lane 5) versus unmodified pp65 (lane 1). The western blot confirms that the respective ubiquitinated proteins are expressed, but at a dramatically lower level than the corresponding unmodified forms. This may reflect instability of full-length ubiquitinated proteins.

Figure 7:
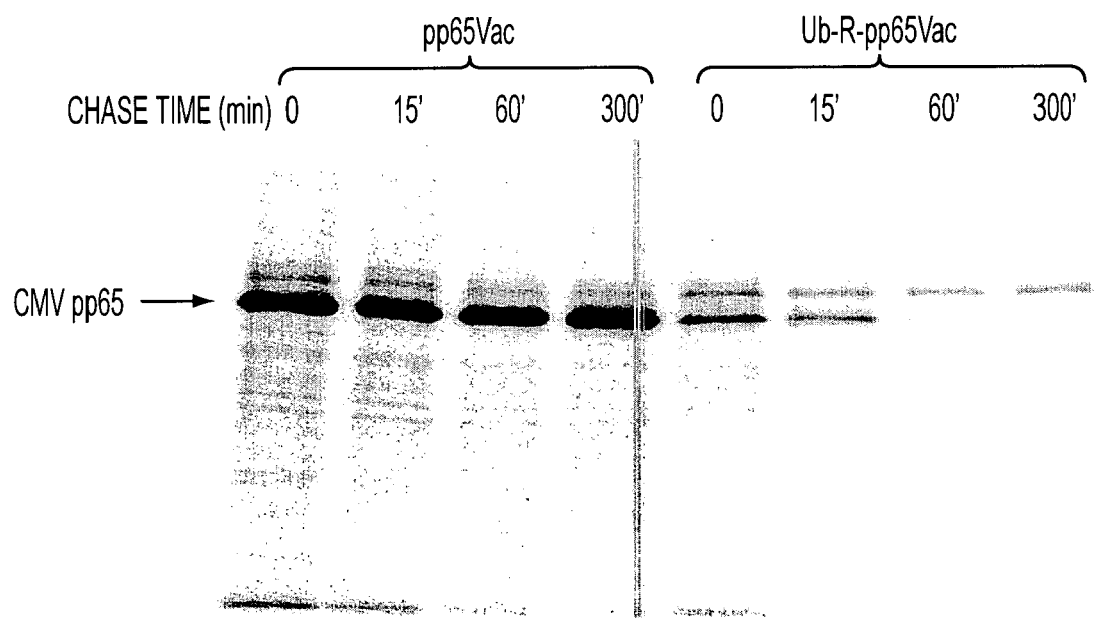
FIG. 7 is a western blot showing rapid degradation of Ub-modified pp65 expressed in HuTK cells with vaccinia virus.

The effect of Ub-modification on protein stability was assayed using half-life analysis by pulse-chase testing as follows. Briefly, HuTK cells were infected with vaccinia viruses expressing the forms of pp65 indicated in FIG. 7, the cells were depleted of methionine for an extended period according to pulse-chase methodology known in the art and Trans-Label" (ICN Radiochemicals, Costa Mesa, Calif.) was added for 30 minutes, then chased for the indicated times with added cold methionine and cysteine. The cells then were frozen and then solubilized in SDS-containing buffer.

1. Preparation of CV-1 Cells and Recombinant Vaccinia Virus.

CV-1 cells were grown in two 100 mm tissue culture dishes to 90% confluency. All the CV-1 cells from two dishes were used to seed eight T75 flask one day before pulse chase metabolic labeling. Each T75 flask was estimated to have $5 \times 10^6$ CV-1 cells. Recombinant vaccinia stock virus was prepared and titrated according to standard procedure. Ub-pp65 vac was $5 \times 10^9$ PFU/ml. Pp65 vac was $2.5 \times 10^9$ PFU/ml.

2. Pulse-Chase Metabolic Labeling with $^{35}$S-Met and $^{35}$S-Cys.

Culture medium was aspirated from the flask and the cells washed with 10 ml MEM-2 by gently swirling. Eighty microliters of Ub-pp65 vac stock virus (80 ul virus+80 ul 0.25% trypsin) and 160 ul pp65 vac stock virus (160 ul stock virus+160 ul 0.25% trypsin) was trypsinized for 30 minutes wit vortexing every 10 minutes. Twelve milliliters of MEM-2 medium was added to each tube and mixed well. Three milliliters of the medium was distributed to each of eight T75 flasks, (4 for Ub-pp65 vac and 4 for pp65 vac). The flasks were incubated at 37° C. for 2 hours with swirling every 30 minutes. Infected CV-1 cells were washed with 10 ml Met-free, Cys-free RPMI medium, once. Then, 20 ml Met-free, Cys-free RPMI medium containing 5% dialyzed FCS and antibiotics (P/S) was added. The flasks were incubated at 37° C. for 1 hour in a 5% $CO_2$ incubator. 35S L-methionine was thawed at room temperature to prepare a working solution at 0.1 mCi/ml labeling medium. This solution (250 μl) was pipetted into 25 ml Met-free, Cys-free RPMI medium containing 5% dialyzed FCS and antibiotics. Three milliliters of the labeling working solution was distributed to each flask with gentle swirling and incubated at 37° C. for 30 minutes. Cells were washed with 10 ml warm Met-free, Cys-free RPMI 1640 medium once. RPMI 1640 medium (10 ml) containing 10% FCS, antibiotics, 10×Met, 10×Cys was added to chase the pp65 labeling. The labeling cells were harvested at 0 min, 15 min, 60 min and 300 min. After incubation at each time point, cells were scraped off and collected in a 15 ml tube. Cells were washed once with ice-cold PBS. Cell pellets were stored in 80° C. or used immediately in the next step.

3. Immunoprecipitation by Protein G-sepharose 4B.

ell pellets were resuspended in 1 ml cell lysis buffer (10 mM Tris-HCl, pH7.4, 150 mM NaCl, 0.1% SDS, 1% Triton X-100, 1% Sodium Deoxycholate, 100 ug/ml PMSF and 1 ug/ml aprotinin) and vortexed. All lysates were transferred to 2 m 1 microcentrifuge tubes and subjected to centrifugation at maximum speed for 5 minutes at 4° C. Supernatants were transferred into fresh 1.5 ml tubes and precleared one time with 100 ul portein G-Sepharose beads by rotating the mixture for 2 hour at 4° C., then subjected to centrifugation at maximum speed for 5 minutes at 4° C. The supernatants were transferred in 250 μl aliquots into 1.5 ml tubes and stored at −80° C. At this point they were ready for immunoprecipitation. For immunoprecipitation, 120 μl pp65 purified pp65 antibodies (0.2 ug/ul) were mixed with 750 μl of cell lysis buffer. This mixture (100 μl) was distributed into each 250 μl radiolabed cell lysis solution. The tubes were mixed gently by rotating for 2 hours. For hybridoma tissue culture supernatant, 100 μl was used. When ascites is used, 1:20 to 1:200 were appropriate. The contents of Protein G-Sepharose were shaken until a uniform suspension was obtained. Immediately after shaking, a 500 ul aliquot of Protein G-Sepharose was removed and placed into a microcentrifuge tube. Buffer solution (100 μl) was removed and 100 μl cell lysis buffer was added. Protein G-Sepharose 4B (50 μl) was transferred to each microcentrifuge tube containing antibody-antigen complex and the tube agitated for one hour at 4° C. by end over end rotation. The tube then was subjected to centrifugation at 8000 rpm for 3 minutes. The supernatant was discarded. The beads were washed with 1 ml cell lysis buffer three times, removing as much liquid as possible. Then 50 μl 2× Lammeli buffer was added with gentle mixing to prevent Sepharose from sticking to the side of the tube. The tube was capped securely and heated for 10 minutes at 94° C., then spun at maximum speed for 5 minutes. The supernatant was collected carefully into a fresh 1.5 ml tube with 2 μl BPB dye. The supernatant then was ready for SDS-PAGE analysis.

4. Electrophoresis of SDS-PAGE.

For loading samples, 20 μl of the sample was loaded into an apparatus for 10% mini SDS-PAGE (Bio-Rad). Discard the tip into radioactive waste container. Electrophoresis was run at 100 V for 1.5 hours until the dye reached the bottom of the gel. For the detection of radiolabeled proteins separated by SDS-PAGE, the proteins were fixed with isopropanol:acetic acid:water (25:10:65) for 30 minutes. After pouring off the fixing solution into a radioactive waster container, the gel was soaked in Amplify™ solution (at least 4 times volume of gel) with agitation for 30 minutes. The gel was removed from the solution and placed on a piece of plastic wrap. Whatman 3 M paper was placed on the top of gel. The gel then was flipped over so that the plastic wrap was on the top and the filter paper was on the bottom. The gel was dried at 70° C. for about one hour. For autoradiography an X-ray film was exposed at −80° C. overnight.

The data show a decrease in stability of ubiquitinated pp65 compared to unmodified pp65. The half-life decreased from more than 20 hours to about 2 hours. Replacement of the N-terminal Met residue with Arg further reduced the half life to about 20 minutes.

Example 2

IE1(4)-pLW22 Plasmid Construction

Figure 8:
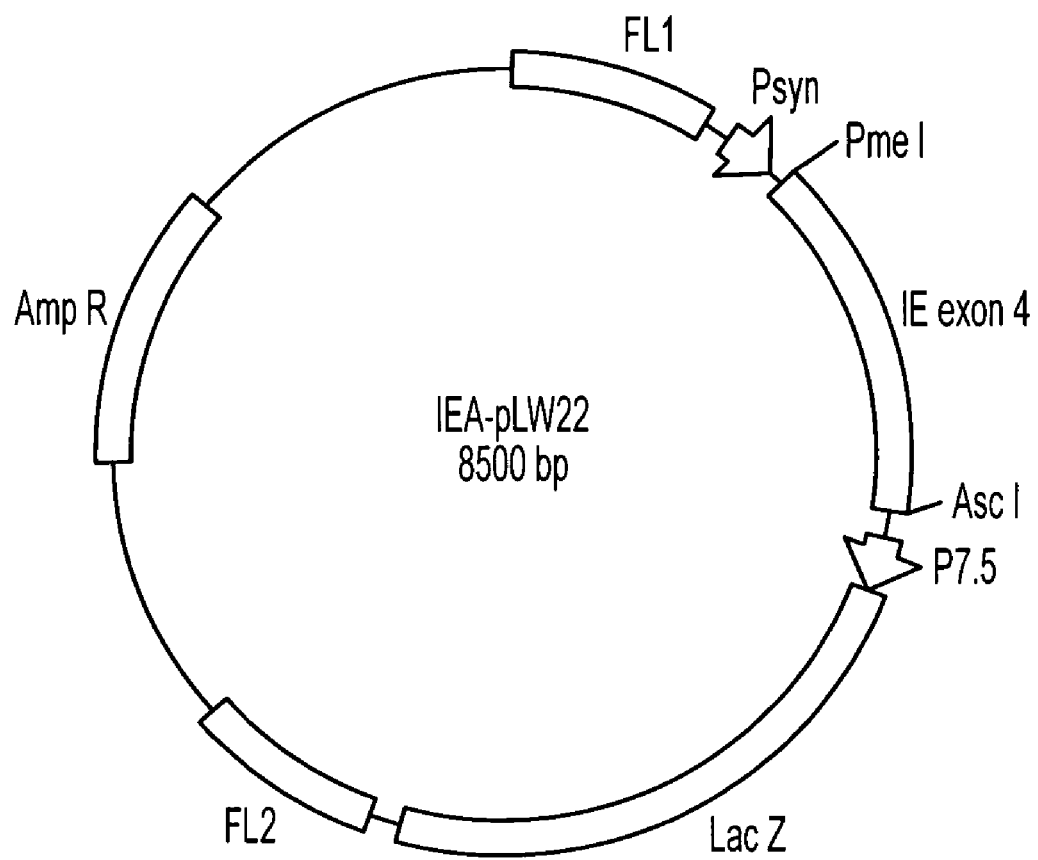
FIG. 8 is a schematic representation of IE1(4)-pLW22 plasmid, showing flanking regions FL1 and FL2 of deletion II region, IE1 exon 4 (IE1(4)) gene inserted between the PmeI and AscI sites, under the control of $P_{SYN}$ vaccinia promoter and color marker gene, lacZ, under control of P7.5 vaccinia promoter.

The IE1 cDNA was synthesized using mRNA isolated from CMV AD169-infected MRC-5 cells in a reverse transcription reaction using AMV reverse transcriptase (Promega, Madison, Wis.). The CMV IE1 gene, containing the entire IE1 ORF, was amplified using the forward primer 5'-GCAGTCACCGTCCTTGACACGATGGAG-3' (SEQ ID NO:12) and reverse primer 5'-GTGACGTGGGATC-CATAACAGTA-3' (SEQ ID NO:13). The PCR product containing CMV IE1 (1.5 kb) was digested with SalI and BamHI and gel purified, then cloned into pBluescript SK(+)™ (Strategene, La Jolla, Calif.). From this plasmid, the IE1 exon 4 gene (IE1(4)) was generated by PCR amplification using the forward PCR primer 5'-AGCTTTGTT-TAAACGCCACCACCATGGTCAAACAGAT-TAAGGTTCG-3' (SEQ ID NO:14 and the reverse primer 5'-TTGGCCGCCTTTATTTGACGTGGGATC-CATAACAGTAACTG-3'(SEQ ID NO:15). These primers contain PmeI and AscI restriction sites. After this PCR product was made, both the IE1(4) DNA and the pLW22 plasmid were cut with PmeI and AscI and gel purified. IE1(4) DNA was cloned into pLW22. The final plasmid construct designated as IE1(4)-pLW22 (see FIG. 8) was verified by restriction enzyme digestion analysis and confirmed by DNA sequencing using a Li-COR sequencer (Li-COR, Lincoln, Nebr.). The plasmid DNA used for transfection to generate rMVA preferably is purified, for example, using the Qiagen midi kit (Qiagen). Plasmids may be confirmed by restriction enzyme digestion and DNA sequencing, for example using IRD-800 labeled primers such as the following:

```
1. Sense 5'-ttgatcgggcccatacagatctt (SEQ ID NO:16)
   cgtgaagacc-3'

2. Antisense 5'-ctcgaaccttaatctgttt (SEQ ID NO:17)
   gaccctaccccccctcaagcgcaggac-3'

3. Sense 5'-gtcctgcgcttgaggggggtat (SEQ ID NO:18)
   ggtcaaacagattaaggttcgag-3'

4. Antisense 5'-aagaaggcctggcgcgcct (SEQ ID NO:19)
   tactggtcagccttgcttctag-3'
```

Example 3 pp65/pp150-pLW51 Plasmid Construction

A pp150 gene for generating rMVA was generated by RT-PCR amplification from mRNA extracts of CMV-infected MRC-5 cells and cloned into the pBluescript cloning plasmid (Strategene, San Diego, USA). CMV pp150 cDNA was verified by restriction enzyme analyses and confirmed by DNA sequencing. For safety reasons, kinase-deficient pp65 is preferred for generation of rMVA for use in humans. A CMV kinase-deficient pp65 gene was developed which has a point mutation converting lysine to asparagine at amino acid position 436 to eliminate the threonine kinase activity. This mutant pp65, termed pp65(K436N), maintains immunogenic properties, as shown in pre-clinical animal studies.

Figure 9:
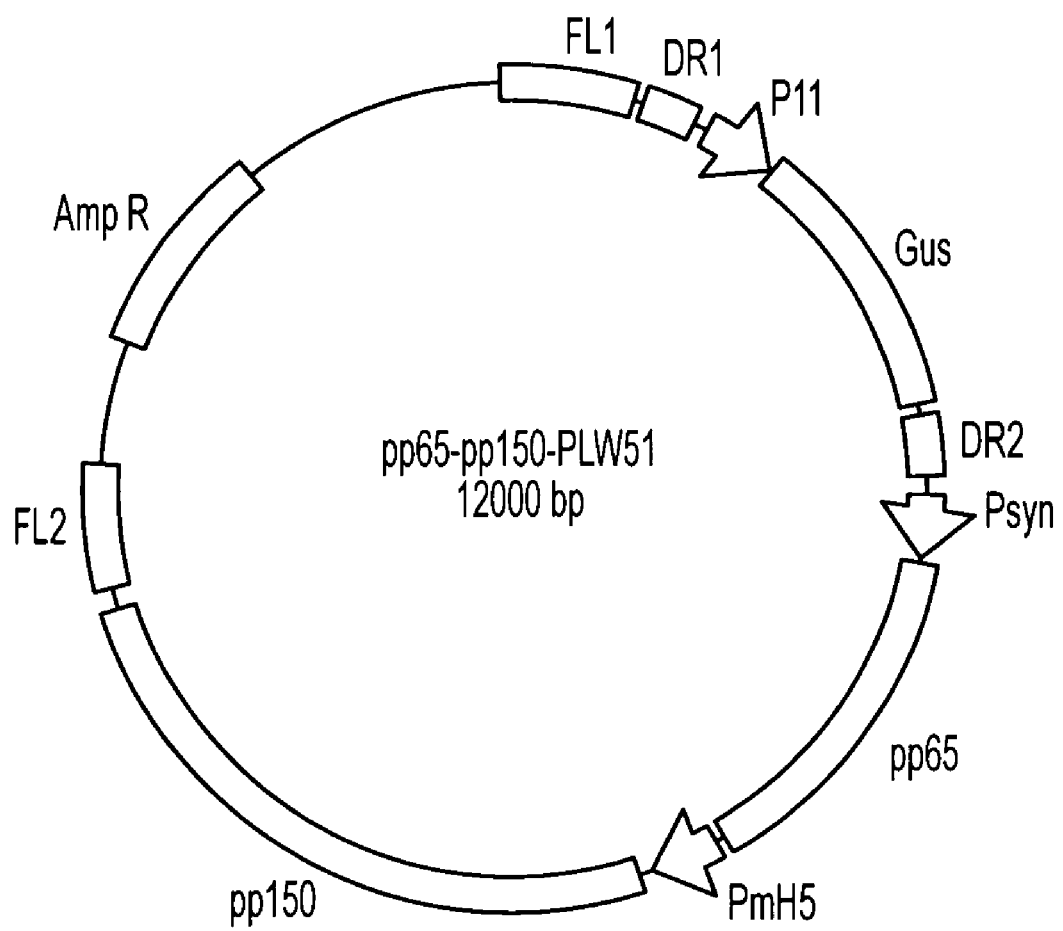
FIG. 9 is a schematic representation of pp65/pp150-pLW51 recombinant plasmid, showing flanking regions FL1 and FL2, direct repeats DR1 and DR2, Gus gene under control of P11 promoter and pp65 inserted into MCS1 and pp150 inserted into MCS2 under control of the $P_{SYN}$ and $P_{mH5}$ vaccinia promoters, respectively.

CMV pp65 gene was PCR amplified using forward primer 5'-aaggaaaaaagcggccgcgccaccac-catggagtcgcgcggtcgccgttgtcc-3'(SEQ ID NO:20) and reverse primer 5'-aagaaggcctttatttcaccctcggtgcttttgggcgtc-3' (SEQ ID NO:21). The pp65 gene PCR product was gel purified and cloned into the Not I and Stu I sites of MCS 1 of pLW51 under the control of the $P_{SYN}$ vaccinia promoter. The PCR product of the pp150 gene using forward primer 5'-agctttgtttaaacgccaccaccatgagtttgcagtttatcggt-3' (SEQ ID NO:22) and reverse primer 5'-aagaaggcctttatttcaccctcggt-gctttttgggcgtc-3' (SEQ ID NO:23) was cut with PmeI and AscI and gel purified, then cloned into the second MCS under the control of the $P_{mH5}$ promoter. See FIG. 9. Both the pp65 and pp150 genes were checked by restriction analyses and confirmed by DNA sequencing (Li-COR). The plasmid DNA to be used for transfection/infection to generate rMVA preferably was purified with the Qiagen Plasmid DNA midiprep kit (Qiagen).

CEF cells simultaneously were infected with wild type MVA and transfected with pp65/pp150-pLW51 plasmid to produce pp65/pp150-rMVA. See Example 8. The virus was purified, then autologous EBVLCL were infected in vitro with this recombinant MVA.

Example 4

Construction and Expression of IE1 exon 4 in MVA

Figure 10:
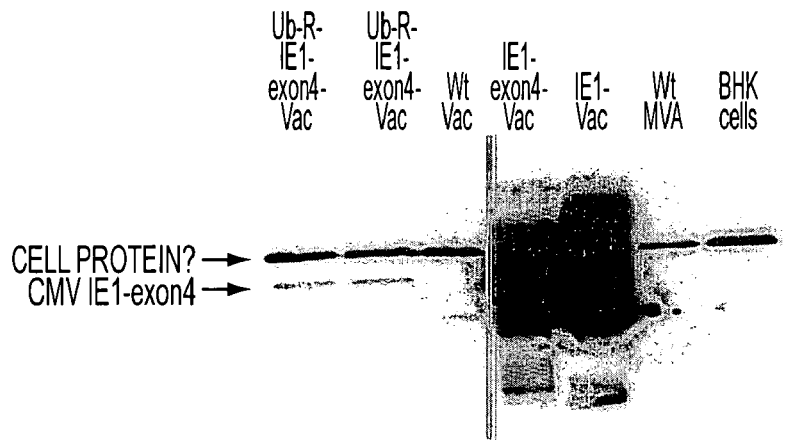
FIG. 10 is a western blot comparing Ub-R-modified and unmodified IE1(4) expression in BHK cells by rMVA.

A gene encoding unubiquitinated IE1 exon 4 (Ub-M-IE1(4)) or ubiquitinated IE1 exon 4 in which the amino terminal methionine was replaced with arginine (Ub-R-IE1(4)) was inserted into pLW22 as described in Example 2 and transfected into CEF cells infected with wild type MVA. The resulting recombinant virus was plaque-purified for at least six cycles. Purity was tested using PCR. The recombinant MVA was used to infect BHK cells for expression. FIG. 10 shows rapid disappearance of Ub-modified protein in a western blot analysis comparing expressed Ub-modified protein and unmodified protein in these cells. A cross-reacting cellular protein serves as a marker, demonstrating equivalent loading in all lanes.

Example 5

Production of pp65/pp150/IE1(4)-rMVA

CEF cells are aliquoted into 100 tissue culture dishes (150 mm in diameter) and incubated at 37° C. in a 5% $CO_2$ incubator until 100% confluent in the presence of MEM-10

(Minimal Eagles Medium containing 10% fetal calf serum). The cells then are washed with PBS to remove any remaining serum in the dish and trypsinized with 1× trypsin/EDTA (Irvine Scientific, CA). The culture dishes are shaken gently to detach cells completely. The detached cells are collected, counted, resuspended in cell-freezing medium, and aliquoted into cryovials (50 million cells per vial). Cryovials are frozen in liquid nitrogen. CEF cells then may be thawed as needed.

The initial stock of wild type MVA virus may be obtained from any convenient source. Wild type MVA stocks for generation of rMVA are propagated in CEF cells. About ten 150 mm diameter dishes of CEF cells are grown until they reach approximately 80 to 90% confluency. Wild type MVA initial stock virus is sonicated 30 seconds in cold water using a cup horn sonicator (Branson Sonifier 250) and diluted in MEM-2 to achieve an MOI of 0.01. About 3 ml diluted virus is applied to the CEF cells in each culture and incubated for two hours in a 37° C., 5% $CO_2$ incubator. The dishes are rocked gently by hand at 30 minute intervals during the infection. After 2 hours, MEM-10 medium is added to the cells, which then are incubated until viral cytopathic effect is evident over the entire dish. This usually takes about 48 hours. Virus-infected cells are harvested using a sterile cell-scraper and collected into a sterile plastic screw-cap tube. The cell pellets are resuspended in 1 ml of MEM-2 and subjected to three cycles of freezing in an ethanol/dry ice bath, thawing in a 37° C. water bath, and vortexing briefly to release the virus. The virus stock will be titrated by immunostaining (see Section 4.8 below), aliquoted, and stored at −80° C.

Figure 11:
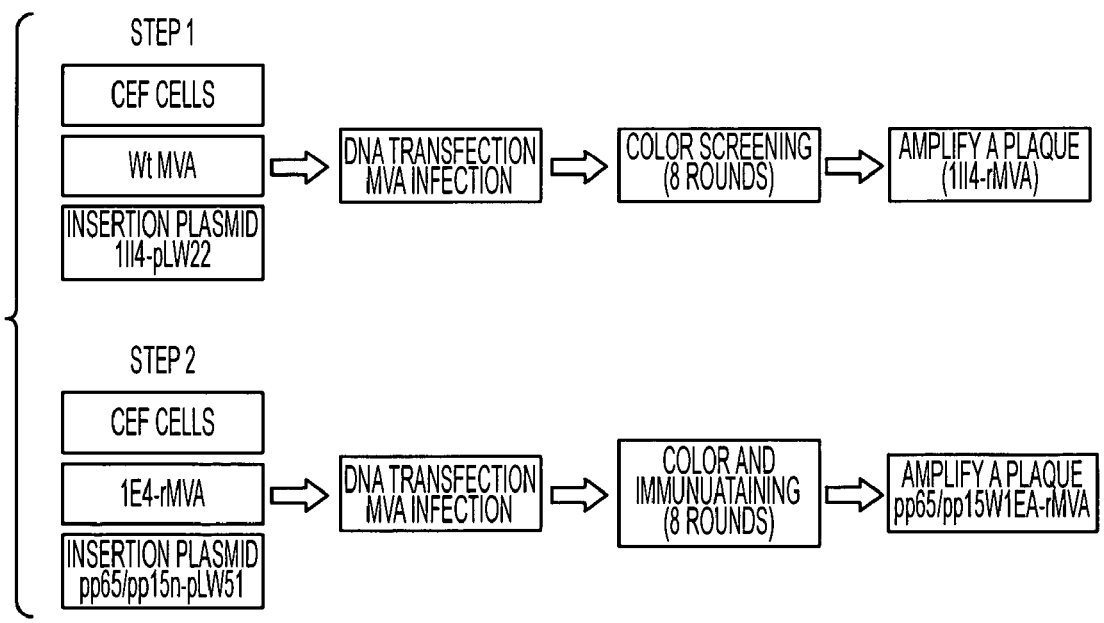
FIG. 11 is a flow chart showing steps for producing pp65/pp150/IE1(4)-rMVA. Step 1 shows generation of IE1(4)-rMVA by IE1(4)-pLW22 insertion plasmid transfection and wild type MVA infection on CEF cells. Step 2 shows generation of pp65/pp150/IE1(4)-rMVA by pp65/pp150-pLW51 transfection and IE1(4)-rMVA infection of CEF cells.

Recombinant MVA virus expressing the CMV pp65, pp150, and IE1(4) proteins is produced by inserting DNA that encodes IE1(4), under control of the $P_{SYN}$ promoter, into deletion II of MVA using pLW22 insertion plasmid, and inserting pp65 and pp150 genes, under control of the $P_{SYN}$ and mH5 promoters, into deletion III of MVA using the pLW51 insertion plasmid. This is accomplished in two steps. See FIG. 11.

Example 6

Expression of CMV Antigens

A recombinant MVA virus expressing IE1(4) (designated IE1(4)-rMVA) is produced by transfecting IE1(4)-pLW22 insertion plasmid into wild-type-MVA-infected CEF or BHK-21 cells. Then, screening and amplification of IE1(4)-rMVA are performed. The IE1(4)-rMVA virus is used in the subsequent transfection/infection. pp65/pp150-pLW51 plasmid (inserting into deletion III) is transfected into CEF cells infected with IE1(4)-rMVA. Recombinant MVA expressing pp65, pp150, and IE1(4) (designated as pp65/pp150/IE1(4)-rMVA) are thereby generated via homologous recombination. pp65/pp150/IE1(4)-rMVA is isolated and purified using gus color screening in the presence of X-GlcA (Sigma) and immunostaining selection using anti-pp65 monoclonal antibody, as described herein. IE1(4)-rMVA (delII) is modified by homologous recombination with pLW51 expressing both pp65 and (gB(s)) in the same manner and plaque-purified to produce gB(s)/pp65/IE1(4)-rMVA.

Transfection is accomplished as follows. Two wells of a 6-well tissue culture plate are seeded with CEF or BHK-21 cells at 0.6×10⁶ cells per well in 0.5 ml of MEM-10 and incubated overnight in a 37° C. and 5% $CO_2$ incubator to obtain approximately 80% confluency in the wells on the following day. A standard Lipofectin® (InVitrogen) transfection is set up by preparing the following in two 12×75 mm polystyrene sterile tubes: Tube 1: 200 μl OptiMEMT™ (Life Technologies, Gaithersburg, Md.)+80 μl Lipofectin®, Tube 2: 200 μl OptiMEMT™+40 μg insertion plasmid DNA. The tubes are incubated individually at room temperature for 30 minutes, and then the contents from the two tubes are combined and mixed together by gently pipetting up and down. The tube containing the mixture of Lipofectin®/DNA/OptiMEM™ is incubated at room temperature for another 15 minutes. During this time, the MVA stock is thawed at 37° C., and then sonicated in ice water for 30 seconds. An aliquot of the virus is diluted with OptiMEM™ and added to the Lipofectin®/DNA/OptiMEM™ tube to achieve an MOI of 0.01. Then the volume of Lipofectin®/DNA/MVA mixture in the tube is brought up to 2 ml with OptiMEM™. The media is aspirated from the wells of the CEF plates, and the CEF cell monolayer in each well is washed gently with 1 ml of OptiMEM™ and gently overlayered with 1 ml of the Lipofectin®/DNA/MVA mixture prepared above. The plates are incubated at 37° C. in a 5% $CO_2$ incubator. After 4 hours incubation, 4 ml of MEM-10 is added to each well and the plates are further incubated at 37° C. in a 5% $CO_2$ incubator for 2 to 3 days.

Plasmid DNA-transfected and MVA-infected CEF cells are harvested with a sterile cell scraper into a single sterile screw-cap tube after 3 days incubation. The cell pellets are resuspended in 400 ul of MEM-2 and subjected to 3 cycles of freezing in a dry ice/ethanol bath, thawing in a 37° C. water bath, and vortexing to release the virus. The virus cell lysates are sonicated twice in ice water for 30 seconds and stored at −80° C. for screening of rMVA.

After 10 rounds of screening and PCR verification to ensure the absence of wild type virus, plaque-pure rMVA is used to infect CEF or BHK-21 cells at an MOI of 0.01 for 10 for 16 hours. Membranes are prepared from the cells and subjected to 4–10% gradient polyacrylamide gel electrophoresis. The separated proteins are transferred to polyvinylidenefluoride (PVDF) and stained according to known methods using primary monoclonal antibodies specific for CMV antigens and an ECL kit (Amersham).

Example 7

Expression of Single and Multiple Proteins for rMVA

FIG. 12 shows expression of protein from IE1(4) expressed from MVA constructed using pLW22 (FIG. 12A), pp65 expressed from MVA constructed using pMCO3 (FIG. 12B) and pp150 expressed from MVA constructed using pLW22 (FIG. 12C). Briefly, pMCO3 is a plasmid insertion vector containing MVA flanking regions which inserts into deletion III of MVA. It contains a single strong synthetic promoter ($P_{SYN}$) and expresses the gene for screening purposes under the control of $P_{7.5}$. pMCO3 was constructed by the addition of $P_{7.5}$ and GUS to the pLW-4 transfer plasmid at the SmaH1 site. See Carroll and Moss, *Biotechniques* (3):352–354, 356, 1995; Wyatt et al., *Vaccine* 14(15):1451–1458, 1996. In lanes 1, 8, 9, are AD-169 CMV cell lysates (Microbix Biosystems Inc.) for detection of pp65, pp150 and IE4 and uninfected BHK cell lysates in Lane 2, 7, 10. Cell lysates from pp65/pp150-MVA infected BHK-21 cells (lane 3, 6), UbRpp65-MVA infected BHK-21 cells (lane 4), UbMpp65-MVA infected BHK-21 cells (lane 5), IE4-MVA infected BHK-21 cells (lane 11) and UbRIE4-MVA infected BHK-21 cells (lane 12) are shown. All lanes were loaded with the same amount of protein as determined by Bradford method. pp65 protein expression was detected using mAb (103-28), pp150 expression was detected using mAb (1.XPA 36) and IE1 exon 4 expression was detected using mAb (p63-27).

Figure 13:
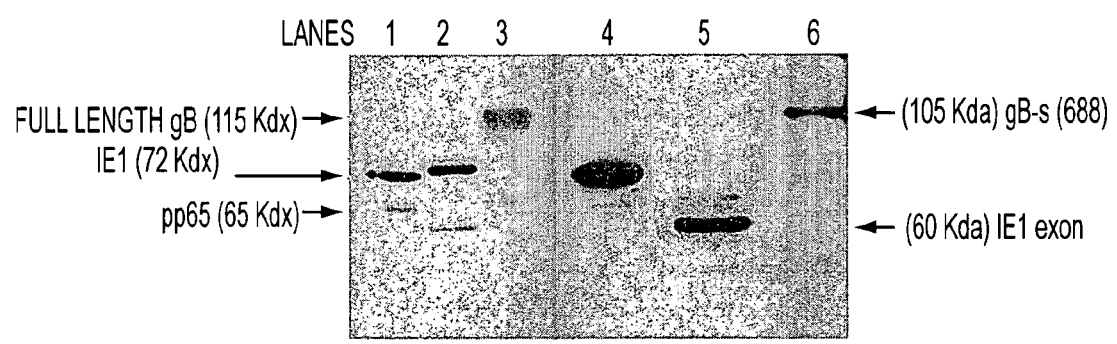
FIG. 13 is a western blot showing expression of three CMV antigens from a single rMVA (pp65/gB(s)/IE1(4)).

FIG. 13 shows co-expression of gB(s), pp65 and IE(4) from a single rMVA. Lanes 1 and 2 were loaded with 20 µl CMV-infected cell lysate (Microbix Biosystems, Ontario, Canada, Lot No. 01106A1). Lane 3 was loaded with purified full-length gB from baculovirus. Lanes 4, 5 and 6 each were loaded with 7 µl pp65/gB(s)/IE1(4) three-antigen rMVA infected cell lysate (MOI=0.01). After electrophoresis, the separated antigens were transferred to membrane, which was cut into six strips and blotted with monoclonal antibodies: anti-pp65 (28-19) in lanes 1 and 4, anti-IE1(p63-27) in lanes 2 and 5, and anti-gB (58-15) in lanes 3 and 6. All three proteins were detected at very high levels, demonstrating successful expression of all three CMV proteins. See also Example 19, which demonstrates robust expression of gB(s) from rMVA. All four proteins therefore have been demonstrated to be expressed using methods according to the invention.

Example 8

Western Blot Detection of pp150 and IEI Exon 4 Expressed in MVA

FIG. 14 shows western blots of pp150 and IE4 expressed by pp65/pp150-MVA, IE4-MVA and Ub-R-IE4-MVA. Lanes 8 and 9 are AD-169 CMV cell lysates (Microbix Biosystems, Inc.). Lanes 7 and 10 are uninfected BHK cell lysates. Lane 6 is cell lysate from pp65/pp150-MVA infected BHK-21 cells; lane 11 is cell lysate from IE4-MVA infected BHK-21 cells and lane 12 is cell lysate from Ub-R-IE4-MVA infected BHK-21 cells. All lanes were loaded with the same amount of protein as determined by the Bradford method. pp150 and IE4 expression were detected using mAb (1.XPA 36) and mAb (p63-27), respectively. HLA A*0201 $pp65_{495-503}$ (SEQ ID NO: 3) and HLA B*0702 $pp65_{417-426}$ T cell clones derived from different CMV seropositive donors were able to efficiently lyse (>70% at E:T=10) EBV-LCL targets infected with rMVA at an m.o.i. of 5 (data not shown). The cytotoxic activity was similar to that obtained when pp65-Vac were used to infect EBV-LCL in an analogous experiment (data not shown). pp65/pp150-MVA infected EBV-LCL also were able to induce potent HLA-restricted cytotoxicity (>60%, at E:T=10) in HLA A*0301 $pp150_{945-955}$ specific T cell clones (data not shown).

Example 9

Color screening for pp65/pp150/IE1(4)-rMVA

A 6-well tissue culture plate is seeded with CEF cells at $0.6 \times 10^6$ cells/well and incubated overnight at 37° C. The lysate from the transfection/infection prepared in Example 8 above is thawed in a 37° C. water bath, and then sonicated in ice water for 30 seconds. A 1 ml 1:10 dilution is made with MEM containing 2% FCS MEM-2 (10-1) and then five more serial dilutions ($10^{-2}$ to $10^{-6}$) following that. The media is aspirated from the plates, and 1 ml of one lysate dilution is plated per well. The plate is incubated at 37° C. for 2 hours.

Fifteen minutes before the incubation is complete, 2% low melting point (LMP) agarose is melted in a microwave and placed in a 45° C. water bath. 2×E-MEM (Quality Biologicals) also is placed in a 45° C. water bath. When the incubation is complete, 10 ml LMP agarose and 10 ml 2×E-MEM is mixed in a 50 ml tube. The lysate from the 6-well plate is removed, and 3 ml of the E-MEM/agarose mixture is layered over each well. The plates are placed at 4° C. for 10–15 minutes to allow the agarose to gel completely. The plates then are incubated at 37° C. for 2 days. After 2 days, LMP agarose is melted in a microwave. Both LMP agarose and 2×E-MEM are prewarmed in a 45° C. water bath. Six and one half milliliters LMP agarose, 6.5 ml 2×E-MEM, and 65 µl X-GlcA α-glucoronidase A) (for gus screening) or 32.5 µl Bluo-Gal (for lacZ screening) is mixed in a 15 ml tube. Two milliliters of this mixture is pipetted into each well. The plates then are placed at 4° C. for 10–15 minutes to allow the agarose to gel. The plates then are incubated at 37° C. overnight to allow color staining of recombinant MVA.

Greenish-blue (gus) or dark blue (lacZ) foci are selected from the most diluted well and pulled as agar plugs. The viral infected cells from the plug are added to 400 µl MEM-2 in a 15 ml tube, and subjected to three cycles of freezing/thawing. The lysates are stored at –80° C.

Example 10

Color Screening of CEF Cells Expressing aB(s) from MVA

Figure 15:
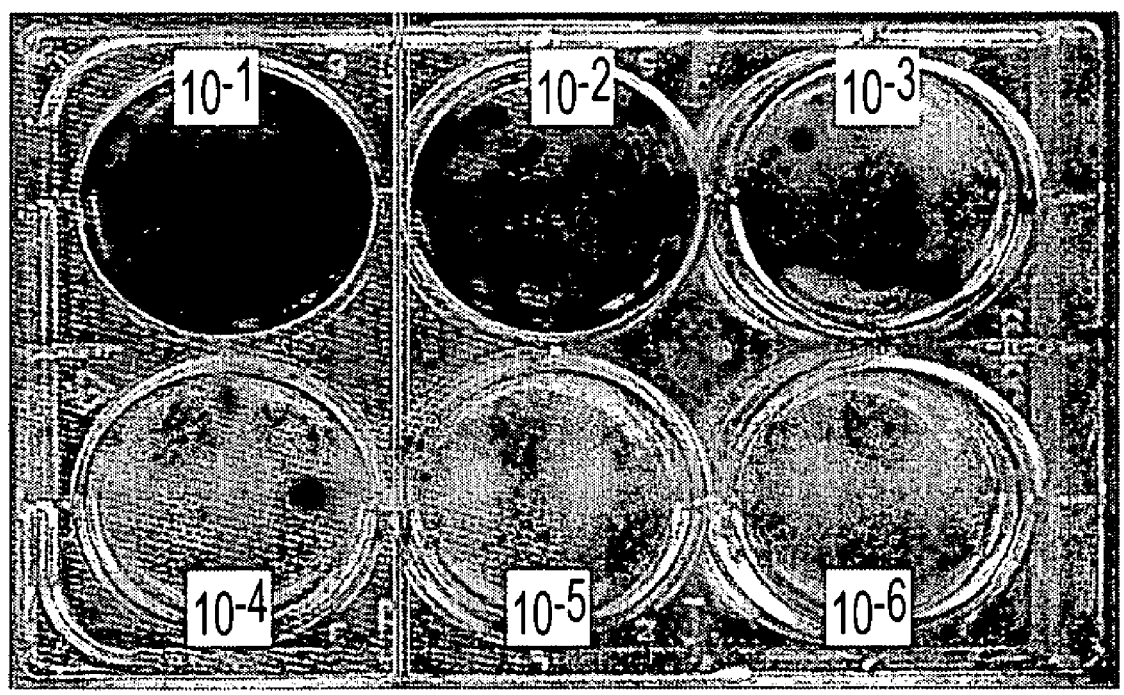
FIG. 15 is a photograph of color screening for recombinant MVA in a 6-well plate. Virus solution is diluted from 1:10 to 1:10⁶.

An example of color screening is shown in FIG. 15.

Example 11

Expansion of Human CMV-Specific CTL with rMVA-Infected EBVLCL

Figure 16A:
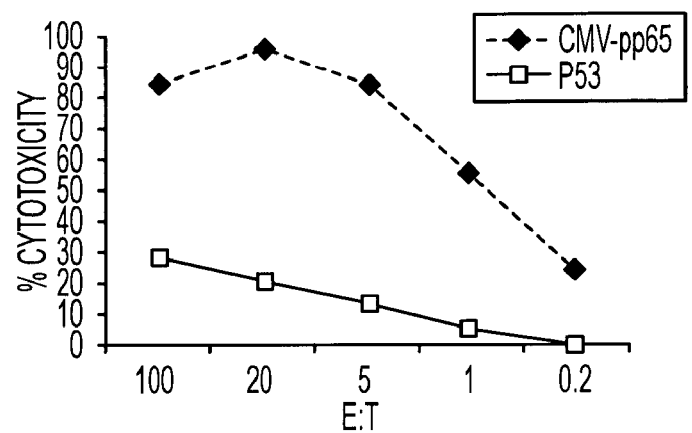
FIG. 16 shows expansion (fluorescence-activated cell sorting results, FIG. 16B) and cytotoxic activity (cytotoxicity results, FIG. 16A) of human CMV-specific T cells in response to stimulation in vitro by EBVLCL infected with pp65/pp150-rMVA.
Figure 16B:
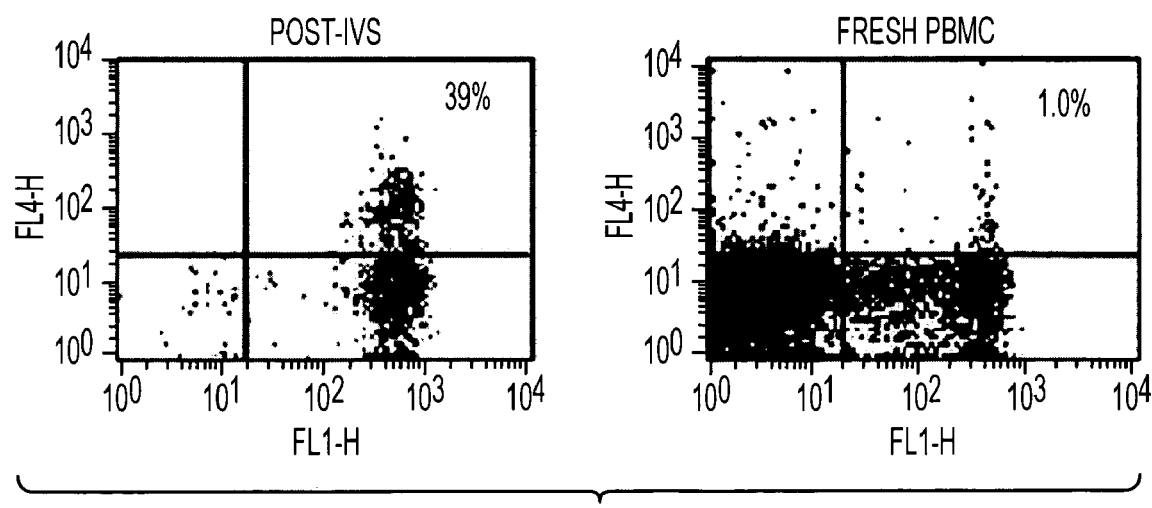
Figure 17A:
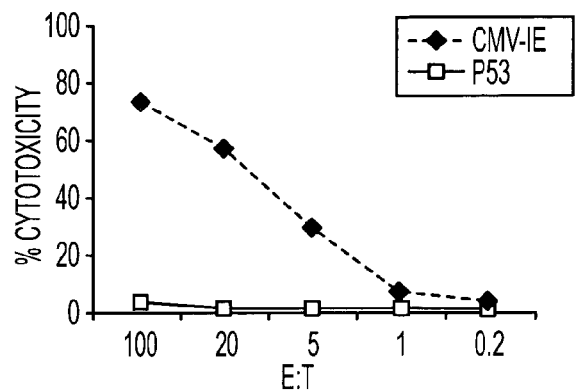
FIG. 17 presents the same data as FIG. 16 for human CMV-specific T cells after stimulation in vitro by EBVLCL infected with IE1(4)-rMVA.
Figure 17B:
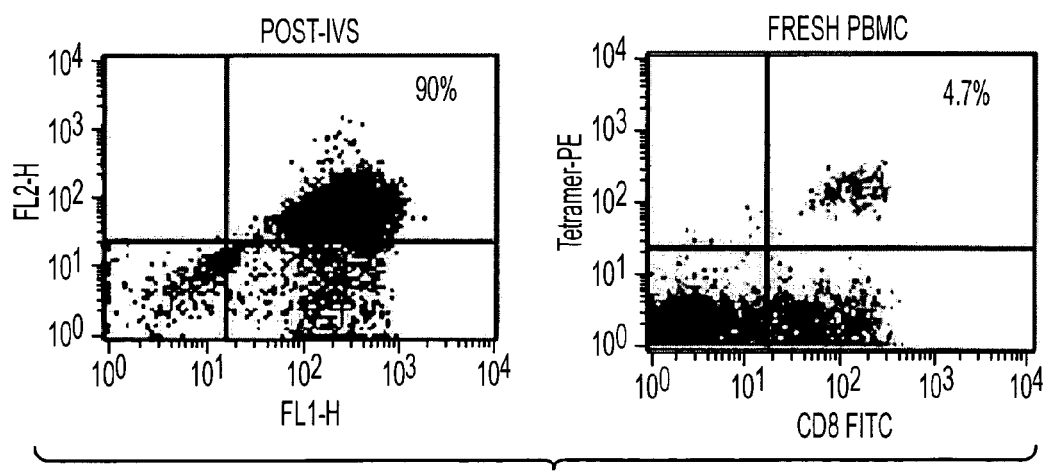

Autologous EBVLCL were simultaneously infected with pp65/pp150-rMVA or IE1(4)-rMVA at an MOI of 15 for two hours. The virus was inactivated using a Stratalinker" instrument (Stratagene) for 75 seconds at full power, followed by irradiation using a $^{137}$Cs source (5000 rads). The virally infected antigen presenting cells were mixed at a ratio of 5:1 with peripheral blood mononuclear cells from CMV-seropositive human volunteers to expand CMV-specific T cells in that population. After 12 days of in vitro culture, both pp65-specific and IE-specific CD8$^+$ T lymphocytes were expanded and active. See FIGS. 16 and 17. FIGS. 16A and 17A show cytotoxicity of CMV pp65-expressing and CMV IE-expressing targets, respectively, relative to targets expressing the irrelevant p53. FIGS. 16B and 17B provide fluoresence-activated cell sorting results that show the expansion of pp65-specific and IE-specific CD8$^+$ cells, respectively, after the in vitro stimulation (IVS). This confirms both the functional activity of the recombinant MVAs and the ability to expand in vitro CMV-antigen-specific T cells for use in adoptive immunotherapy.

Example 12

Figure 18:
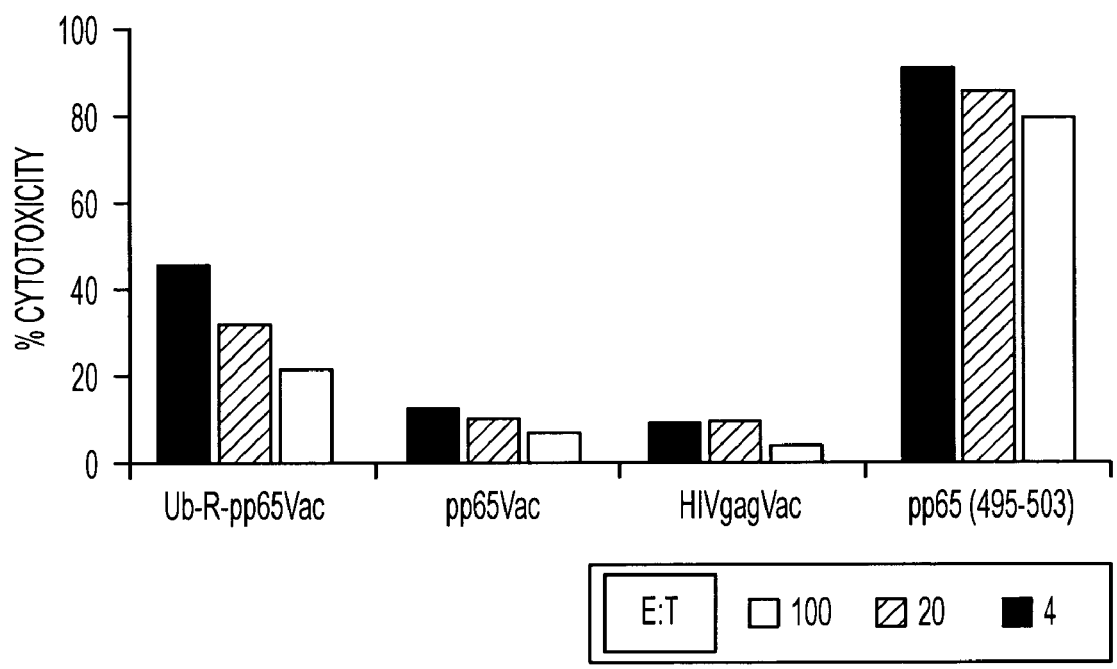
FIG. 18 provides results of a chromium release cytotoxicity assay using JA2.1 T cells infected with Ub-R-pp65Vac, pp65Vac or pulsed with CMV peptides as targets and a bulk splenocyte line from mice immunized with SEQ ID NO:2 as effectors at the indicated effector:target ratios. Control targets (HIVgagVac) also are shown.

Recognition of Ub-pp65 Vaccinia-Infected Antigen Presenting Cells by a Bulk Line of Splenic Effectors Derived from Fusion Peptide Immunizations A bulk line was derived from splenocytes from mice immunized with Pam$_2$-KSSAKXVAAWTLKAAANLVPM-VATV wherein X=cyclohexylalanine (SEQ ID NO:2) after 5 in vitro stimulations. This fusion peptide is a dilipidated fusion of a CMV pp65 epitope (NLVPMVATV; SEQ ID NO:3) and PADRE, a T help epitope. The cell line was a homogeneous CD8+ T cell population by flow cytometry (data not shown). A chromium release assay was performed using targets (JA2.1 T cells) either infected with Ub-R-pp65 recombinant vaccinia virus (Ub-R-pp65Vac) (as prepared in Example 1) for 16 hours at an MOI of 3 or pulsed with CMV peptides. See FIG. 18. Non-specific lysis is shown (HIV-gagVac) for vaccinia virus-infected targets, and was less than 5% for peptide-loaded T2 cells. Ubiquitin modification increased CTL response compared to unmodified pp65.

Example 13

Recognition of Endogenously Processed Ub-R-pp65Vac After Primary Immunization

Figure 19:
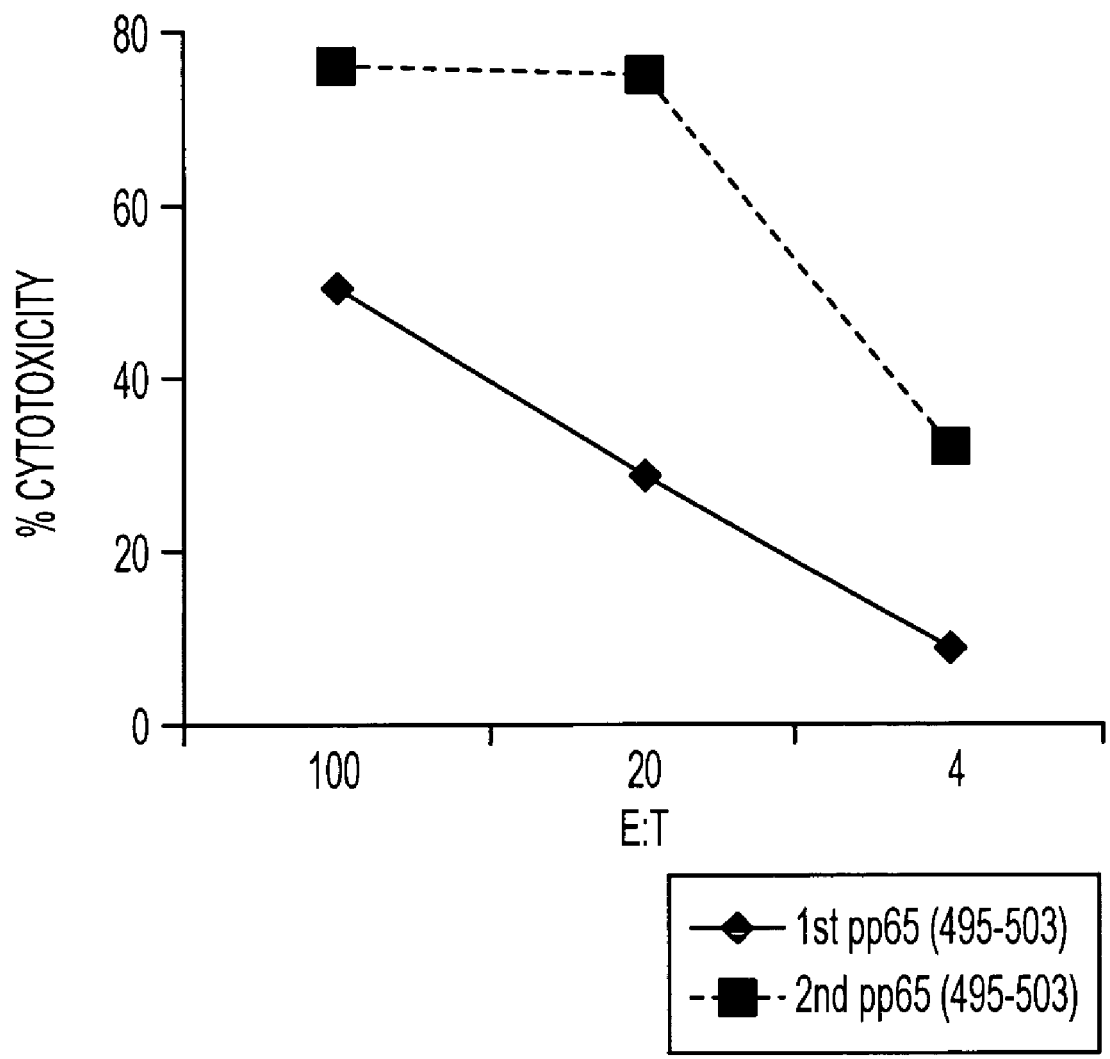
FIG. 19 shows cytotoxicity of SEQ ID NO:2-immune splenocytes for T2 cells loaded with CMV peptide. Immunization was intranasal.
Figure 20:
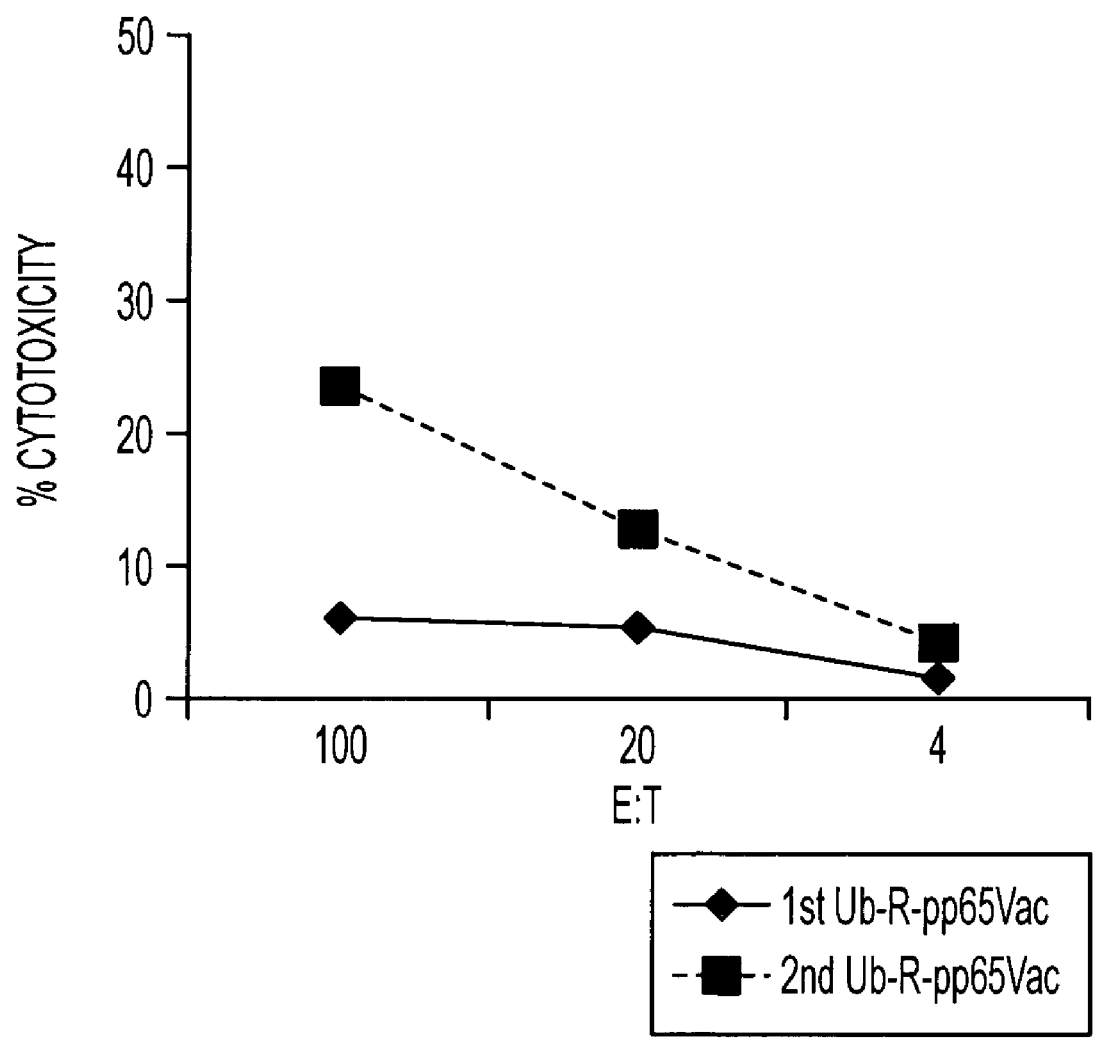
FIG. 20 shows the same data as FIG. 19 for JA2.1 T cell targets infected with Ub-R-pp65Vac.

A more rigorous test of whether CMV fusion peptides induce recognition of endogenously processed Ub-R-pp65Vac as in a viral infection is to evaluate a primary immunization. HLA A2/Kb mice were immunized intranasally once or twice with $Pam_2$-KSSAKXVAAWTL-KAAANLVPMVATV wherein X=cyclohexylalanine (SEQ ID NO:2). Immune splenocytes were obtained and used in a chromium release assay. Targets were JA2.1 T cells infected with Ub-R-pp65Vac, or T2 cells loaded with peptides. As expected, peptide-specific responses were easily measured in immune splenocytes after one immunization (FIG. 19), but recognition of endogenously processed pp65 was minimal, even when it was expressed as the Ub-R-pp65Vac (FIG. 20). However, following a second immunization, substantial killing (>20%) was detected of JA2.1 cells expressing modified pp65 from Ub-R-pp65Vac. These data confirm that fusion peptides delivered intranasally stimulate CTL that recognize processed full length pp65.

Example 14

Efficient Amplification of CMV-Specific CTL

To determine whether ubiquitin modification of CMV pp65 results in more efficient amplification of CD8+ T cells than unmodified protein, an enriched population of CD8+ T cells was produced as follows. Samples of fresh peripheral blood (50 ml) from healthy CMV-seropositive human donors were separated by centrifugation through Ficoll. CD8+ T cells were enriched by negative selection using para-magnetic bead (Dynal") purification with an anti-CD-4, CD16, CD56 monoclonal antibody cocktail. The resulting cell population (approximately 2 million T cells) was analyzed by flow cytometry and found to be greater than 98% CD3+/CD8+/CD4− (data not shown)

Autologous EBVLCL were infected for two hours at an MOI of 15 with vaccinia virus expressing Ub-R or unmodified CMV pp65 (Ub-Rpp65Vac or pp65Vac) according to known methods. Vaccinia viruses were inactivated using a Stratalinker" instrument (Strategene) for 75 seconds at full power, followed by irradiation with a $^{137}Cs$ source at 5000 rads. The virally infected antigen presenting cells were mixed 5:1 with the enriched CD8+ T cell effector population and incubated for 6–12 days. Fold amplification of the T cells in shown in Table II below, as determined by flow cytometry and HLA A*0201 tetramers bound with the CMV pp65 epitope NLVPMVATV (SEQ ID NO:3) according to methods known in the art. The cells were co-marked with CD8+ antibody.

TABLE II

Human T Cell Amplification by Antigen Presenting Cells Infected with Vaccinia Virus.

| Sample No. (HLA) | Vac Construct | Fold T Cell Increase | CMV-Specific Cytotoxicity |
|---|---|---|---|
| 1 (B*0702) | Ub-R-pp65Vac | 23 | 81.1% |
|  | pp65Vac |  | 24.5% |
| 2 (A*0201) | Ub-R-pp65Vac | 140 | 19.8% |
|  | pp65Vac |  | 3.5% |
| 3 (B*0702) | Ub-R-pp65Vac | 40 | 44.9% |
|  | pp65Vac |  | 16.0% |
| 4 (A*0201) | Ub-R-pp65Vac | 33 | 52.7% |
|  | pp65Vac |  | 2.0% |
| 5 (A*0201) | Ub-R-pp65Vac | 150 | 39.0% |
|  | pp65Vac |  | 24.0% |
| 6 (A*0201) | Ub-R-pp65Vac | 6.7 | 37.4% |
|  | pp65Vac |  | 22.8% |

In the six representative experiments shown in Table II, four of which are HLA A 0201-specific, the amplification was 2.2–15 times greater using stimulation with Ub-R-pp65 as opposed to unmodified pp65. To demonstrate functional activity of the amplified T cells, aliquots of the same preparation used for flow cytometry were subjected to a chromium release assay using CMV-epitope-loaded autologous EBVLCL. The level of cytotoxicity increased for Ub-R stimulated cultures versus unmodified CMV pp65 stimulated cultures.

This study was repeated using 7–12 days of IVS. See Table III. Percent cytotoxicity to pp65 minimal cytotoxic epitopes A2 (NLVPMVATV; SEQ ID NO:3) and B7 ($pp65_{417-426}$; see Longmate et al., Immunogenetics 52:165–173, 2001) is shown. Strong cell proliferation was observed in cultures from three donors. Maximum cell expansions exceeded 150-fold, with an average of 107-fold. Amplified T-cells from PBMC cultures stimulated with either ubiquitinated or unmodified pp65-Vac constructs were consistently able to elicit specific lytic activity against autologous EVB-LCL targets sensitized with HLA-matched MCE peptides in all tested donors (Table III). IVS performed in cultures stimulated with Ub-R-pp65-Vac provided higher lytic activity than unmodified pp65-Vac in all donors ($p<0.05$). CRA performed on Ub-R-pp65-Vac cultures gave percentages between 41% and 91% while for pp65-Vac, the values varied between 28% and 74%. See Table III. The lysis percentages are shown at E:T ratios of 20, except for sample 4, which is reported at E:T=5. Fold T-cell increases are representative of each donor (sample).

TABLE III

Human T Cell Amplification by Antigen Presenting Cells Infected with Vaccinia Virus.

| Sample No. (HLA) | Vac Construct | Fold T Cell Increase | CMV-Specific Cytotoxicity |
|---|---|---|---|
| 1 (A*0201) | Ub-R-pp65Vac | 67 | 91 |
|  | pp65Vac |  | 66 |
| 2 (A*0201) | Ub-R-pp65Vac | 7 | 41 |
|  | pp65Vac |  | 28 |
| 3 (A*0201) | Ub-R-pp65Vac | 190 | 70 |
|  | pp65Vac |  | 40 |
| 4 (A*0201) | Ub-R-pp65Vac | 151 | 76 |
|  | pp65Vac |  | 66 |
| 5 (B*0702) | Ub-R-pp65Vac | 23 | 75 |
|  | pp65Vac |  | 46 |
| 6 (B*0702) | Ub-R-pp65Vac | 10 | 79 |
|  | pp65Vac |  | 74 |

TABLE III-continued

Human T Cell Amplification by Antigen
Presenting Cells Infected with Vaccinia Virus.

| Sample No. (HLA) | Vac Construct | Fold T Cell Increase | CMV-Specific Cytotoxicity |
|---|---|---|---|
| 7 (B*0702) | Ub-R-pp65Vac | 65 | 72 |
| | pp65Vac | | 42 |
| 8 (B*0702) | Ub-R-pp65Vac | 340 | 55 |
| | pp65Vac | | 41 |

Autologous CMV-specific CTL may be administered to a patient in need thereof, such as a bone marrow transplant patient, for adoptive transfer of immunity, according to any convenient method known in the art.

Example 15

IFN-γ Release and Tetramer Binding

Figure 21A:
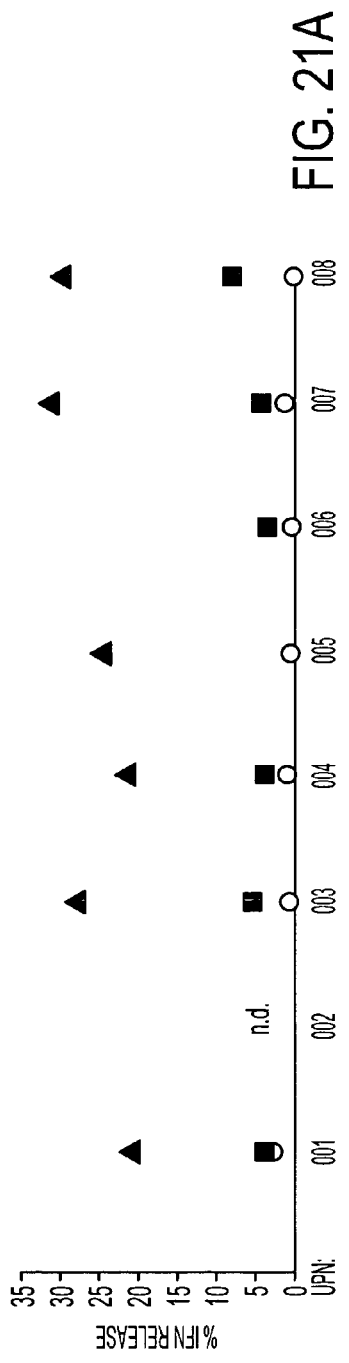
FIG. 21 shows IFN-γ release (A) and tetramer reagent binding (B) for Donors listed in Table III.
FIG. 21C shows representative FACS (tetramer binding) plots for Donor 001. See Example 15.

Donors listed in Table III were tested for specific CD8+ IFN-γ production using ICC before (open circles) and after IVS with pp65-Vac (filled squares) or Ub-R-pp65-Vac (filled triangles). Peptides used in ICC were P53$_{149-157}$ and pp65$_{495-503}$ (SEQ ID NO:3) with HLA A*0201 donors and pp65$_{417-426}$ with HLA B*0702 donors. Donor 2 (sample 2) was not tested while for Donor 5 (sample 5), ICC was performed only after Ub-R-pp65-Vac IVS. For each sample, % CD8+ IFN-γ release to irrelevant peptide was substracted from total release. See FIG. 21A. IFN-γ production between 21% and 31% was detected in cultures stimulated with UB-R-pp65-Vac, a much higher level than with pp65-Vac (between 3% and 8%, p<0.05). Nonetheless, the difference in IFN-γ levels before and after pp65-Vac IVS were significant (p<0.05; see FIG. 21A).

Figure 21B:
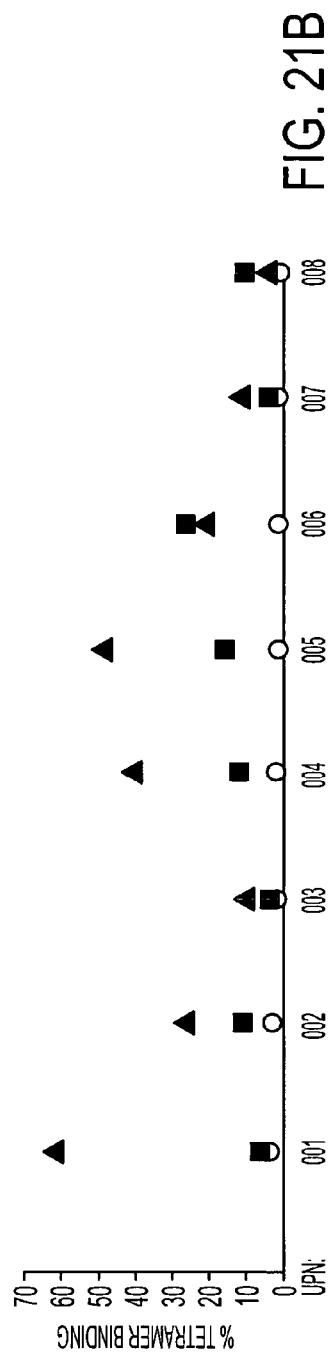

CMV pp65$_{495-503}$ tetramer was used with HLA A*0201 donors, CMV pp65$_{417-426}$ with HLA-B*0702 donors, and the non-related HIV POL$_{464-472}$ was used as control tetramer for each donor. CD8+ binding percentages to control tetramer (0.07–0.1%) were subtracted in each case. See FIG. 21B. Open circles denote CD8+ tetramer binding percentages in donor PBMC before IVS, filled squares after pp65-Vac IVS, and filled triangles after Ub-R-pp65-Vac IVS. Binding to CMV-pp65-specific tetramers was significantly enhanced (p<0.05) following IVS with both ubiquitinated and unmodified pp65. See FIG. 21B. Six out of 8 donors had higher tetramer binding following IVS with Ub-R-pp65-Vac than with pp65-Vac (p<0.05 for the whole population). In IVS cultures performed with Ub-R-pp65-Vac, the CMV specific tetramer frequency was higher (average 22.4 fold) versus pp65-Vac (average 9.9 fold) compared to the respective fresh PBMC. In one representative example, see FIGS. 21B and 21C, a marked tetramer frequency difference (10 fold) was found between Ub-R and native forms of pp65. These results may reflect an advantage of Ub-R-pp65-Vac for rapid amplification of CMV-specific T-cells to be used in adoptive transfer.

Figure 21C:
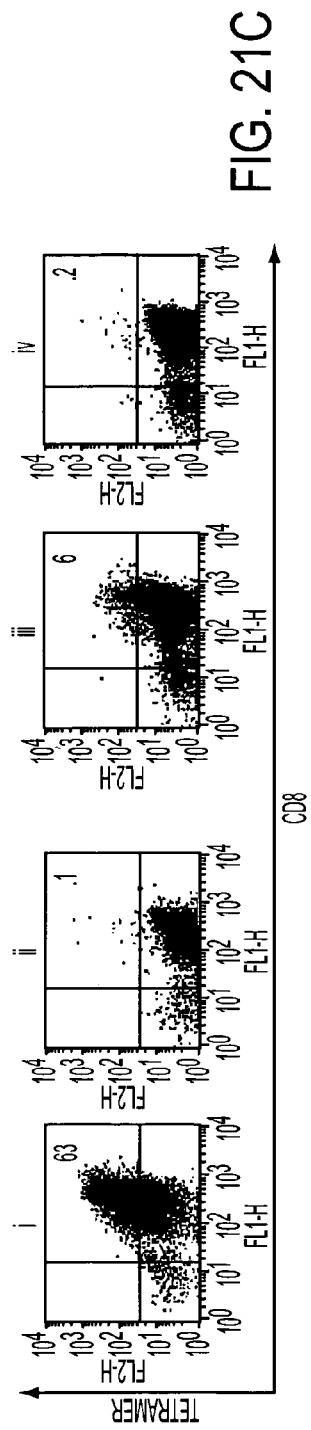

FIG. 21C shows Donor 1 (sample 1) tetramer binding FACS plots. Two-color FACS" was employed using anti-CD8 FITC-labeled mAB and tetramer conjugated with PE. Numbers on the upper right quadrant indicate CD8+ T cell percentages to (i) pp65$_{495-503}$ tetramer, (ii) HIVpol$_{464-472}$ control tetramer, after Ub-R-pp65-Vac IVS, (iii) pp65$_{495-503}$ tetramer, and (iv) HIVpol$_{464-472}$ control tetramer, after pp65-Vac IVS.

Example 16

Lytic Activity, IFN-γ Release and Tetramer Binding in pp65/pp150-MVA and IE4-MVA IVS Cultures Robust cytotoxicity to autologous EBV-LCL targets loaded with the relevant immunodominant HLA epitope peptides was found in all donors after IVS. See FIG. 22A. pp65 tetramer detected the amplified population of CMV-y specific T-cells (19–39 fold) after IVS. See FIGS. 22B and 22C. In addition, IFN-production by CD8+ T cells measured by ICC, substantially rose (9–13 fold) in the tested subjects. See FIG. 22C. Among three HLA A*0201 donors, donor UPN011 was the only one to have HLA allele A*0301, for which a CTL epitope (pp150$_{945-944}$) has been described. Following IVS, lytic activity against targets pulsed with this peptide was remarkable, see FIG. 22A, and 2.4% of the CD8+ T cells were IFN-γ+by ICC (>8-fold higher than fresh PBMC, data not shown), which confirmed that pp150 expressed in MVA was promoting specific recognition. In contrast to the differences in IVS activity between pp65-Vac and Ub-R-pp65-Vac, Ub-R-pp65-MVA did not increase cytotoxicity, IFN-γ production, or tetramer binding versus pp65/pp150-MVA in both HLA A*0201 and HLA B*0702 donors (data not shown).

Figure 22A:
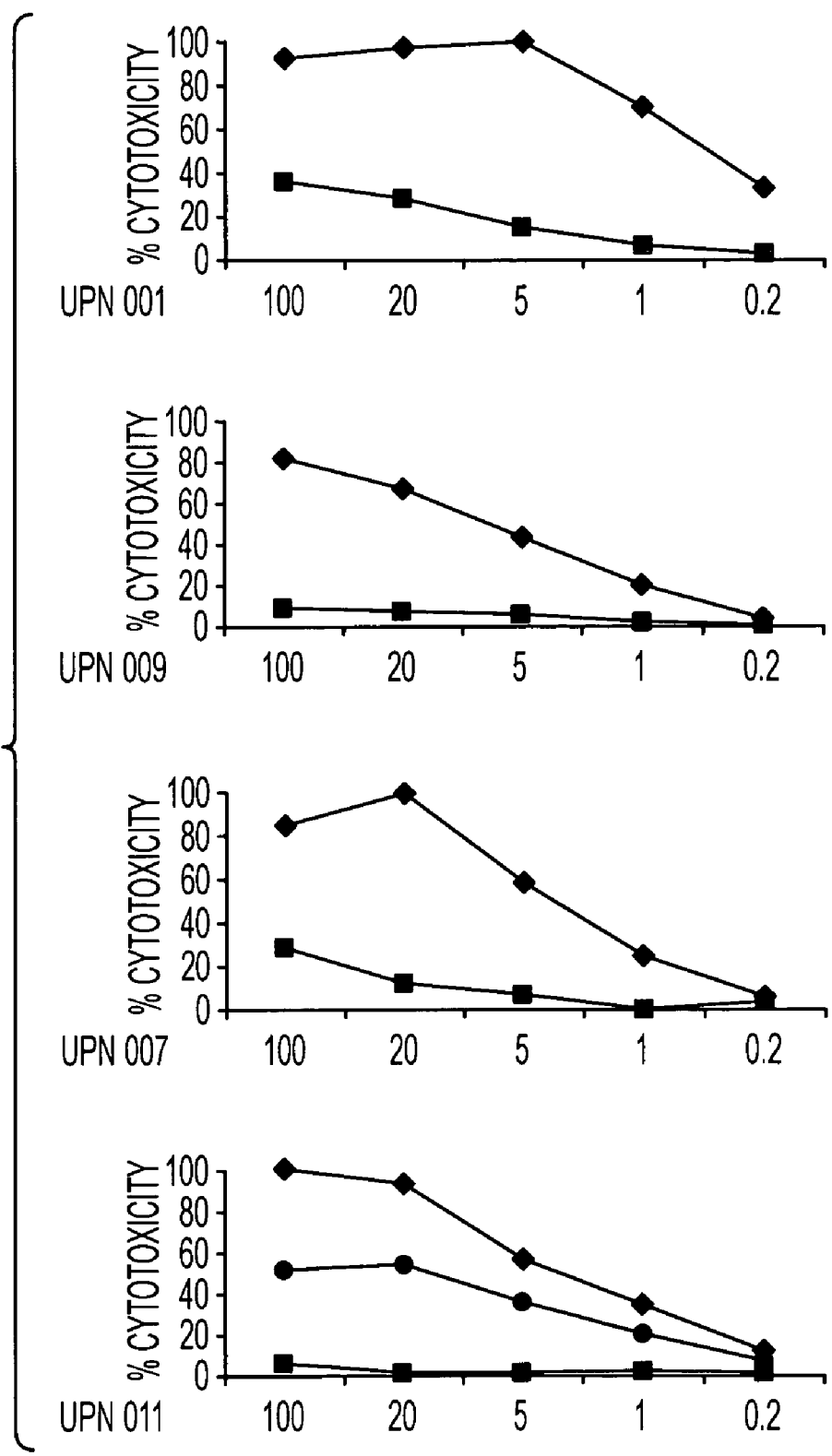
FIG. 22 shows cytotoxicity for four donors to autologous EBV-LCL targets (A; ■ indicates background lysis to autologous LCL loaded with p53$_{149-157}$; ◆ indicates lysis of autologous LCL pulsed with pp65$_{495-503}$, (donors 001, 009, 011), or pp65$_{417-426}$ for donor 007; ● indicates lysis of pp150$_{945-955}$ pulsed autologous LCL of donor 011), tetramer binding for those same donors (B; CD8⁺ cells from fresh PBMC (○) and pp65/pp150-MVA IVS cultures (●)) and IFN-γ release for those same donors (C; CD8⁺ cells of fresh PBMC (○) and pp65/pp150-MVA IVS cultures (●) detected in ICC). See Example 16. pp65$_{495-503}$ tetramers were used for donor 001, 009 and 011, while donor 007 was tested using pp65$_{417-426}$ tetramers. CD8⁺ T cell binding to HIV pol$_{464-472}$ tetramers was substracted. Peptides used during ICC incubation were p53$_{149-157}$ and pp65$_{495-503}$ for HLA A*0201 donors and pp65$_{417-426}$ for HLA A*0702 donor 007. For each donor, percentages of IFN-γ CD8⁺ cells to irrelevant P53$_{149-157}$ peptide were subtracted from the corresponding specific values.
Figure 22B:
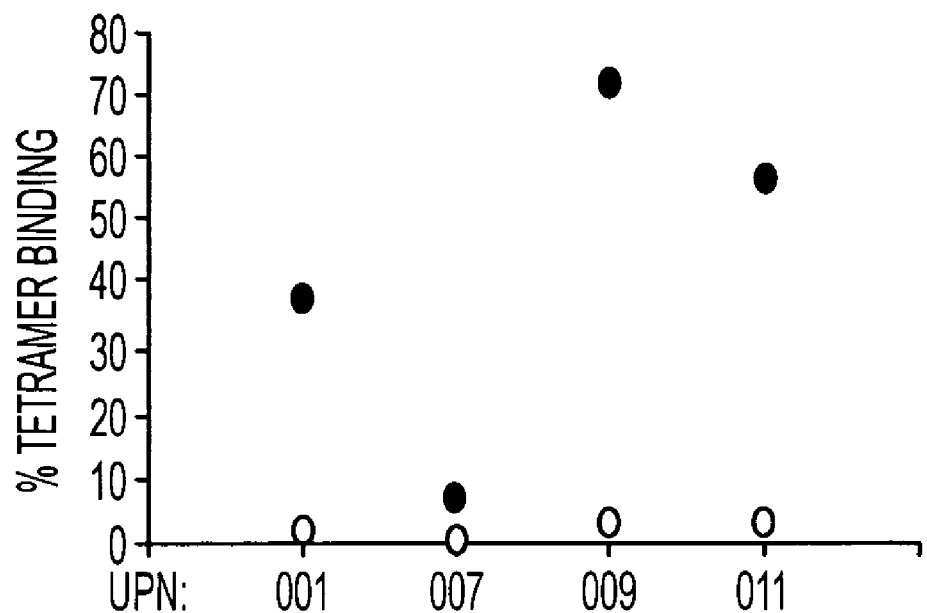
Figure 22C:
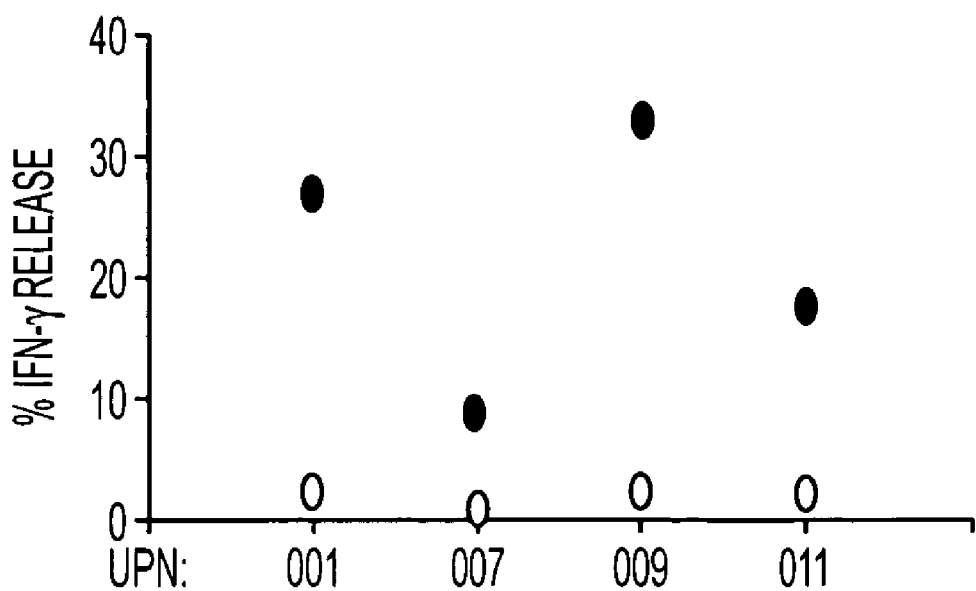
Figure 23A:
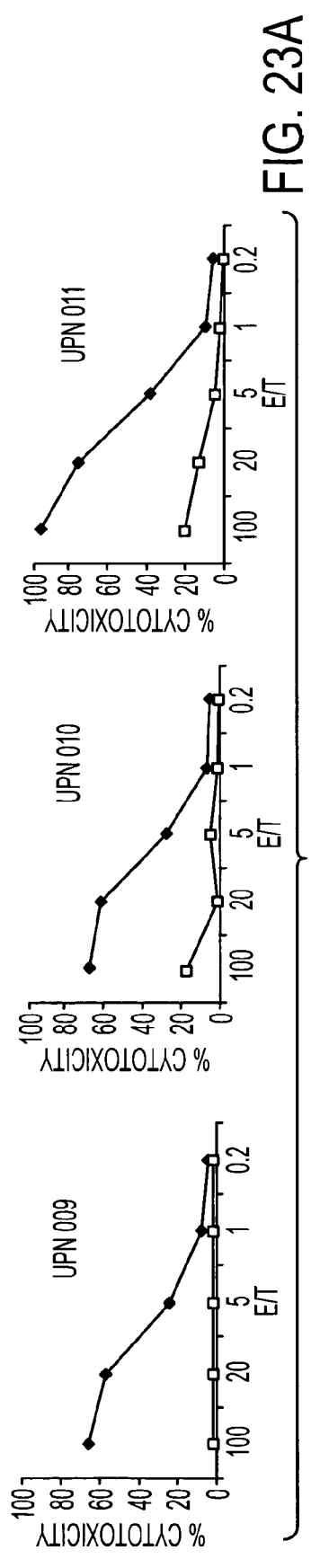
FIG. 23 shows cytotoxicity (A), tetramer binding and IFN-γ release (B) for three donors.
FIG. 23(C) shows Donor 009 tetramer binding FACS plots. See Example 16.
Figure 23B:
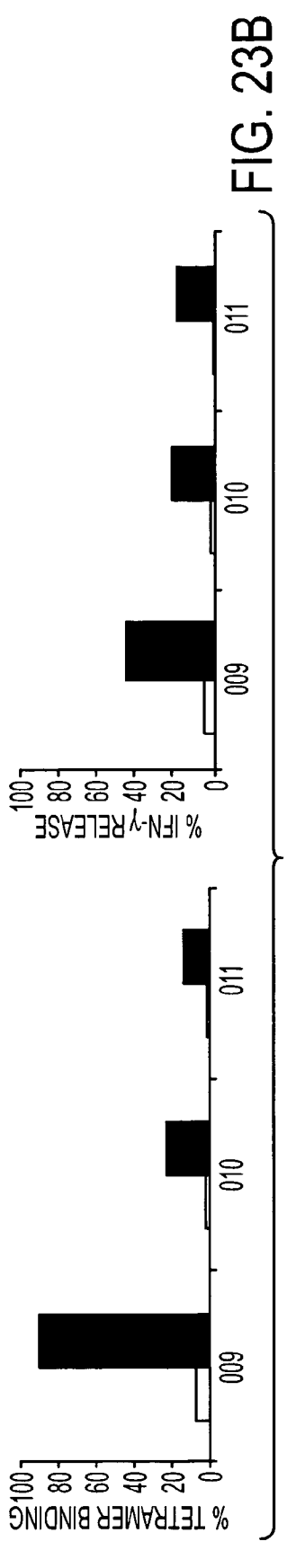
Figure 23C:
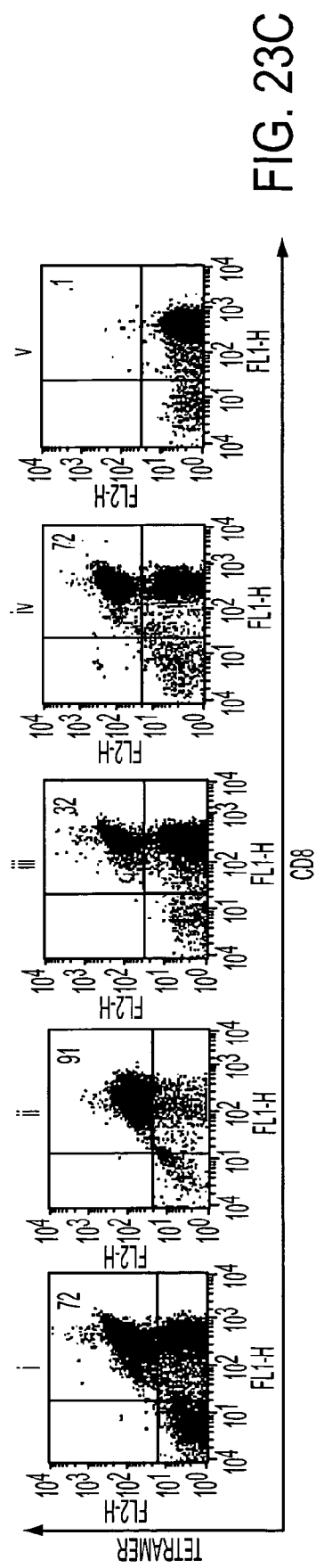

The IE1$_{316-324}$ T-cell clone lysed HLA A*0201 EBV-LCL targets infected at m.o.i. of 10 with IE4-MVA (45% at E/T 3) or with Ub-R-IE4-MVA (78% at E/T 3). rMVA were subsequently evaluated in IVS with PBMC from 3 CMV-positive HLA A*0201 donors (UPN 009, 010, 011, FIG. 23A-C). PBMC from UPN 009 and 011 were previously analyzed using pp65/pp150-MVA and UbRpp65-MVA (FIG. 22A-C). IE4-MVA used in a 7–12 day IVS promoted substantial T cell expansion (<68-fold). In all three donors, IE4-MVA was able to elicit strong specific cytotoxicity against autologous EBV-LCL targets pulsed with IEI$_{316-324}$ peptide (FIG. 23A). An increase (12.2-fold average) in the percentages of specific IEI$_{316-324}$ tetramer binding and IFN-γ production (13.8-fold average) was observed (FIGS. 23B and C). Very similar results were found using Ub-R-IE4-MVA in IVS cultures from all three donors (data not shown).

Whether CMV-CTL could be expanded from PBMC simultaneously using pp65/pp150-MVA and IE4-MVA or their ubiquitinated versions (Ub-R-pp65-MVA and Ub-R-IE4-MVA) in the same subject was evaluated. Both rMVA was used at an m.o.i. of 2.5, in order to duplicate the same m.o.i. of 5 employed for the IVS performed with single viruses. The objective of eliciting an amplified mCTL response simultaneously to CMV-IEI and pp65 was achieved in all three HLA A*0201 donors, following IVS with a mixture of both pp65/pp150-MVA and IE4-MVA (Table IV). As expected, donor 011 also amplified pp150-specific CTL (data not shown) to comparable levels using pp65/pp150-MVA (FIG. 22A). After 12 days of IVS, massive cell proliferation, producing between 3–5×10$^8$ cells, was obtained for donors 009 and 010, while 3×10$^7$ cells were recovered for donor 011. For UPN 009 and 010, the degree of cell expansion after the combination IVS was about 1 log higher than after the IVS with IE4-MVA only, while for 011 it was similar. After combination IVS, cytotoxicity was robust against IEI$_{316-324}$ and pp65$_{595-503}$ in all donors (Table V). Tetramer binding of PBMC from donor 009 stimulated with either pp65-MVA or IE4-MVA or with the combination of 2 rMVA (FIG. 23C) showed similar high levels of expansion. Ub-R-pp65-MVA and Ub-R-IE4-MVA combined in the same IVS for all three donors gave comparable tetramer and IFN-$\gamma^+$ T cell percentages to those obtained with unmodified rMVA used in combination (data not shown). These data demonstrate the feasibility of simultaneously expanding separate CMV mCTL populations in the same individual.

Cytotoxic activity detected after IVS for each donor is shown in FIG. 22A. Shaded squares indicate background lysis to autologous EBV-LCL loaded with $p53_{149-157}$; filled diamonds indicate lysis of autologous EBV-LCL pulsed with $pp65_{495-503}$, (donors 001, 009, 011), or $PP65_{417-426}$ for donor 007; filled circles indicate lysis of $pp150_{945-955}$ pulsed sutologous EBV-LCL of donor 011. FIG. 22B shows tetramer binding levels in $CD8^+$ cells from fresh PBMC (open circles) and pp65/pp150-MVA IVS cultures (filled circles). $pp65_{495-503}$ tetramers were used for donor 001, 009 and 011, while donor 007 was tested using $pp65_{417-426}$ tetramers. $CD8^+$ T cell binding to HIV $pol_{464-472}$ tetramers was subtracted. FIG. 22C shows percentage IFN-$\gamma$ release from $CD8^+$ cells of fresh PBMC (open circles) and pp65/pp150-MVA IVS cultures (filled circles) detected in ICC. Peptides used during ICC incubation were P53149–157 and $pp65_{495-503}$ for HLA A*0201 donors and $pp65_{417-426}$ for HLA A*0702 donor 007. For each donor, percentages of IFN-$\gamma$ $CD8^+$ cells to irrelevant $P53_{149-157}$ peptide were subtracted from the corresponding specific values.

Cytotoxic activity, detected after IVS, are shown in FIG. 23A for each donor. Shaded squares indicate background lysis to autologous EBV-LCL loaded with $p53_{149-157}$; filled diamonds indicate lysis of autologous EBV-LCL pulsed with HLA A*0201 $IE1_{316-324}$ peptide. $IE1_{316-324}$ tetramer binding frequencies in $CD8^+$ T cells from donor PBMC (open bars) and IE4-MVA IVS cultures (filled bars) are shown in FIG. 23B, left panel. $CD8^+$ T cell binding to HIV $Pol_{465-472}$, used as control, was subtracted. In FIG. 23B, right panel, percentages of $CD8^+$ with IFN-$\gamma$ release after incubation with $IE1_{316-324}$ peptide in fresh PBMC (open circles) or IE4-MVA IVS cultures (filled circles) were detected using ICC. Percentage of $CD8^+$ T cells with IFN-$\gamma$ release to $P53_{149-157}$ was subtracted. FIG. 23C shows donor 009 tetramer binding FACS plots. Tetramers used were conjugate with APC, and with PE for plot ii. Numbers on the upper right quadrant indicate $CD8^+$ T cell tetramer binding percentages to (i) $pp65_{495-503}$ tetramer, after pp65/pp150-MVA IVS; (ii) $IEI_{316-324}$ tetramer, after IE4-MVA IVS; (iii) $pp65_{495-503}$ tetramer; (iv) $IEI_{316-324}$ tetramer; and (v) HIV $pol_{464-472}$ control tetramer after combined pp65/pp150-MVA and IE4-MVA IVS.

Example 17

PCR Detection of Wild Type Virus

Since insertion of foreign genes generally attenuates MVA compared to wild type, residual wild type contaminating MVA may be detected. PCR detection is more sensitive than screening methods requiring physical separation for distinguishing wild type from rMVA. Total nucleic acid was prepared from cell lysates according to standard methods as described by Zhang and Moss, *Proc. Acad. Natl. Acad. Sci. USA* 88:1511–1515, 1991. PCR analysis using primers that flank the DNA insertion site distinguish wild type from recombinant virus by the length of the fragment generated. Primers were made corresponding to the sequence in the left (fl1) and right (fl2) flanks of delII contained in vector pLW22. The sequence of the sense primer from fl1 was 5'-tgcatttaaggcggatgtc-3' (SEQ ID NO:4) and the antisense primer was 5'-caagcggcctctgataccc-3' (SEQ ID NO:24). Using theses primers, the presence of wild type virus generated a fragment of about 500 bp, whereas the insertion of foreign plasmid-derived DNA sequences between fl1 and fl2 of delII created a much larger fragment which usually is not detectable using this method. The absence of the approximately 500 bp fragment indicates that the preparation is not contaminated with wild type virus. Similar primers were designed for delIII using the same logical design (SEQ ID NO:6 and SEQ ID NO:7).

Example 18

Measurement of Protein Expression by ELISA

Protein expression was measured in culture medium by ELISA as follows. Although the example was performed to detect CMV gB(s), the methods can be used for any desired CMV protein. A 96-well Costar® microtiter plate was coated with an affinity purified murine monoclonal antibody that specifically recognizes gB, diluted in PBS (1 µg antibody per well) and incubated at 37° C. The plate was washed with PBS containing 0.05% TWEEN 20 (washing buffer) and blocked with PBS containing 2% BSA, 0.05% TWEEN 20 at 37° C. The plate was incubated overnight at 4° C. with culture media collected from rCMV-infected CEF. The plate was then washed and incubated with purified human anti-CMV IgG at 37° C., followed by incubation with 1:50,000 diluted goat anti-human IgG conjugated with peroxidase (Sigma) at 37° C. The plate was developed with 1 mg/ml O-phenylenediamine. The reaction was stopped with 4 M $H_2SO_4$ and read at 490 nm with a microplate reader.

Example 19

CMV aB Protein Vaccine Production

A cDNA encoding a gB protein that initiates at amino acid 1 and is 680 amino acids in length (soluble gB, (gB(s)), also known as $gB_{680}$) was used to develop an expression construct. This expressed protein incorporates all of the important neutralizing domains, including AD1 and AD2, but is deleted of amino acids 681–907, including the transmembrane region. This cDNA was cloned into pLW51 transfected into MVA-infected CEF cells and purified directly on CEF monolayers as described above. After three screening rounds using color for GUS expression, three simultaneous 6-well CEF plates were made for each of ten isolates. One set was screened for gus and one immunostained for gB expression with or without fixation. If gB-stained plaques are more numerous than gus-mediated blue plaques, this indicates that the bacterial gus gene was deleted while the gB gene was maintained.

Figure 24A:
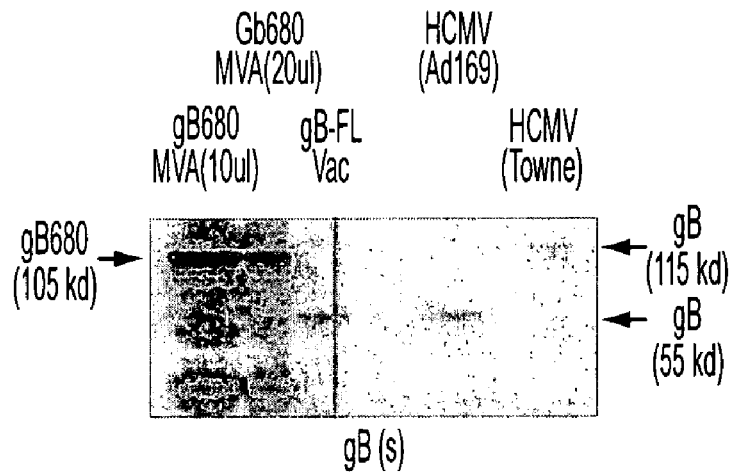
FIG. 24A is a western blot showing expression of gB(s) from rMVA.
Figure 24B:
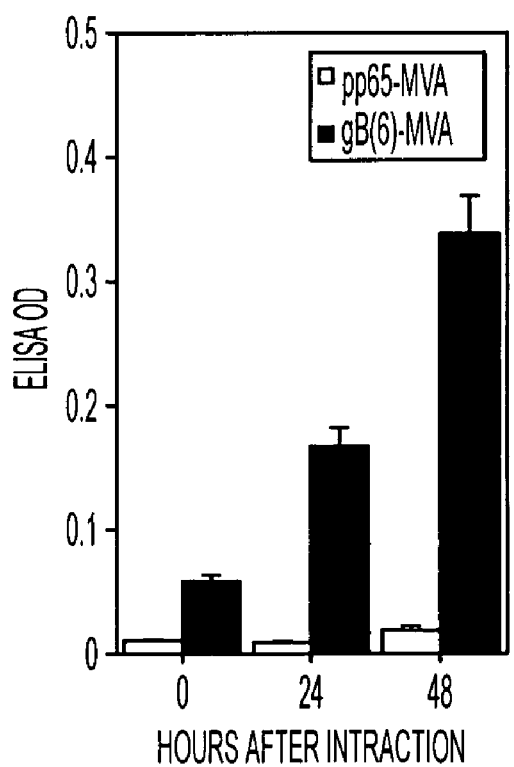
FIG. 24B is a bar graph showing results of an ELISA demonstrating secretion of gB(s).

The expression of gB(s) was very robust, as shown by western blot in FIG. 24A. A larger 115 kd protein is seen in the gBVac lanes and the processed 55 kd protein also is seen in the CMV and Vac lanes, but, as expected, not in the MVA lanes. Since the protein is secreted, the media of CEF infected with MVA was tested for gB(s) by ELISA. A parallel infection using pp65-MVA was conducted to establish the specificity of the assay. Results, shown in FIG. 24B, show that gB(s) is produced and secreted in significant quantities.

Example 20

Immunization of Balb/c Mice with gB(s)-rMVA gB(s)-rMVA used for immunization was purified by sucrose density ultracentrifugation, titrated and stored at −80° C. in PBS containing 5% lactose. Balb/c mice (Jackson Laboratories, Bar Harbor, Me.) at 6 to 8 weeks of age were injected with $5 \times 10^7$ pfu purified gB(s)-rMVA (100 µl volume) by three different routes (intraperitoneal (IP), intramuscular (IM), or subcutaneous (SC)). See Table IV, below. All animals were boosted three weeks after initial immunization with the same dose by the same route. Blood samples were collected from the orbital plexus of the mouse using microhematocrit tubes at 3 (prior to boosting), 6 and 12 weeks after initial immunization. Blood was allowed to clot for one hour at 37° C. Sera then were removed from the clot and stored at −20° C.

TABLE IV

Immunization Schedule.

| Mice | Group | No. of Mice | Route | Dosage | Time |
|---|---|---|---|---|---|
| 6–8 weeks | 1 | 3 | IP | $5 \times 10^7$ pfu | 3 months |
| Balb/c | 2 | 5 | IM | $5 \times 10^7$ pfu | 3 months |
|  | 3 | 3 | SC | $5 \times 10^7$ pfu | 3 months |
|  | 4 | 4 | NONE | NONE | 3 months |

Figure 25:
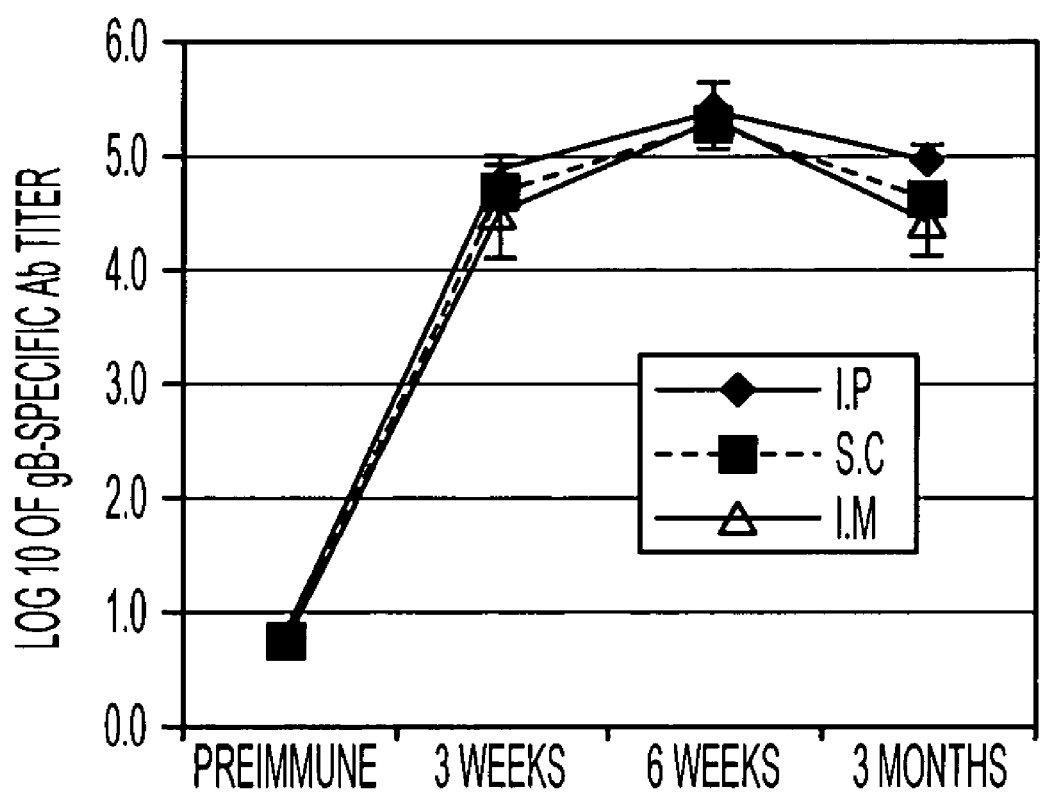
FIG. 25 shows the $\log_{10}$ of the gB-specific antibody titer of sera from pre-immune and immunized mice, immunized by different indicated routes with gB(s)-rMVA.

The sera were tested by ELISA using affinity-purified HCMV gB(s) protein. The gB(s) protein was diluted in 0.1 M carbonate-bicarbonate buffer (pH 9.0) and coated onto 96-well flat-bottom microplates (Costar®) at 100 ng protein per well at 4° C. overnight. The plates were washed three times with PBS containing 0.05% TWEEN 20 (washing buffer) and blocked with PBS containing 2% BSA and 0.05% TWEEN 20 for one hour at 37° C. The plates were incubated with pre-and post-immune sera, serially diluted in PBS at 37° C. for one hour. The plates were incubated for thirty minutes with 1:1000 goat anti-mouse IgG conjugated with peroxidase (Sigma"), followed by three washes with washing buffer. Color was developed for 15 minutes using 1 mg/ml O-phenylenediamine in 0.1 M citrate-phosphate buffer, pH 5.0 with 0.015% $H_2O_2$. The reaction was stopped by addition of 4M sulfuric acid and plates were read at 490 nm with a microplate reader (DYNEX Technologies, Inc. VA). Optical density (OD) readings greater than the geometric mean OD plus three standard deviations of pre-immune mouse sera were considered positive. gB(s) antibody titers were calculated from individual mice immunized as shown in Table IV above. Measurements were repeated three times and the average $\log_{10}$ reciprocal titer is shown in FIG. 25. In all cases, the booster immunization enhanced the IgG titer. No measurable titer was found in pre-immune sera from four separate mice at 1:50 dilution (data not shown).

The IgG titers were remarkable; only in cases when proteinaceous gB was administered in strong adjuvant or with use of dense bodies have comparable IgG titers been reported. Because the IgG titers were so high, neutralizing titer was assayed. Neutralization assays were performed using human MRC-5 fibroblast cells according to known methods established in the art. Andreoni et al., *J. Virol. Meth.* 23:157–167, 1989; Gonczol et al., *J. Virol. Meth.* 14:37–41, 1986.

Figure 26:
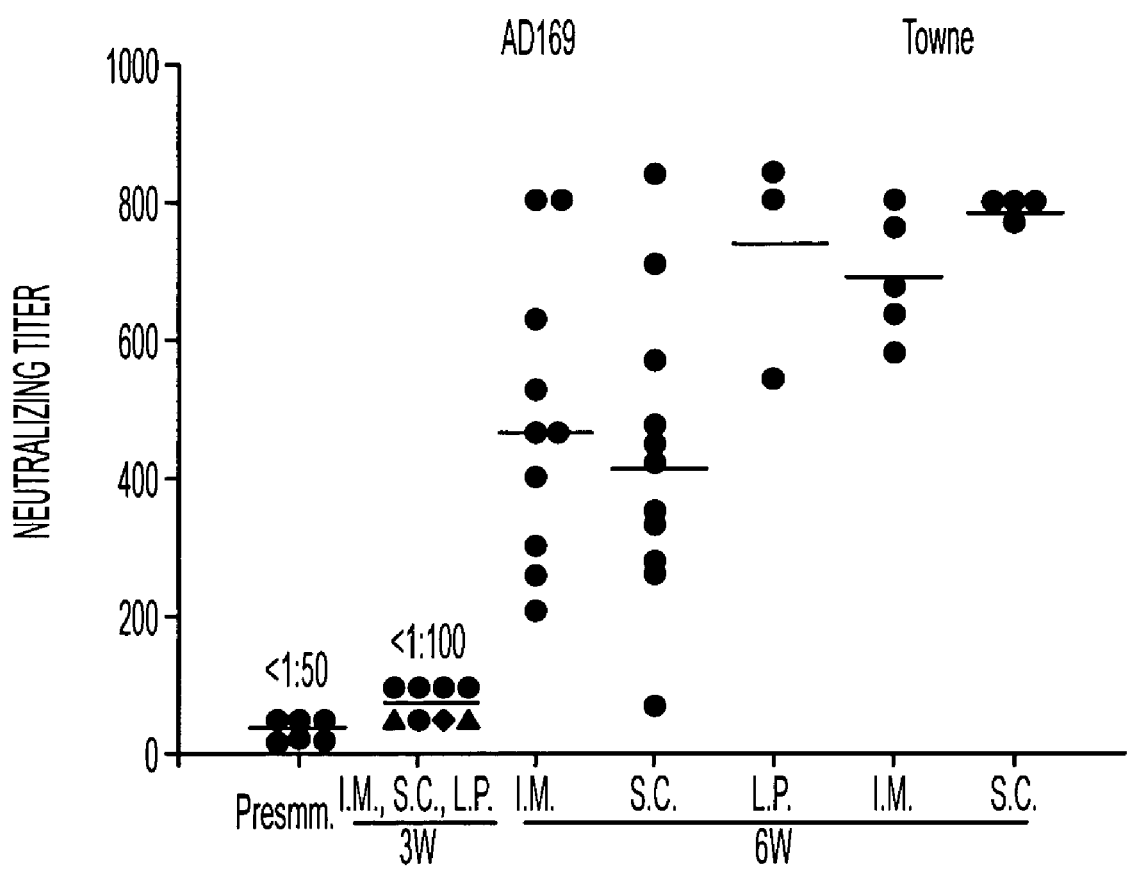
FIG. 26 shows the neutralizing titer of mice sera using human MRC-5 fibroblast cells and AD169 Towne Strain.

Sera from mice immunized either once (3 W) or twice (6 W) as described above were diluted in medium and incubated with titered input of CMV (AD169 or Towne strain) for 60 minutes. The virus stock was titered to infect 100 nuclei per well. MRC-5 fibroblast monolayers seeded into wells of a 96-well flat-bottom microtiter plate were incubated for four hours with sera plus virus, without complement. After washing, the plates were further incubated for 16 hours in medium. Cells were fixed in ethanol, rehydrated and reacted with an IE1-specific monoclonal antibody (p63-27), followed by a FITC-coupled secondary goat anti-mouse IgG, and counterstained with Evans Blue before counting fluorescent nuclei under a fluorescence microscope. Each determination was done in duplicate wells. Fifty percent neutralizing titers were calculated using the Reed-Muench method and presented in FIG. 26. Individual mice are shown as dots, with horizontal lines indicating the mean of the group. All mice in a group (IM, SC or IP) were immunized on the same day. Controls included pre-immune mouse sera and a positive control anti-gh monoclonal antibody that gives high titer CMV-neutralization. These data indicate a robust humoral immune response to gB(s), and a higher level of neutralizing titer against CMV than other approaches. Notably, two distinct strains of CMV containing either form gB were effectively neutralized, indicating that the antibodies stimulated by this vaccine compound recognize more than just the homologous virus.

Example 21

Immunization of Transgenic HLA A2/Kb Mice

Figure 27A:
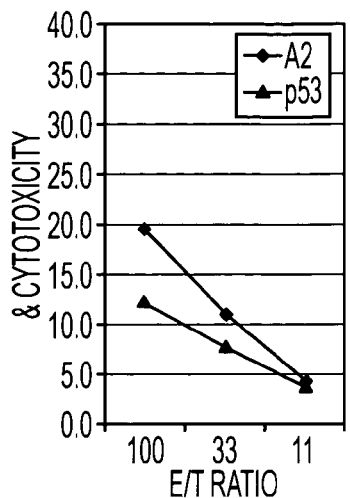
FIG. 27 shows CTL activity of splenocytes from HLA A2/Kb transgenic mice immunized with pp65Vac (FIG. 27A), Ub-M-pp65Vac (FIG. 27B) and Ub-R-pp65Vac (FIG. 27C) for A2 peptide (SEQ ID NO:3) or an irrelevant peptide (p53).
Figure 27B:
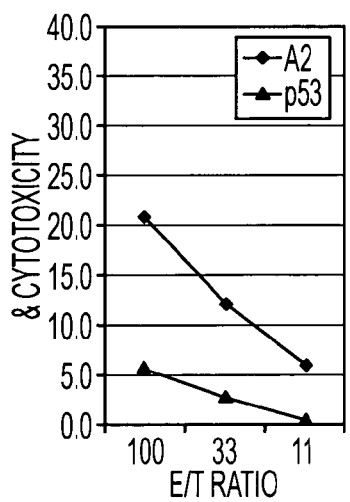
Figure 27C:
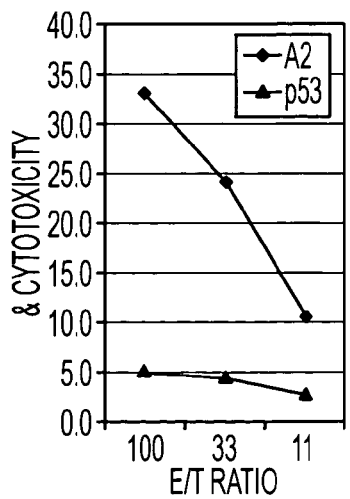

Three forms of pp65 expressed in Vac (unmodified, Ub-R or Ub-M) were evaluated for eliciting cytotoxic T cell activity specific to CMV in transgenic HLA A2/Kb transgenic mice. A single immunization of 10 million plaque-forming units of each form of pp65 was expressed in Vac as described above. After three weeks, splenocytes were harvested as described in the prior art and assayed for recognition of the $pp65_{495-503}$ epitope (SEQ ID NO:3) by chromium release assay. FIG. 27 presents the results of this assay. An unrelated epitope, human $P53_{149-157}$ (p53) was used as a control for each of the three constructs. Consistent with the results shown above, Ub-R-pp65Vac (FIG. 27C) showed the most CTL activity. Ub-M-pp65Vac (FIG. 27B) and unmodified pp65Vac (FIG. 27A) were similar to each other.

Figure 28:
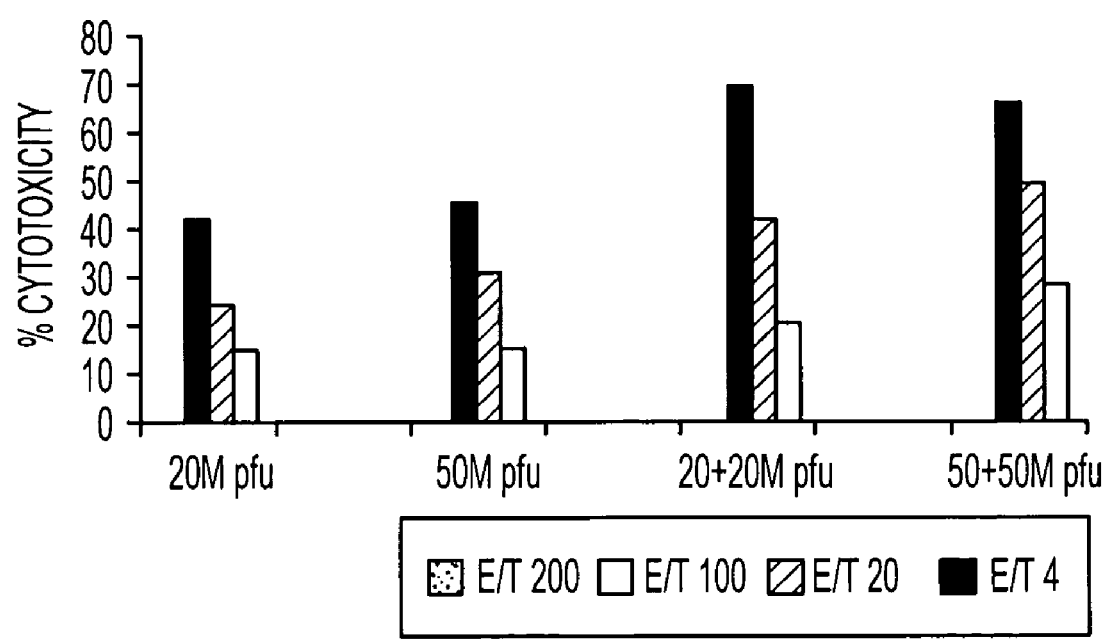
FIG. 28 provides cytotoxicity results for murine splenocytes immunized with rMVA carrying a pp65 antigenic sequence against T2 target cells loaded with SEQ ID NO:3.

Immunization of transgenic HLA A2/Kb mice with recombinant MVA intraperitoneally also has been successful and boosters are effective. HLA A2/Kb mice were immunized as indicated in FIG. 28 with rMVA (one or two immunizations) and euthanized three weeks after the last injection. A single in vitro stimulation with the $pp65_{495-503}$ CTL epitope (SEQ ID NO:3) was carried out and cytotoxicity of the spleen cells against human T2 target cells loaded with SEQ ID NO:3 was determined. HLA A2/Kb mice processed the pp65 protein expressed from MVA so that spleen cells recognized a processed CTL epitope derived from pp65. Equally important is the result that a second booster immunization gave an improved response. Immunogenicity of pp65MVA was similar to pp65Vac, showing that rMVA is effective without being infectious, since mice are non-permissive for MVA viral assembly. Successful recognition of a human CTL epitope by immune splenocytes in this well-recognized murine model of human immune responses demonstrates the effectiveness of vaccination with rMVA expressing CMV genes.

Example 22

HHDII Mouse Immunization Studies

Figure 29:
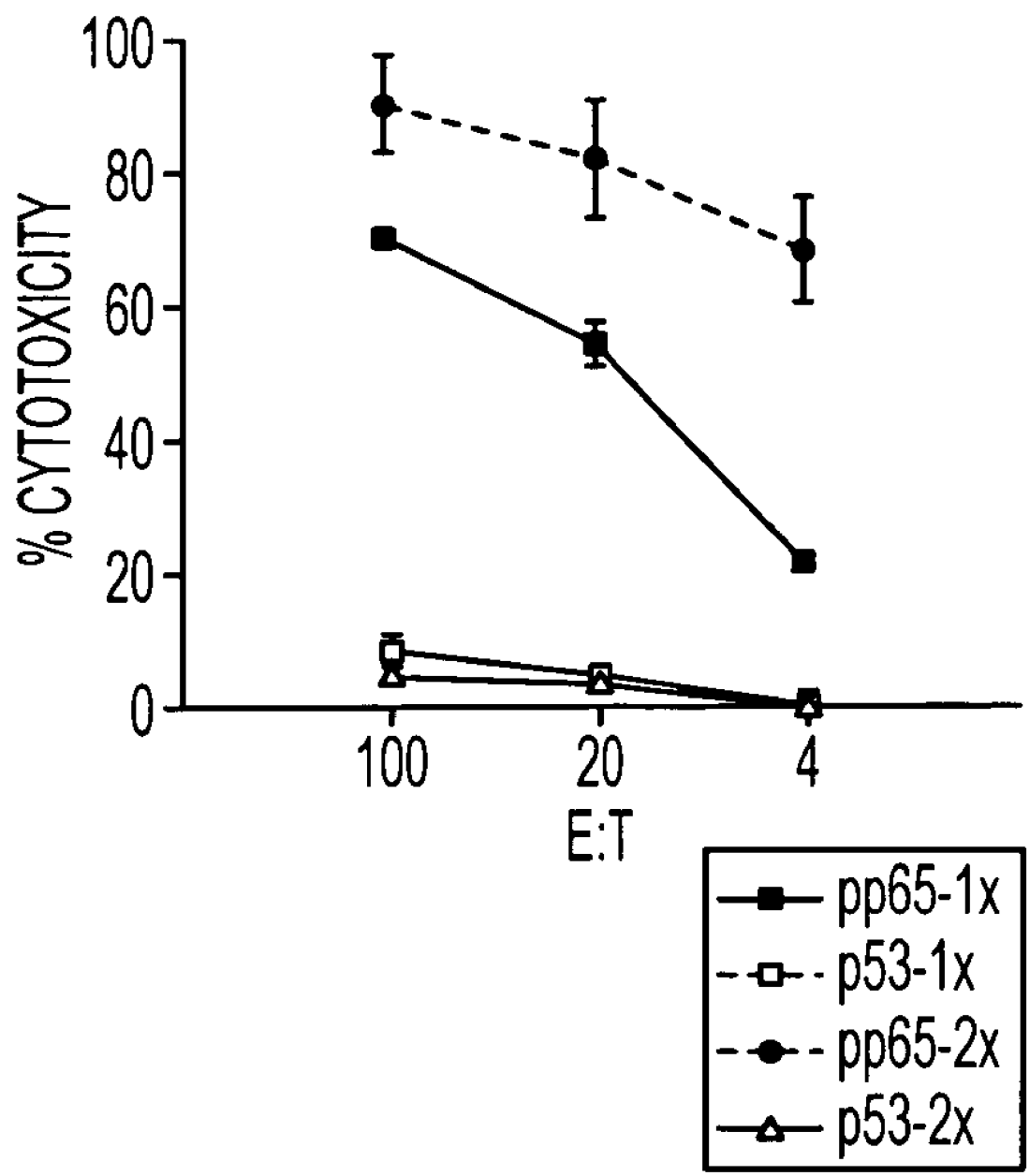
FIG. 29 shows cytotoxicity of splenocytes from HHDII mice immunized with pp65-MVA once (1×) or twice (2×) against T2 target cells loaded with SEQ ID NO:3.

HHDII mice are knock-out mice that do not have murine-specific Class I presentation and that have only one expressed classic Class I gene: the HLA A2.1/Kb transgene connected to B2-M. Four HHDII mice were immunized with 20 million plaque-forming units of pp65-MVA and two of these were immunized a second time three weeks later with the same virus. Three weeks after the last immunization, the mice were euthanized and the spleens removed. The splenocytes were stimulated in vitro with targets expressing the pp65$_{495-503}$ CTL epitope according to known methods. Cytotoxicity of the splenocytes against T2 cell targets loaded with the pp65$_{495-503}$ CTL epitope is shown in FIG. 29. Mice were able to process the pp65 protein expressed from MVA such that their spleen cells recognized the human CTL epitope pp65$_{495-503}$. In addition, the pp65-rMVA vaccine booster effectively increased the cytotoxic response, providing a synergistic response, which cannot be achieved with Vac constructs. See FIG. 29 for results of the cytotoxicity assay using immune splenocytes from HHDII mice immunized once (1×) or twice (2×) with pp65-MVA and T2 target cells that express a human pp65 CTL epitope, SEQ ID NO:3.

Example 23

HHDII Mice Immunization With rMVA

Figure 30A:
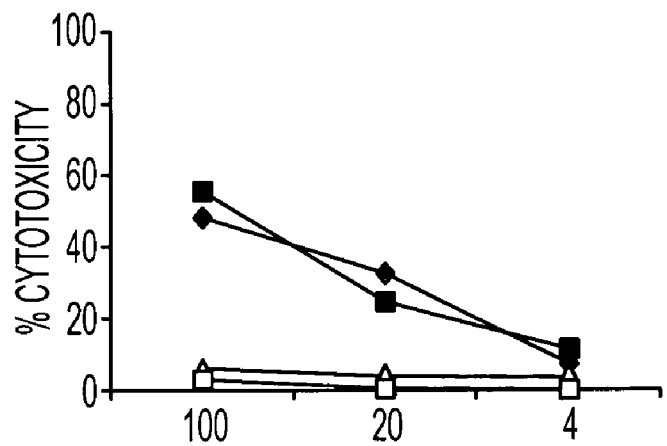
FIG. 30 shows cytotoxicity results for HHDII mouse splenocytes. See Example 23. Filled symbols show killing of T2 targets loaded with a pp65 or IE peptide; open symbols indicate killing of the same targets loaded with $p53_{149-157}$.
Figure 30B:
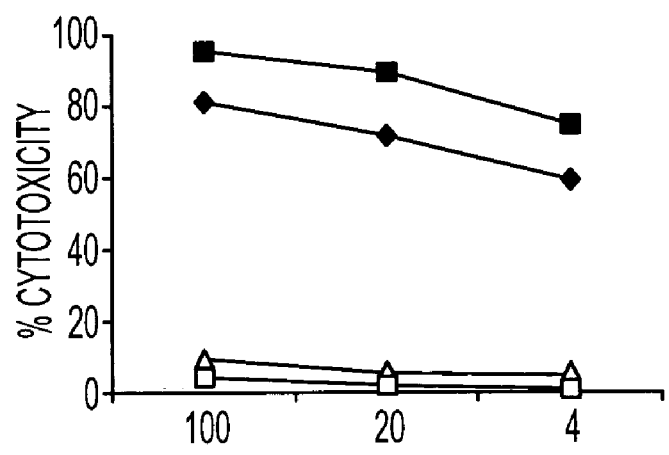
Figure 30C:
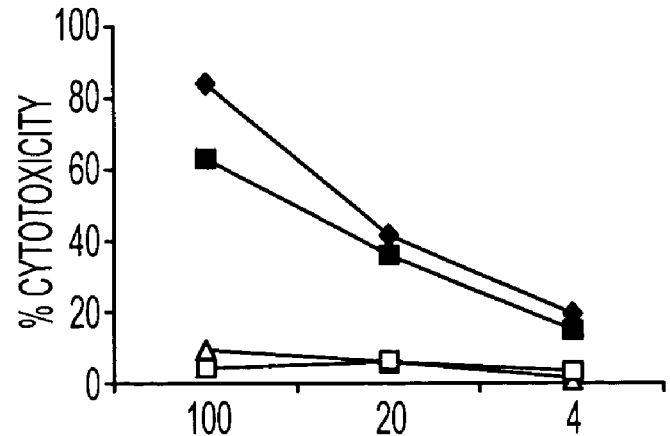
Figure 30D:
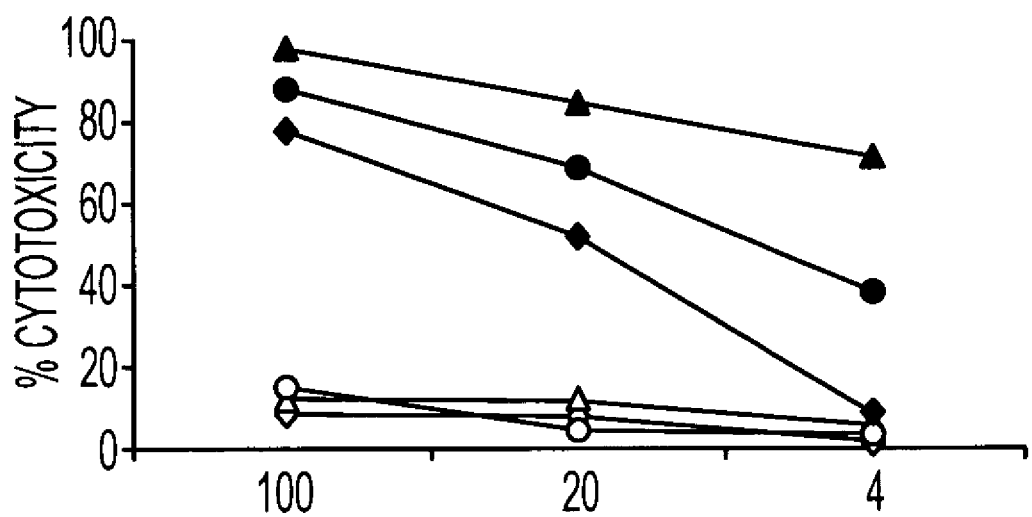
Figure 30E:
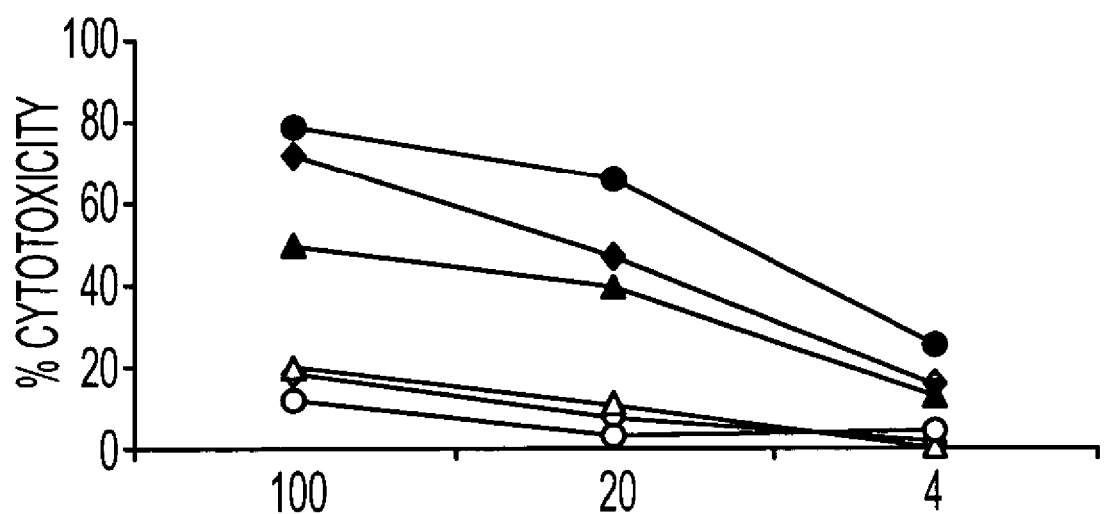

Splenocytes from HHDII mice immunized with rMVA were subjected to IVS, and then tested for lytic function in a standard CRA. Filled symbols show killing of T2 cell targets loaded with a pp65 or IE peptide, open symbols indicate killing of the same target cells loaded with P53$_{149-157}$. Each set of experiments was repeated at least twice. Lytic activity of splenocytes from two mice immunized with $10^7$ IU (FIG. 30A) or $2\times10^7$ IU (FIG. 30B) of pp65/pp150-MVA, against targets loaded with (closed symbols) pp65$_{495-503}$ or (open symbols) P53$_{149-157}$ are shown. In FIG. 30C, $5\times10^7$ IU of Ub-R-IE4-MVA were used to immunize two mice. Filled symbols represent individual mouse recognition of IEI$_{297-306}$ loaded targets, and open symbols indicate background lysis of targets loaded with P53$_{149-157}$. In FIGS. 30D and E, three mice were immunized with a mixture of $2.5\times10^7$ IU of pp65/pp150-MVA and $2.5\times10^7$ IU of Ub-R-IE4-MVA. Splenocytes from each spleen were stimulated separately with pp65$_{495-503}$ (FIG. 30D, filled symbols) and IEI$_{297-306}$ (FIG. 30E, filled symbols). In FIGS. 30D and E, open symbols indicate background lysis to P53$_{149-157}$, At E:T=20, significant differences (p<0.05) were detected between the activity against P53$_{149-157}$ and pp65$_{495-503}$ (FIG. 30D) and between P53$_{149-157}$ and IEI$_{297-306}$ (FIG. 30E), according to Welch's two-sided t-test.

pp65/pp150-MVA was able to stimulate a specific cytotoxic response against pp65$_{495-503}$ loaded T2 cells after a single immunization in HHDII mice (FIGS. 30A-B). Introduction of $10^7$ IU of pp65-MVA was sufficient for immune recognition, and responses reached plateau levels when $2\times10^7$ IU was administered (FIG. 30B). IE4-MVA also consistently elicited high levels of specific cytotoxicity to T2 targets loaded with IEI$_{297-306}$ after one round of IVS (FIG. 30C). Simultaneous immunization with two MVA expressing both pp65 and IE1 were evaluated analogously to the human in vitro studies discussed shown in Table V. In Table V, CRA killing is reported at E:T=100 for PBMC and at E:T=20 for post-IVS cultures. Combinations of pp65/pp150-MVA or Ub-R-pp65-MVA with IE4-MVA or Ub-R-IE4-MVA were administered to HHDII mice. All combinations of rMVA were able to elicit specific pp65 and IE1 cytotoxic response in the same mouse following IVS (data not shown), however the most consistent results were obtained when $2.5\times10^7$ IU of pp65/pp150-MVA and $2.5\times10^7$ IU of Ub-R-IE4-MVA were used (FIG. 30D-E).

TABLE V

Tetramer, IFN-γ T Cell Frequency and CRA Results of PBMC Pre-and Post-IVS.

| | % Tetramer binding | | | % IFN-γ | | | % CRA | | |
|---|---|---|---|---|---|---|---|---|---|
| UPN 009: PBMC | 6.89 | 2.90 | 0.38 | 4.60 | 2.97 | 0.19 | 34.89 | 19.03 | 11.56 |
| UPN 009: post-IVS | 72.26 | 32.30 | 0.13 | 16.70 | 7.40 | 0.22 | 99.19 | 69.05 | 9.91 |
| UPN 010: PBMC | 2.30 | 8.45 | 0.50 | 1.60 | 1.10 | 0.02 | 8.73 | 26.51 | 5.32 |
| UPN 010: post-IVS | 9.60 | 30.19 | 0.17 | 11.34 | 21.47 | 0.93 | 71.25 | 88.34 | 28.1 |
| UPN 011: PBMC | 0.37 | 3.00 | 0.08 | 0.45 | 2.00 | 0.05 | 3.64 | 9.68 | 0.01 |
| UPN 011: post-IVS | 3.91 | 57.44 | 0.41 | 1.73 | 17.17 | 0.21 | 61.58 | 97.71 | 22.37 |

Example 24

In vitro Stimulation Assay

Autologous Epstein-Barr-virus-transformed B cell lines were prepared to serve as antigen presenting cells by infection with either recombinant vaccinia expressing pp65Vac or Ub-R-pp65Vac. The infection with the vaccinia virus constructs was performed at an MOI of 5 for 2 hours in 2% FCS LCLM. Subsequently, the cells were exposed to 5000 rads using an Isomedix Model 19 Gammator (Nuclear Canada, Parsippany, N.J.) and were UV irradiated for 66 seconds using a Stratalinker 1800 instrument (Stratagene, Cedar Creek, Tex.) to inactivate vaccinia virus infectivity. Loss of infectivity was confirmed by a plaque assay, using CV-1 cells, following standard protocols known in the art as described by Earl and Moss in Ausubel et al. (Eds.) Recent Protocols in Molecular Biology, New York, N.Y., Greene/Wiley Interscience, 1998.

About 20 million fresh Ficoll-separated peripheral blood mononuclear cells were incubated with a saturating concentration of purified mouse anti-human CD4, CD16 and CD56 monoclonal antibodies (PharMingen, San Diego, Calif.). M450 Dynabead" goat anti-mouse IgG (Dynal AS, Oslo, Norway) then was added to the monoclonal antibody labeled peripheral blood mononuclear cells, which were depleted of CD4+, CD16+ and CD56+ cells using a magnet. The resulting population was greater than 80% CD8$^+$ as determined by fluorescence-activated cell sorting. $0.5\times10^6$ depleted peripheral blood mononuclear cells were used as effectors, together with $4\times10^5$ Ub-R-pp65Vac infected/irradiated antigen presenting cells and $2.5\times10^6$ autologous gamma-irradiated (2400 rads) peripheral blood mononuclear feeder cells, and plated in a 24-well plate at 2 ml per well in T cell culture medium (RPMI-1640 supplemented with 20% heat-inactivated human AB serum, 10 IU/ml recombinant interleukin-2 (Chiron, Emeryville, Calif.), 0.5 mM sodium pyruvate (Gibco-BRL Life Technologies, Rockville, Md.), HEPES, penicillin/streptomycin and glutamine). The cells were co-cultured for two weeks and fed with fresh medium when necessary. The cultures were analyzed after 7 or 12 days both for CMV-specific cytotoxic response and binding to CMV specific tetramers.

Example 25

Detection of CMV-Specific T Cells

The DNA constructs and viruses of this invention can be used to detect the presence of CMV-infected cells and therefore can form part of an in vitro diagnostic method for CMV. To detect CMV infection in a patient, a T lymphocyte sample is obtained from the patient according to known methods. The sample is contacted with or incubated with antigen presenting cells that have been infected with the viruses of the invention to present CMV antigens, such as those described in Example 11. Activation of CTL in the sample, which can be determined according to conventional methods, for example by detection of IFN-γ production, indicates the presence of CMV-infected cells in the patient and reveals that the patient has been infected with CMV.

MHC-I tetramer reagents, or any method known in the art may be used to detect T cells specifically recognizing particular epitopes. Tetramer reagents per se, as well as methods for preparing them, are known in the art. To make tetramer reagents for detecting CMV-specific T cells, a plasmid construct, pHN1-A2, expressing the extra-cellular and transmembrane portion of the HLA A*0201 heavy chain, and another plasmid, pHN1-β2M expressing the entire β2M (beta2-microglobulin) open reading frame were used. cDNA was prepared from donor cells of defined HLA-types, and the HLA heavy chain sequences were cloned. Clones corresponding to different HLA types were captured and sequenced. The HLA sequences were cloned into pHN-1 and expressed in $E.$ $coli$. The inclusion bodies from these bacteria were prepared, washed and stored as frozen aliquots for refolding into HLA/β2M/peptide complexes. The procedure used by the NIAID Tetramer Core Facility at Emory University, Atlanta were used for refolding and purifying tetramer complexes or adopted and modified. Using this method, about 0.1 to 1.7 milligrams of purified monomer generally can be prepared.

Figure 31:
FIG. 31 is a western blot showing results of a gel-shift assay for biotinylation of HSA:peptide:β2M complexes.

The purity of the final biotinylated and purified HLA/β2M/peptide complex was checked using SDS-PAGE electrophoresis. A streptavidin gel-shift assay also was used to determine the proportion of the HLA heavy chain that was biotinylated as follows. Streptavidin was incubated with the purified heavy chain/light chain/peptide complex and the product analyzed by 12% SDS-PAGE according to known methods, without heat denaturation prior to loading. Control reactions containing streptavidin or the complex alone were loaded on the gel for comparison. Streptavidin binds to the biotin moiety conjugated to the biotin substrate peptide sequence engineered at the carboxyl-terminal of the HLA heavy chain molecule. This leads to multimerization and an increase in apparent molecular weight of the HLA heavy chain, which is easily visible when the gel is stained. See FIG. 31.

Figure 32:
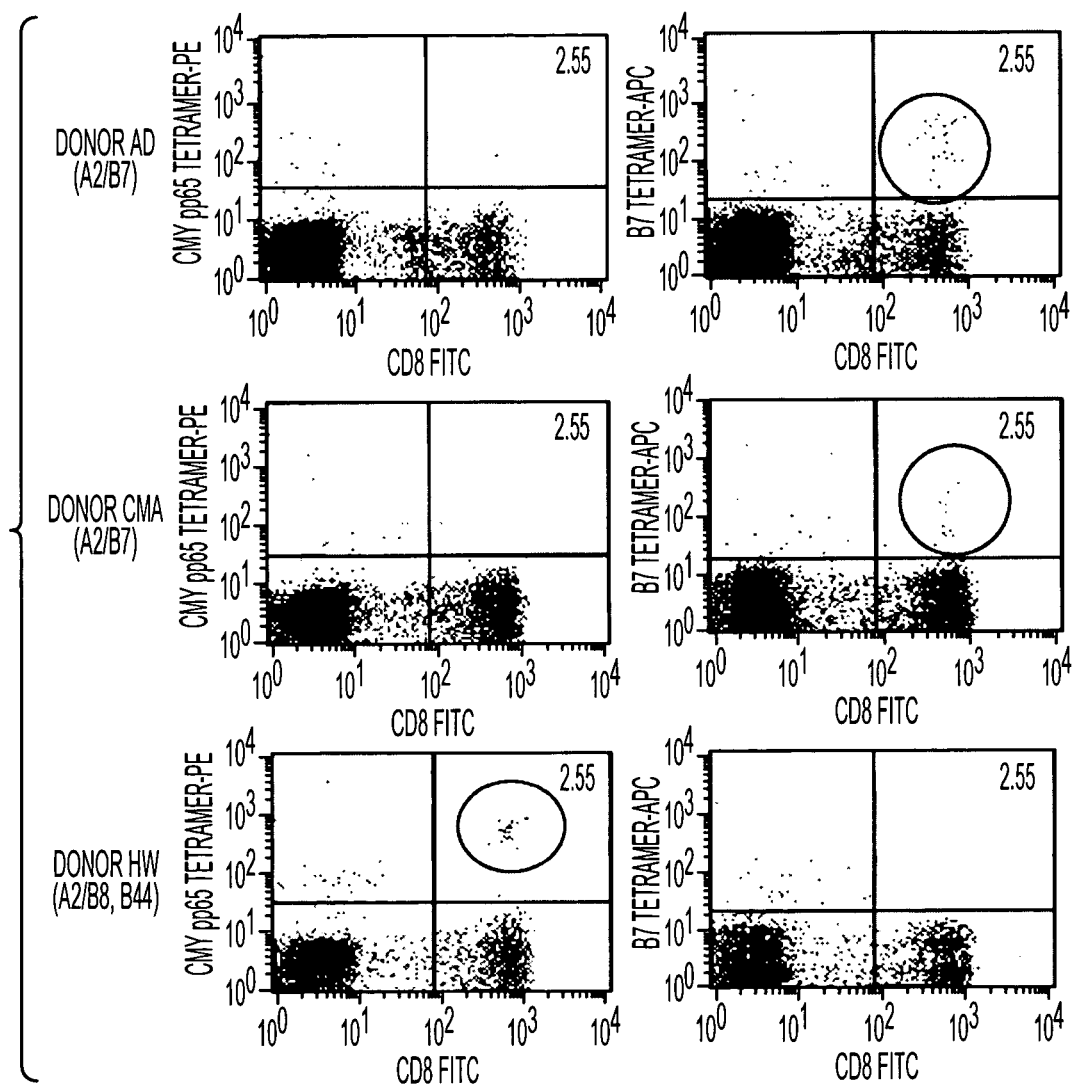
FIG. 32 shows fluorescence-activated cell sorting of peripheral blood mononuclear cells from healthy CMV-positive individuals of the indicated HLA haplotypes after staining with CMV-specific tetramer reagents and anti-CD8 antibody.

Two CMV-specific human tetramers: A*0201/CMV pp65$_{495\text{-}503}$ and B*0702/CMV pp65$_{265\text{-}275}$ were used to label peripheral blood mononuclear cells from healthy CMV-seropositive donors of various HLA haplotypes. The cells were analyzed by fluorescence activated cell sorting according to known methods with a gate set on lymphocytes as determined by forward and side scatter. See FIG. 32. The numbers in the upper right quadrants indicate the percentages of CD8$^+$ lymphocytes that bound the tetramer reagent indicated. The tetramer-binding populations of interest are circled. Quadrants were set by reference to the HLA-mismatched controls.

Example 26

Immunization of Bone Marrow Transplant Patients

A therapeutically active form of an antigenic compound according to the present invention is administered to an CMV-seropositive bone marrow transplant donor at a sufficient time prior to bone marrow transplant to enable the development of an anti-CMV cellular immune response prior to transplant (six to eight weeks, for example, in single or multiple doses separated by a given number of days or weeks).

Alternatively, T cells from the peripheral blood of the bone marrow or solid organ transplant donor are exposed in vitro to antigen presenting cells derived from the donor that are pre-infected with an MVA construct or constructs to elicit CMV-specific memory T cell responses, as was described in Example 11. The T cells of interest (CMV-specific T cells) are isolated using flow cytometry or magnetic methods in combination with a detection reagent according to known methods. Amplified T cells then are administered to the recipient of the bone marrow or solid organ transplant according to clinical necessity. The cells are administered in either purified or unpurified form for prophylaxis or according to therapeutic necessity to moderate ongoing infection or to prevent viremia as a result of CMV reactivation during immunosuppression after transplantation.

An additional vaccine regimen consists of priming a donor with a modified Vaccinia Ankara (MVA) containing a polynucleotide viral vaccine. If an unmanipulated BMT graft will be given to the recipient, such a graft will contain 25% or more of mature T cells. The T cells confer active immunity to the BMT recipient patient. Alternatively, when a T-cell depleted BMT graft is to be employed, an aliquot of T cells from the immunized donor can be administered to the patient following (for example, approximately 21 to 35 days) BMT to provide the recipient patient with CMV immunity.

Although certain preferred embodiments and examples of the invention have been described, the invention is not so limited. Persons skilled in this field of science will understand that the present invention is capable of wide application in the fields of diagnostics and therapeutics, and that modifications and variations can be made to the invention without departing from its spirit and scope.

Example 27

Recognition of CMV Infected Fibroblasts

To address whether rMVA-stimulated CMV-specific effectors recognized CMV-infected cells, IVS cell cultures were assayed on dermal fibroblasts infected with the AD169 CMV strain. Fibroblasts were either autologous or mismatched at two or more HLA loci. Specific killing of CMV infected autologous fibroblasts was detected in all specimen tested. See Table VI. Polyclonal IVS cultures, without undergoing a purification step, also displayed strong HLA-restricted recognition against allogeneic HLA A*0201 (or HLA B*0702 for UPN 005 and 008) CMV-infected fibroblasts, with a low percentage of non-specific killing (average 6%; Table VI, gray panel). Substantial cytotoxicity against infected fibroflasts was found in cultures raised from UPN 009, 010, 011 stimulated by IE4-MVA and UbRIE4-MVA. This was surprising, since CMV-IE1 CTL clones were reported to inefficiently recognize AD169-infected fibroblasts.

HLA Class I tetramer binding and functional assays employed in this study, such as CRA and ICC for IFN-γ, revealed that T cell lines obtained after one IVS were largely CMV-epitope specific. They were able to kill both autologous and allogeneic (HLA A*0201 or HLA B*0702, mismatched at other loci) CMV-infected fibroblasts with low alloreactivity (Table VI, gray panel). This result, critically augments the feasibility of this approach for clinical use. Regardless of the subject's previous immune status to EBV or poxvirus, substantial CMV cellular immunity was detected. In particular IFN-γ production to immunodominant EBV (BMLF) and poxvirus (VP35#1; 74A and 165) epitopes never exceeded 2% among various post-IVS CD8⁺ population tested (data not shown). The IVS method, in which PBMC are magnetically depleted of T-helper and NK cells, can be also performed to generate CD4⁺ enriched T cells by depleting CD8⁺ and NK cells, can be also performed to generate CD4⁺ enriched T cells by depleting CD8⁺ and NK cells (La Rosa et al., unpublished). Since adoptively transferred CD8⁺ CMV-specific T-cell clones do not persist long-term without endogenous recovery of CD4⁺ T cells, immunotherapy protocols would be more effective if CD4⁺ T cells were provided, especially for HSCT recipients who lack CMV-specific CD4⁺ T-help responses.

Unexpectedly good cytoxicity to infected fibroblasts was found using IE4-MVA and UbRIE4-MVA stimulated PBMC cultures, comparable to that obtained with pp65-poxvirus stimulated cultures (Table VI). Newly synthesized viral proteins, such as CMV-IE1 are not efficiently presented by CMV AD169-infected fibroblasts. Based on these findings, IE1 epitopes are presented on CMV-infected fibroblasts, despite viral interference. Usage of a bulk culture specific for full-length IE1 protein, rather than IE1 epitope-specific clones may reflect the in vivo milieu in which there is evidence of abundant IE1-specific CTL, and explain why IE1-specific CTL in mice and humans were detected easily, in contrast to other reports.

TABLE VI

Recognition of CMV infected fibroblasts after IVS with CMV-poxvirus constructs.

| UPN | IVS | CMC infected Autologous | untreated Autologous | CMC infected Autologous | untreated Autologous |
|---|---|---|---|---|---|
| 001 | pp65/pp150-MVA | 40.0 | 3.5 | | |
| 004 | pp65-VV | 20.7 | 0.9 | | |
| 005 | UbRpp65-VV | 48.4 | 10.1 | | |
| 008 | UbRpp65-VV | 31.0 | 2.9 | | |
| 009 | pp65/pp150-MVA | 43.3 | 7.3 | | |
| 009 | IE4-MVA | 28.9 | 0.5 | | |
| 009 | pp65/pp150-MVA + IE4-MVA | 34.5 | 7.2 | | |
| 010 | UbRpp65/pp150-MVA + IE4-MVA | N/A | N/A | | |
| 010 | UbRIE4-MVA | N/A | N/A | | |
| 011 | pp65/pp150-MVA + IE4-MVA | 43.8 | 0.9 | | |
| 011 | IE4-MVA | 30.4 | 3.4 | | |

Fibroblasts were infected with CMV AD169 and used as targets in CRA as described in "M & M." Effectors were PBMC stimulated 7–12 days with various CMV-poxvirus constructs, as detailed in "M & M." The percentage killing of autologous (left panel) and HLA A*0201 (or HLA A*0702 for UPN 005 and 008) allogeneic (right grey panel) fibroblasts, mis-matched at least at 2 othre HLA loci are shown at E/T 20 for each donor. N/A indicates that either fibroblasts or effectorcells were not available for the assay.

The invention claimed is:

1. A Modified Vaccinia Ankara Virus vaccine vector which comprises a DNA construct which comprises DNA encoding one or more human cytomegalovirus proteins selected from the group consisting of pp65, pp150, IE1, gB and antigenic fragments thereof, wherein optionally one or more of said human cytomegalovirus proteins or antigenic fragments thereof is modified by N-terminal ubiquitination, N-end modification or both, and wherein said human cytomegalovirus protein or antigenic fragment thereof optionally contains a lysine-containing adapter sequence.

2. A protein encoded by a DNA construct which comprises DNA encoding one or more human cytomegalovirus proteins selected from the group consisting of pp65, pp150, IE1, gB and antigenic fragments thereof, wherein optionally one or more of said human cytomegalovirus proteins or antigenic fragments thereof is modified by N-terminal ubiquitination, N-end modification or both, and wherein said human cytomegalovirus protein or antigenic fragment thereof optionally contains a lysine-containing adapter sequence.

3. A Modified Vaccinia Virus vaccine vector of claim 1 which comprises Ub-R-pp65, Ub-R-pp150, Ub-R-IE1(4) and gB(s).

4. A DNA construct which comprises DNA encoding one or more human cytomegalovirus proteins selected from the group consisting of pp65, pp150, IE1, gB and antigenic fragments thereof, wherein optionally one or more of said human cytomegalovirus proteins or antigenic fragments thereof is modified by N-terminal ubiquitination, N-end modification or both, and wherein said human cytomegalovirus protein or antigenic fragment thereof optionally contains a lysine-containing adapter sequence, and wherein said DNA encodes:
   (a) ubiquitinated, N-terminal arginine, phosphokinase-deleted pp65;
   (b) ubiquitinated, N-terminal arginine pp150;
   (c) ubiquitinated, N-terminal arginine IE1 exon 4; and
   (d) transmembrane domain-deleted gB.

5. A Modified Vaccinia Virus vaccine vector which comprises the DNA constructed in claim 4.

6. A method of vaccinating a person in need thereof against human cytomegalovirus which comprises administering to said person an effective amount of the vaccine virus vector of claim 1.

7. A method of augmenting immunity against human cytomegalovirus in a person in need thereof which comprises administering to said person an effective amount of the vaccine virus vector of claim 1.

* * * * *

UNITED STATES PATENT AND TRADEMARK OFFICE
CERTIFICATE OF CORRECTION

PATENT NO. : 7,163,685 B2
APPLICATION NO. : 10/825629
DATED : January 16, 2007
INVENTOR(S) : Diamond et al.

It is certified that error appears in the above-identified patent and that said Letters Patent is hereby corrected as shown below:

On the Title Page, Item -56-

Page 2, left column, line 51, "CD8*" should be-- $CD8^+$ --

Page 2, right column, line 21, insert -- " -- after "Immunity."

Page 2, right column, line 24, insert -- " -- after "Candidate."

Page 2, right column, line 56, "Eptiope" should be --Epitope--

Page 3, left column, line 3, "Transportation" should be --Transplantation--

Page 3, left column, line 5, "CD8*" should be -- $CD8^+$ --

Page 3, left column, line 6, "Cytomegalvirus" should be --Cytomegalovirus--

Page 3, left column, line 6, "Intermediate" should be --Immediate--

Page 3, left column, line 7, "CD8*" should be -- $CD8^+$ --

Page 3, left column, line 19, "CD8*" should be $CD8^+$ --

Page 3, left column, line 54, "CD8*" should be -- $CD8^+$ --

Page 3, right column, line 22, "Pandeet al." should be --Pande et al.--

Page 3, right column, line 47, "Cytomegatovirus" should be --Cytomegalovirus--

Page 4, left column, line 42, delete second instance of "(3)"

Page 4, right column, line 14, "CD4*" should be -- $CD4^+$ --

Page 4, right column, line 14, "CD8*" should be -- $CD8^+$ --

Page 4, right column, line 34, insert --" -- before "How"

Page 4, right column, line 34, insert --" -- after "pathway."

Col. 8, line 1, "8:1320-136" should be --8:130-136--

UNITED STATES PATENT AND TRADEMARK OFFICE
CERTIFICATE OF CORRECTION

PATENT NO. : 7,163,685 B2
APPLICATION NO. : 10/825629
DATED : January 16, 2007
INVENTOR(S) : Diamond et al.

It is certified that error appears in the above-identified patent and that said Letters Patent is hereby corrected as shown below:

Col. 8, line 25, delete "the"

Col. 10, line 30, "rvac" should be --rVac--

Col. 11, line 10, "$10^{9-1010}$/ml" should be --$10^9$-$10^{10}$/ml--

Col. 11, line 28, "such a" should be --such as--

Col. 18, line 3, delete second instance of "then"

Col. 19, line 26, "BiORad" should be --BioRad--

Col. 25, line 65, "wit" should be --with--

Col. 26, line 25, "ell" should be --Cell--

Col. 26, line 29, delete "1"

Col. 26, line 32, "portein" should be --protein--

Col. 27, line 4, "waster" should be --waste--

Col. 27, line 37, insert --)-- after "14"

Col. 29, line 64, "0.5 ml" should be --5 ml--

Col. 30, line 2, "OptiMEMT$^{TM}$" should be --OptiMEM$^{TM}$--

Col. 30, line 4, "OptiMEMT$^{TM}$" should be --OptiMEM$^{TM}$--

Col. 30, line 35, "for" should be --to--

Col. 32, line 10, "α-glucoronidase A)" should be --(x-glucoronidase A)--

Col. 32, line 25, "aB(s)" should be --gB(s)--

Col. 33, line 63, "in" should be --is--

Col. 34, line 21, "A 0201" should be --A*0201--

UNITED STATES PATENT AND TRADEMARK OFFICE
CERTIFICATE OF CORRECTION

PATENT NO. : 7,163,685 B2
APPLICATION NO. : 10/825629
DATED : January 16, 2007
INVENTOR(S) : Diamond et al.

It is certified that error appears in the above-identified patent and that said Letters Patent is hereby corrected as shown below:

Col. 35, line 40, "HIV PO1$_{464-472}$" should be --HIV pol$_{464-472}$--

Col. 36, line 18, "IFN-γ+by" should be --IFN-γ+ by--

Col. 36, line 32, "UbRpp65-MVA" should be --Ub-R-pp65-MVA--

Col. 36, line 34, "(<68-fold)" should be --(≤68-fold)--

Col. 37, line 22, "P53149-157" should be --p53$_{149-157}$--

Col. 37, line 25, "P53$_{149-157}$" should be --p53$_{149-157}$--

Col. 37, line 34, "HIV Pol$_{465-472}$" should be --HIV pol$_{464-472}$--

Col. 37, line 39, "P53$_{149-157}$" should be --p53$_{149-157}$--

Col. 38, line 39, "aB" should be --gB--

Col. 40, line 41, "P53$_{149-157}$" should be --p53$_{149-157}$--

Col. 41, line 35, "P53" should be --p53--

Col, 41, line 36, "157" should be --$_{157}$--

Col. 41, line 40, "P53$_{149-157}$" should be --p53$_{149-157}$--

Col. 41, line 44, "P53$_{149-157}$" should be --p53$_{149-157}$--

Col. 41, line 51, "P53$_{149-157}$" should be --p53$_{149-157}$--

Col. 41, line 52, "P53$_{149-157}$" should be --p53$_{149-157}$--

Col. 41, line 53, "P53$_{149-157}$" should be --p53$_{149-157}$--

Col. 43, line 5, delete ")" after "glutamine"

Col. 45, line 28, delete "," after "cells"

Col. 45, lines 28 through 30, delete second instance of "can be also performed to generate CD4$^+$ enriched T cells by depleting CD8$^+$ and NK"

UNITED STATES PATENT AND TRADEMARK OFFICE
CERTIFICATE OF CORRECTION

PATENT NO. : 7,163,685 B2
APPLICATION NO. : 10/825629
DATED : January 16, 2007
INVENTOR(S) : Diamond et al.

It is certified that error appears in the above-identified patent and that said Letters Patent is hereby corrected as shown below:

Col. 46, line 42, "othre" should be --other--

Col. 42, line 43, "effectorcells" should be --effector cells--

Signed and Sealed this

Nineteenth Day of June, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,163,685 B2 | Page 1 of 1 |
| APPLICATION NO. | : 10/825629 | |
| DATED | : January 16, 2007 | |
| INVENTOR(S) | : Diamond et al. | |

It is certified that error appears in the above-identified patent and that said Letters Patent is hereby corrected as shown below:

Col. 1, line 17, "may have" should read -- has --.

Signed and Sealed this

Twenty-ninth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,163,685 B2
APPLICATION NO. : 10/825629
DATED : January 16, 2007
INVENTOR(S) : Don Jeffrey Diamond et al.

It is certified that error appears in the above-identified patent and that said Letters Patent is hereby corrected as shown below:

In the Specification

Column 1, Lines 12-18:
"This invention was made with government support in the form of grant nos. CA30206 and CA77544 from the United States Department of Health and Human Services, National Cancer Institute; AI44313 and AI52065 from the Unites States Department of Health and Human Services (DAIDS) and LS46116-98 (LLS). The government may have certain rights in the invention."

Should be:
-- This invention was made with government support under CA030206, AI044313, and CA077544 awarded by the National Institutes of Health. The government has certain rights in the invention. --

Signed and Sealed this
Sixteenth Day of April, 2024

Katherine Kelly Vidal
*Director of the United States Patent and Trademark Office*